United States Patent
Herbowy et al.

(10) Patent No.: US 9,072,578 B2
(45) Date of Patent: *Jul. 7, 2015

(54) INTRA-VAGINAL DEVICE FOR FECAL INCONTINENCE

(75) Inventors: Steven Lawrence Herbowy, Palo Alto, CA (US); Miles Harris Rosen, Palo Alto, CA (US); Jacob Samuel Brenner, Menlo Park, CA (US)

(73) Assignee: Pelvalon, Inc., Sunnyvale, CA (US)

( * ) Notice: Subject to any disclaimer, the term of this patent is extended or adjusted under 35 U.S.C. 154(b) by 263 days.

This patent is subject to a terminal disclaimer.

(21) Appl. No.: 13/635,598

(22) PCT Filed: Mar. 16, 2011

(86) PCT No.: PCT/US2011/028691
§ 371 (c)(1),
(2), (4) Date: Sep. 17, 2012

(87) PCT Pub. No.: WO2011/116108
PCT Pub. Date: Sep. 22, 2011

(65) Prior Publication Data
US 2013/0012764 A1    Jan. 10, 2013

Related U.S. Application Data

(60) Provisional application No. 61/314,335, filed on Mar. 16, 2010, provisional application No. 61/367,418, filed on Jul. 25, 2010.

(51) Int. Cl.
*A61F 2/00* (2006.01)
*A61F 6/08* (2006.01)

(52) U.S. Cl.
CPC .............. *A61F 2/0009* (2013.01); *A61F 2/0013* (2013.01); *A61F 2/005* (2013.01); *A61F 6/08* (2013.01)

(58) Field of Classification Search
CPC ..... A61F 2/0004; A61F 2/005; A61F 2/0009; A61F 2/0013; A61F 2/0027; A61F 6/08; A61F 2/0022; A61F 2/0031; A61B 17/12022; A61B 2/0004; A61B 2/0009; A61B 2/0013; A61B 2/0027; A61B 6/08; A61B 17/42

USPC ........ 600/29–32, 37; 128/830, 834–836, 885, 128/DIG. 25

See application file for complete search history.

(56) References Cited

U.S. PATENT DOCUMENTS

| 186,469 A | 1/1877 | Fowler |
| 1,282,881 A | 10/1918 | Landis |

(Continued)

FOREIGN PATENT DOCUMENTS

| DE | 2438691 A1 | 8/1974 |
| EP | 0068318 A1 | 1/1983 |

(Continued)

OTHER PUBLICATIONS

Viera et al.; Practical use of the pessary; Am Fam Physician; 61(9); pp. 2719-2726; May 1, 2000 ( downloaded Mar. 8, 2013 from: http://www.aafp.org/afp/2000/0501/p2719.html?printable=afp).

(Continued)

*Primary Examiner* — Charles A Marmor, II
*Assistant Examiner* — Carrie R Dorna
(74) *Attorney, Agent, or Firm* — Fish & Richardson P.C.

(57) ABSTRACT

An intra-vaginal device for the control of stool passage, including a body mechanism for securing the device around the area of the pubic notch and in the area of the posterior fornix, the body mechanism including a force applying mechanism for reversibly applying a force to a posterior portion of the vagina to occlude the rectum. A method of controlling the passage of stool in a patient, by inserting an intra-vaginal device into the patient's vagina such that an anterior end rests around the pubic notch and a posterior end rests in the posterior fornix, exerting a force towards the posterior side of the vagina, moving an anterior wall of the patient's rectum towards the posterior wall of the rectum with the force applying portion, impeding the passage of stool, and removing the force, allowing stool to pass.

41 Claims, 41 Drawing Sheets

(56) References Cited

U.S. PATENT DOCUMENTS

| | | | |
|---|---|---|---|
| 2,475,071 A * | 7/1949 | Young | 128/837 |
| 2,638,093 A * | 5/1953 | Kulick | 600/29 |
| 3,554,184 A | 1/1971 | Habib | |
| 3,646,929 A | 3/1972 | Bonnar | |
| 3,675,656 A | 7/1972 | Hakim | |
| 3,705,575 A | 12/1972 | Edwards | |
| 3,709,215 A | 1/1973 | Richmond | |
| 3,797,478 A | 3/1974 | Walsh et al. | |
| 3,831,583 A | 8/1974 | Edmunds, Jr. et al. | |
| 3,841,304 A | 10/1974 | Jones | |
| 3,866,611 A | 2/1975 | Baumrucker | |
| 3,882,852 A | 5/1975 | Sinnreich | |
| 3,903,894 A | 9/1975 | Rosen et al. | |
| 4,019,499 A | 4/1977 | Fitzgerald | |
| 4,031,886 A | 6/1977 | Morhenn | |
| 4,307,716 A * | 12/1981 | Davis | 128/834 |
| 4,428,365 A | 1/1984 | Hakky | |
| 4,587,954 A | 5/1986 | Haber | |
| 4,669,478 A | 6/1987 | Robertson | |
| 4,686,985 A | 8/1987 | Lottick | |
| 4,786,276 A | 11/1988 | Haber | |
| 4,823,814 A | 4/1989 | Drogendijk et al. | |
| 4,846,818 A | 7/1989 | Keldahl et al. | |
| 4,854,990 A | 8/1989 | David | |
| 4,946,449 A | 8/1990 | Davis, Jr. | |
| 4,981,470 A | 1/1991 | Bombeck, IV | |
| 5,007,894 A | 4/1991 | Enhorning | |
| 5,041,077 A | 8/1991 | Kulick | |
| 5,147,301 A | 9/1992 | Ruvio | |
| 5,224,494 A | 7/1993 | Enhorning | |
| 5,306,226 A | 4/1994 | Salama | |
| 5,370,690 A | 12/1994 | Barrett | |
| 5,474,518 A | 12/1995 | Farrer Velazquez | |
| 5,520,606 A | 5/1996 | Schoolman et al. | |
| 5,545,176 A | 8/1996 | Murtfeldt | |
| 5,593,443 A | 1/1997 | Carter et al. | |
| 5,603,685 A | 2/1997 | Tutrone, Jr. | |
| 5,611,768 A | 3/1997 | Tutrone, Jr. | |
| 5,702,421 A | 12/1997 | Schneidt | |
| 5,733,230 A | 3/1998 | Sawchuck et al. | |
| 5,782,745 A * | 7/1998 | Benderev | 600/30 |
| 5,884,629 A | 3/1999 | O'Brien | |
| 6,013,023 A | 1/2000 | Klingenstein | |
| 6,030,338 A | 2/2000 | Benderev | |
| 6,048,306 A | 4/2000 | Spielberg | |
| 6,090,038 A | 7/2000 | Zunker et al. | |
| 6,090,098 A | 7/2000 | Zunker et al. | |
| 6,096,057 A | 8/2000 | Klingenstein | |
| 6,110,099 A | 8/2000 | Benderev | |
| 6,135,945 A | 10/2000 | Sultan | |
| 6,142,928 A | 11/2000 | Zunker et al. | |
| 6,216,698 B1 | 4/2001 | Regula | |
| 6,319,191 B1 | 11/2001 | Sayet et al. | |
| 6,418,930 B1 * | 7/2002 | Fowler | 128/830 |
| 6,428,467 B1 | 8/2002 | Benderev | |
| 6,470,890 B1 | 10/2002 | Diokno et al. | |
| 6,482,145 B1 | 11/2002 | Forsell | |
| 6,503,190 B1 | 1/2003 | Ulmsten et al. | |
| 6,558,370 B2 | 5/2003 | Moser | |
| 6,569,078 B2 | 5/2003 | Ishikawa et al. | |
| 6,645,137 B2 | 11/2003 | Ulmsten et al. | |
| 6,676,594 B1 | 1/2004 | Zunker et al. | |
| 6,682,473 B1 | 1/2004 | Matsuura et al. | |
| 6,723,040 B2 | 4/2004 | Brady | |
| 6,752,754 B1 | 6/2004 | Feng et al. | |
| 6,770,025 B2 | 8/2004 | Zunker | |
| 6,786,861 B1 | 9/2004 | Pretorius | |
| 6,808,485 B2 | 10/2004 | Zunker | |
| 6,843,766 B1 | 1/2005 | Nemir et al. | |
| 6,913,573 B1 | 7/2005 | Viscomi et al. | |
| 6,915,165 B2 | 7/2005 | Forsell | |
| 6,939,289 B2 | 9/2005 | Zunker et al. | |
| 6,976,950 B2 | 12/2005 | Connors et al. | |
| 7,074,178 B2 | 7/2006 | Connors et al. | |
| 7,083,569 B2 | 8/2006 | Boulanger et al. | |
| 7,144,391 B1 | 12/2006 | Kreutz et al. | |
| 7,235,044 B2 | 6/2007 | Forsell | |
| 7,258,661 B2 | 8/2007 | Davies et al. | |
| 7,306,586 B2 | 12/2007 | Beaufore et al. | |
| 7,311,661 B2 | 12/2007 | Heinrich | |
| 7,360,544 B2 | 4/2008 | Levien | |
| 7,445,598 B2 | 11/2008 | Orban, III | |
| 7,540,876 B2 | 6/2009 | Connors et al. | |
| 7,553,273 B2 | 6/2009 | Ferguson et al. | |
| 7,628,155 B2 | 12/2009 | Carey | |
| 7,628,156 B2 | 12/2009 | Astani et al. | |
| 7,658,196 B2 | 2/2010 | Ferreri et al. | |
| 7,673,631 B2 | 3/2010 | Astani et al. | |
| 7,691,051 B2 | 4/2010 | Connors et al. | |
| 7,695,427 B2 | 4/2010 | Kugler et al. | |
| 7,717,892 B2 | 5/2010 | Bartning et al. | |
| 7,722,583 B2 | 5/2010 | Kim et al. | |
| 7,771,344 B2 | 8/2010 | Ziv | |
| 7,771,346 B2 | 8/2010 | Burton et al. | |
| 7,775,215 B2 | 8/2010 | Hassler, Jr. et al. | |
| 7,775,966 B2 | 8/2010 | Dlugos et al. | |
| 7,794,385 B2 | 9/2010 | Rosenblatt | |
| 7,819,821 B2 | 10/2010 | Forte et al. | |
| 7,828,713 B2 | 11/2010 | Ziv et al. | |
| 7,828,714 B2 | 11/2010 | Feng et al. | |
| 7,828,715 B2 | 11/2010 | Haverfield | |
| 7,828,716 B2 | 11/2010 | Burton et al. | |
| 7,844,342 B2 | 11/2010 | Dlugos, Jr. et al. | |
| 7,892,163 B2 | 2/2011 | Bartning et al. | |
| 7,927,270 B2 | 4/2011 | Dlugos et al. | |
| 7,927,320 B2 | 4/2011 | Goldwasser et al. | |
| 8,740,766 B2 | 6/2014 | Rosen et al. | |
| 8,740,767 B2 | 6/2014 | Rosen et al. | |
| 2006/0025798 A1 | 2/2006 | Cook et al. | |
| 2006/0211911 A1 | 9/2006 | Jao et al. | |
| 2008/0033231 A1 | 2/2008 | Bartning et al. | |
| 2009/0111671 A1 | 4/2009 | Campbell et al. | |
| 2009/0192346 A1 | 7/2009 | Rosenblatt | |
| 2009/0216071 A1 | 8/2009 | Zipper | |
| 2011/0015474 A1 | 1/2011 | Forsell | |
| 2012/0116415 A1 | 5/2012 | Forsell | |
| 2013/0012764 A1 | 1/2013 | Herbowy et al. | |
| 2013/0138135 A1 | 5/2013 | Rosen et al. | |
| 2013/0144112 A1 | 6/2013 | Rosen et al. | |
| 2013/0150661 A1 | 6/2013 | Rosen et al. | |

FOREIGN PATENT DOCUMENTS

| | | |
|---|---|---|
| EP | 1518514 A2 | 3/2005 |
| EP | 1587464 B1 | 8/2007 |
| EP | 1587465 B1 | 11/2007 |
| EP | 1609440 B1 | 7/2008 |
| EP | 1734895 B | 7/2008 |
| EP | 1734892 B1 | 3/2011 |
| EP | 1990023 B1 | 9/2012 |
| FR | 2843700 A1 | 2/2004 |
| GB | 2352181 A | 1/2001 |
| WO | WO93/16659 A1 | 9/1993 |
| WO | WO96/01084 A1 | 1/1996 |
| WO | WO01/45487 A2 | 6/2001 |
| WO | WO02/053235 A2 | 7/2002 |
| WO | WO02/098323 A1 | 12/2002 |
| WO | WO2005/082276 A1 | 9/2005 |
| WO | WO2008/085825 | 7/2008 |
| WO | WO2009/046996 A2 | 4/2009 |
| WO | WO2009/046997 A2 | 4/2009 |
| WO | WO2009/060437 A2 | 5/2009 |
| WO | WO2011/008167 A1 | 1/2011 |
| WO | WO2011/116108 | 9/2011 |

OTHER PUBLICATIONS

Rosen et al.; U.S. Appl. No. 13/679,484 entitled "Intra-Vaginal Devices and Methods for Treating Fecal Incontinence," filed Nov. 16, 2012.

Rosen et al.; U.S. Appl. No. 13/679,528 entitled "Intra-Vaginal Devices and Methods for Treating Fecal Incontinence," filed Nov. 16, 2012.

(56) References Cited

OTHER PUBLICATIONS

Rosen et al.; U.S. Appl. No. 13/625,683 entitled "Intra-Vaginal Devices and Methods for Treating Fecal Incontinence," filed Sep. 24, 2012.

Sokol et al; Clinical Anatomy of the Vulva, Vagina, Lower Pelvis, and Perineum; Global Library of Women's Medicine; 14 pgs.; Sep. 2008 (printed from http://www.glowm.com/section_view/heading/Clinical%20Anatomy%20of%20the%20V on Dec. 23, 2013).

Viera et al.; Practical use of the pessary; Am Fam Physician; 61(9); pp. 2719-2726; May 1, 2000( downloaded Mar. 8, 2013 from: http://www.aafp.org/afp/2000/0501/p2719.html?printable=afp).

\* cited by examiner

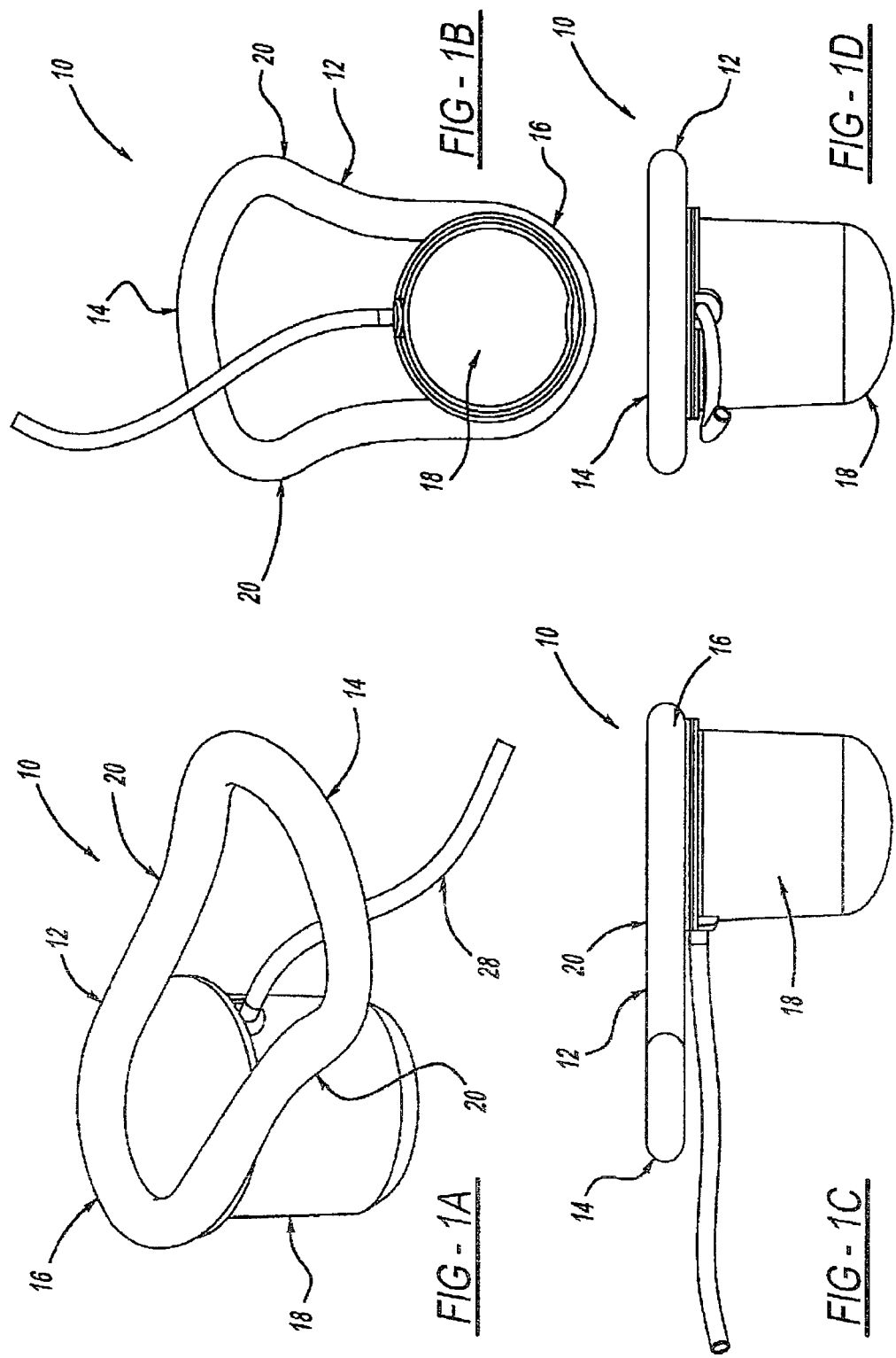

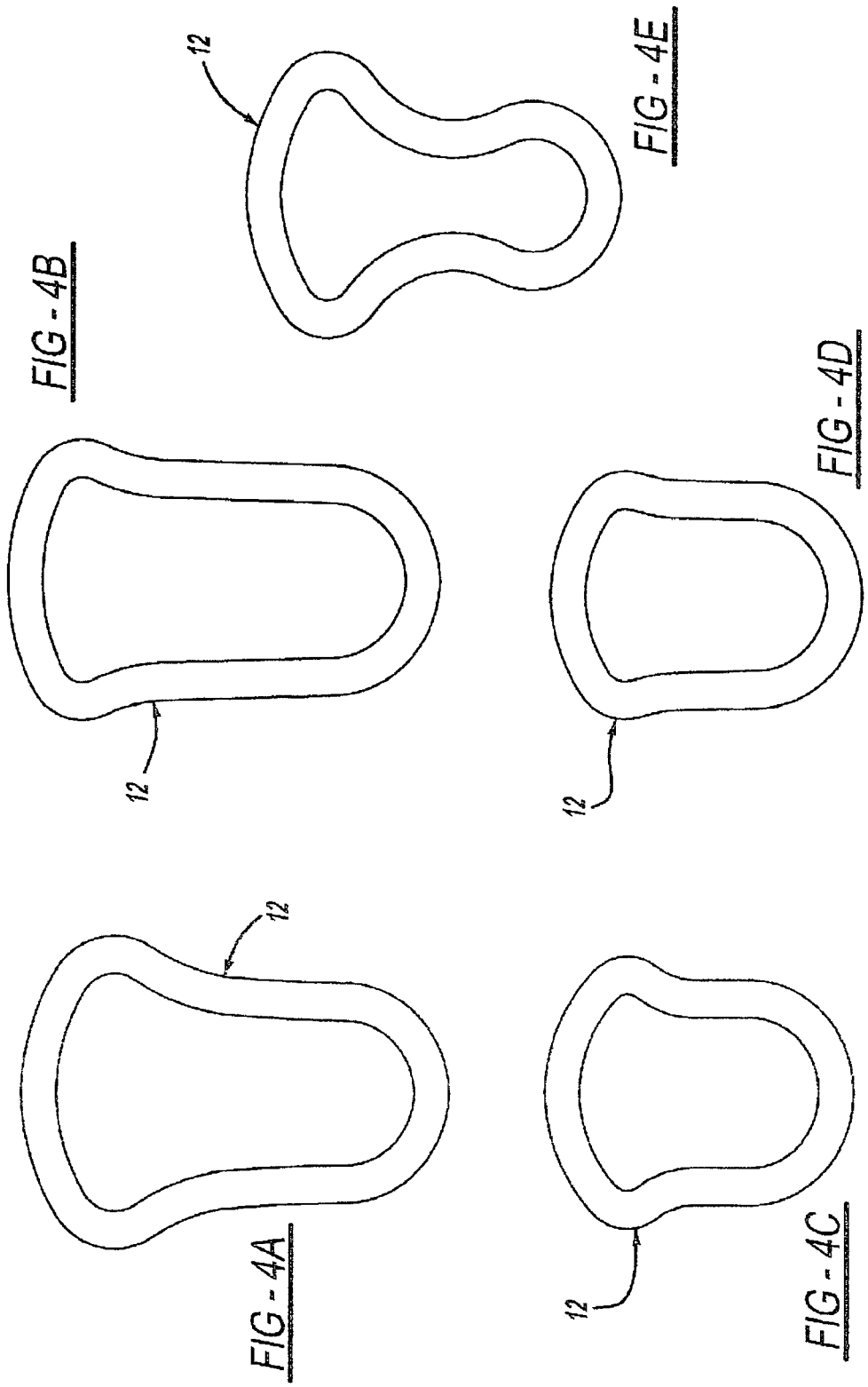

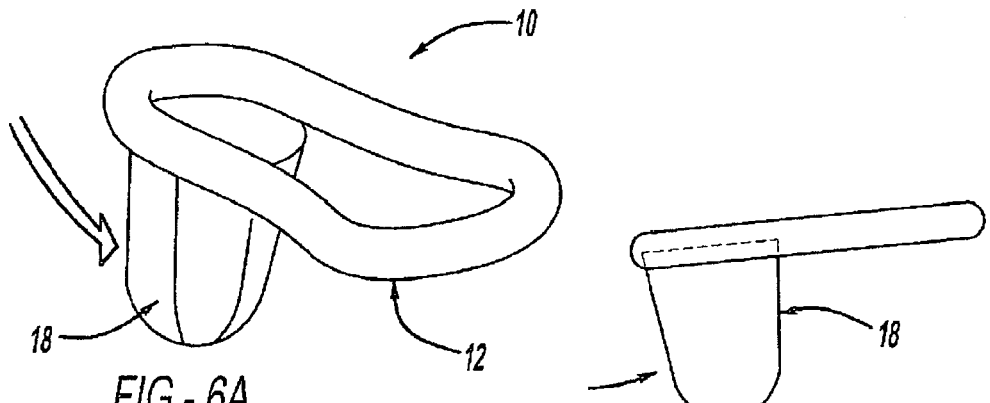
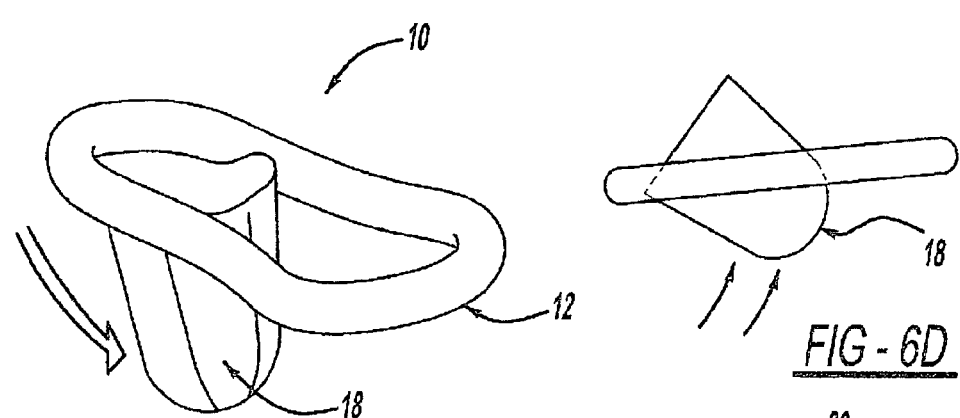
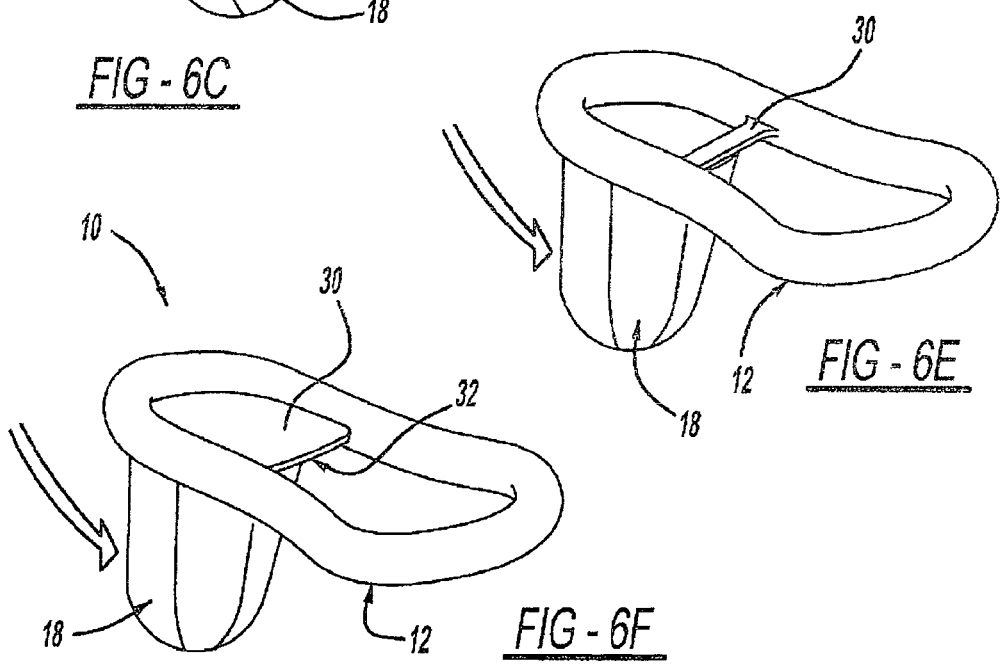

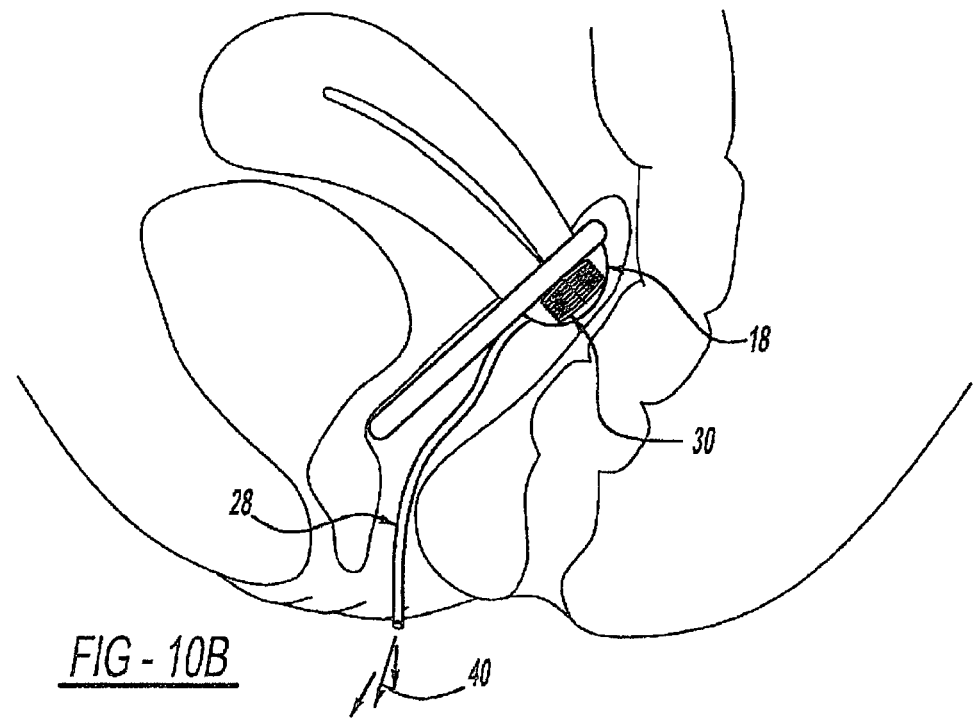
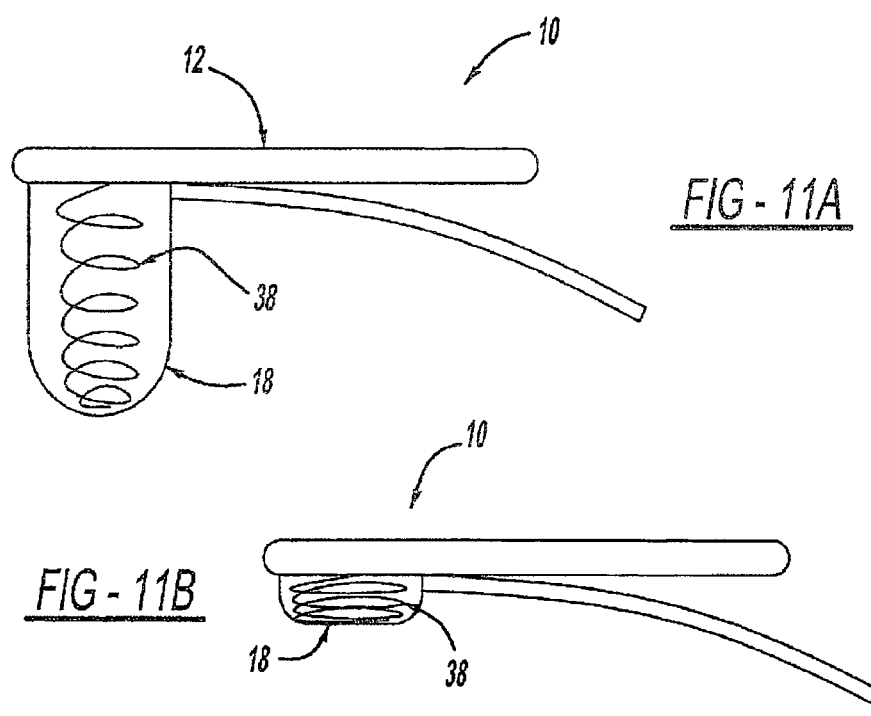

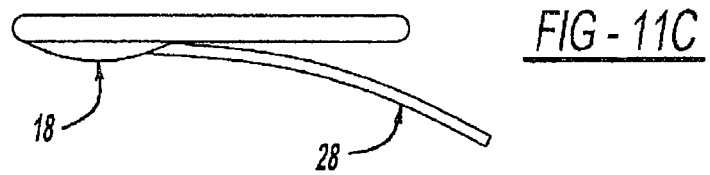
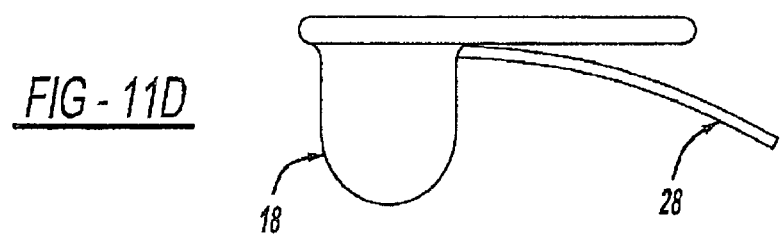
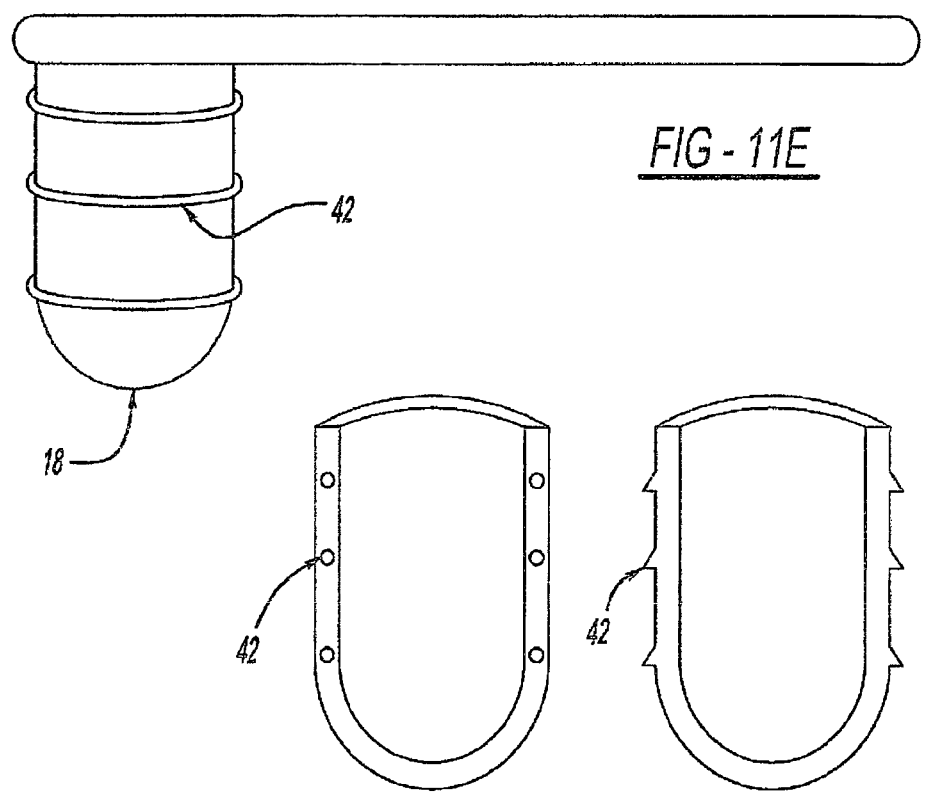

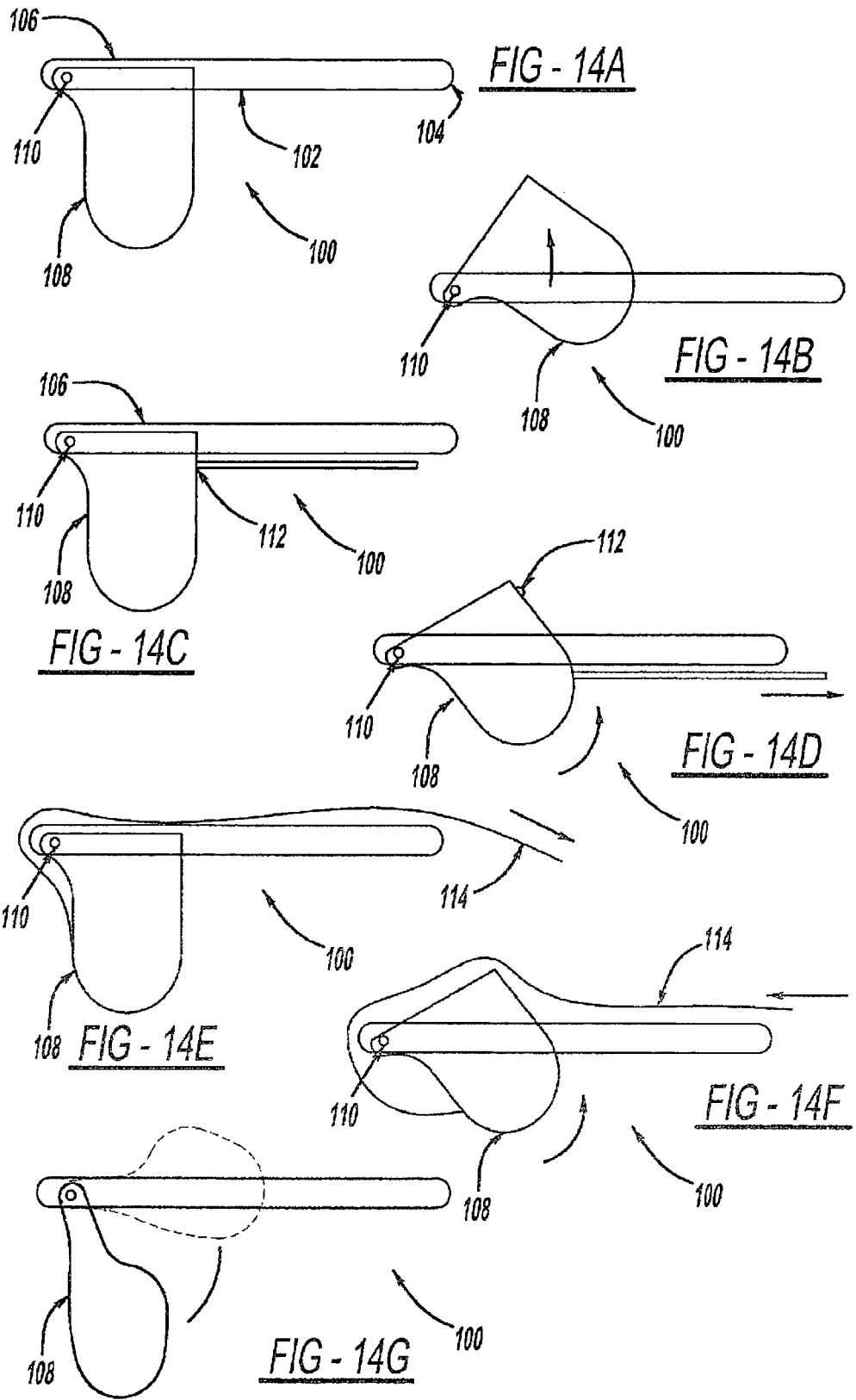

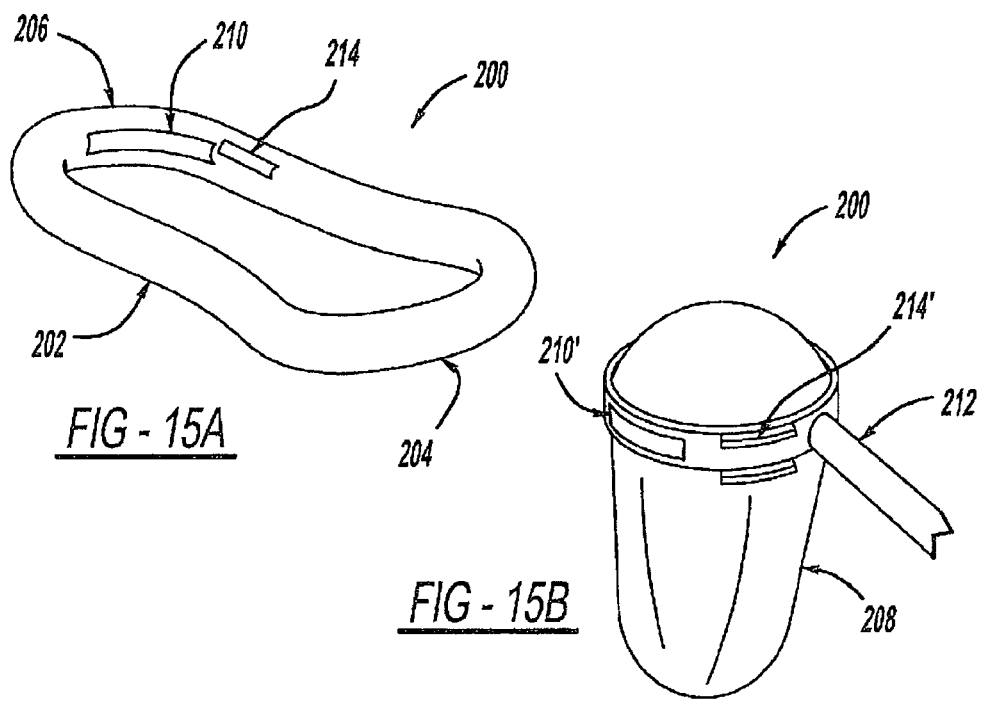
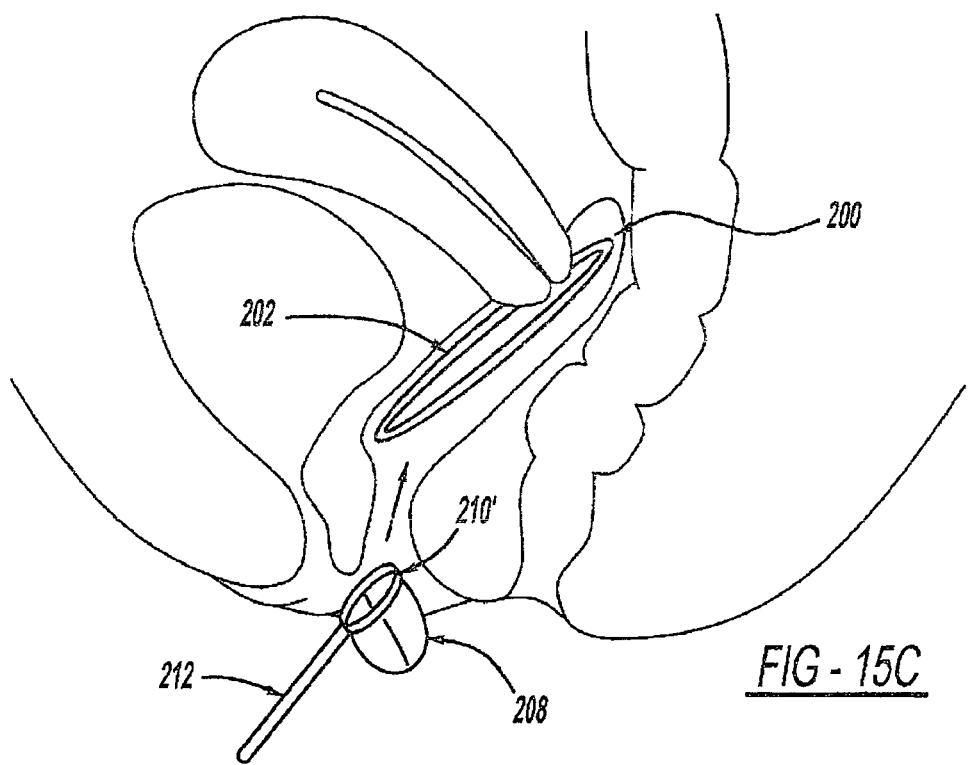

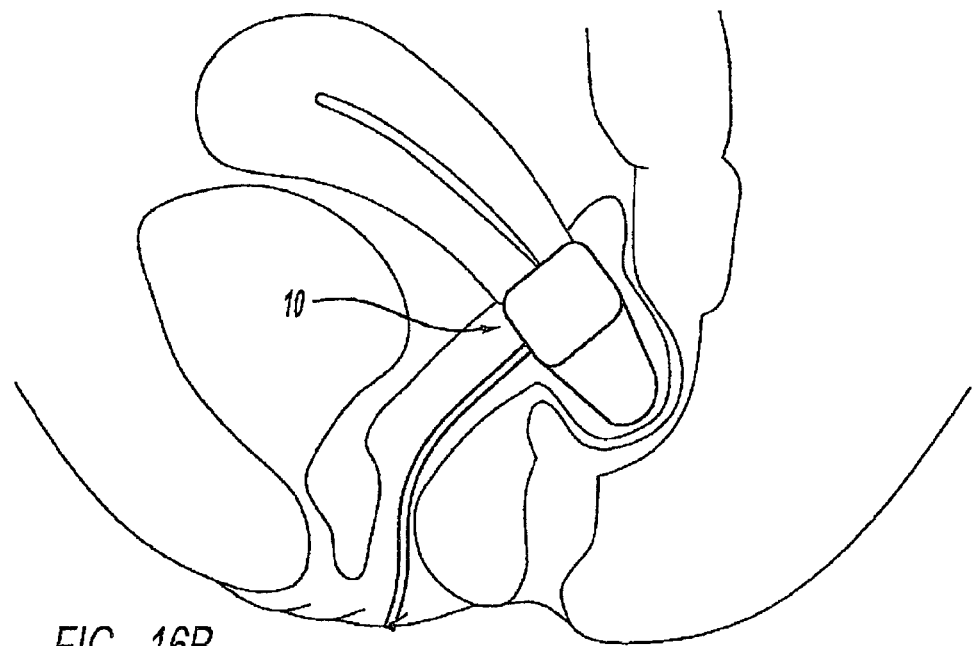
*FIG - 16B*
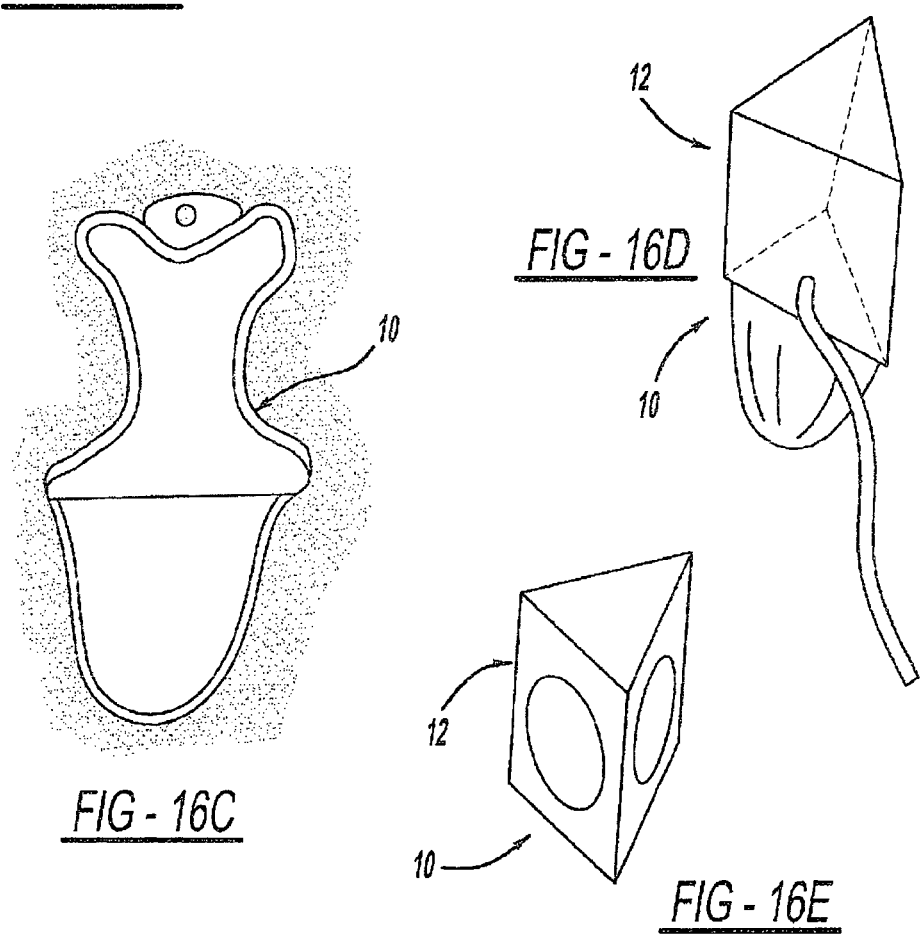
*FIG - 16C*
*FIG - 16D*
*FIG - 16E*

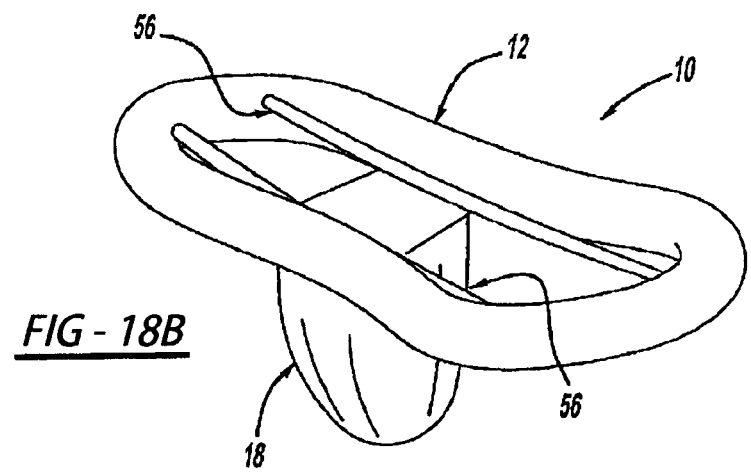
FIG - 18B
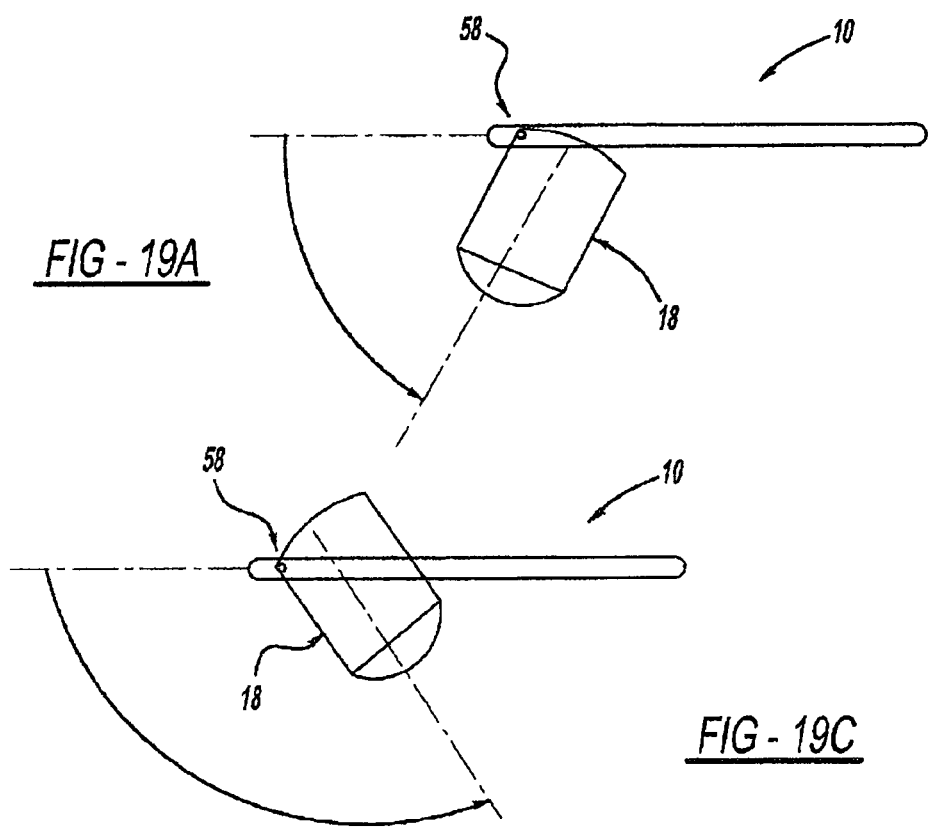
FIG - 19A
FIG - 19C

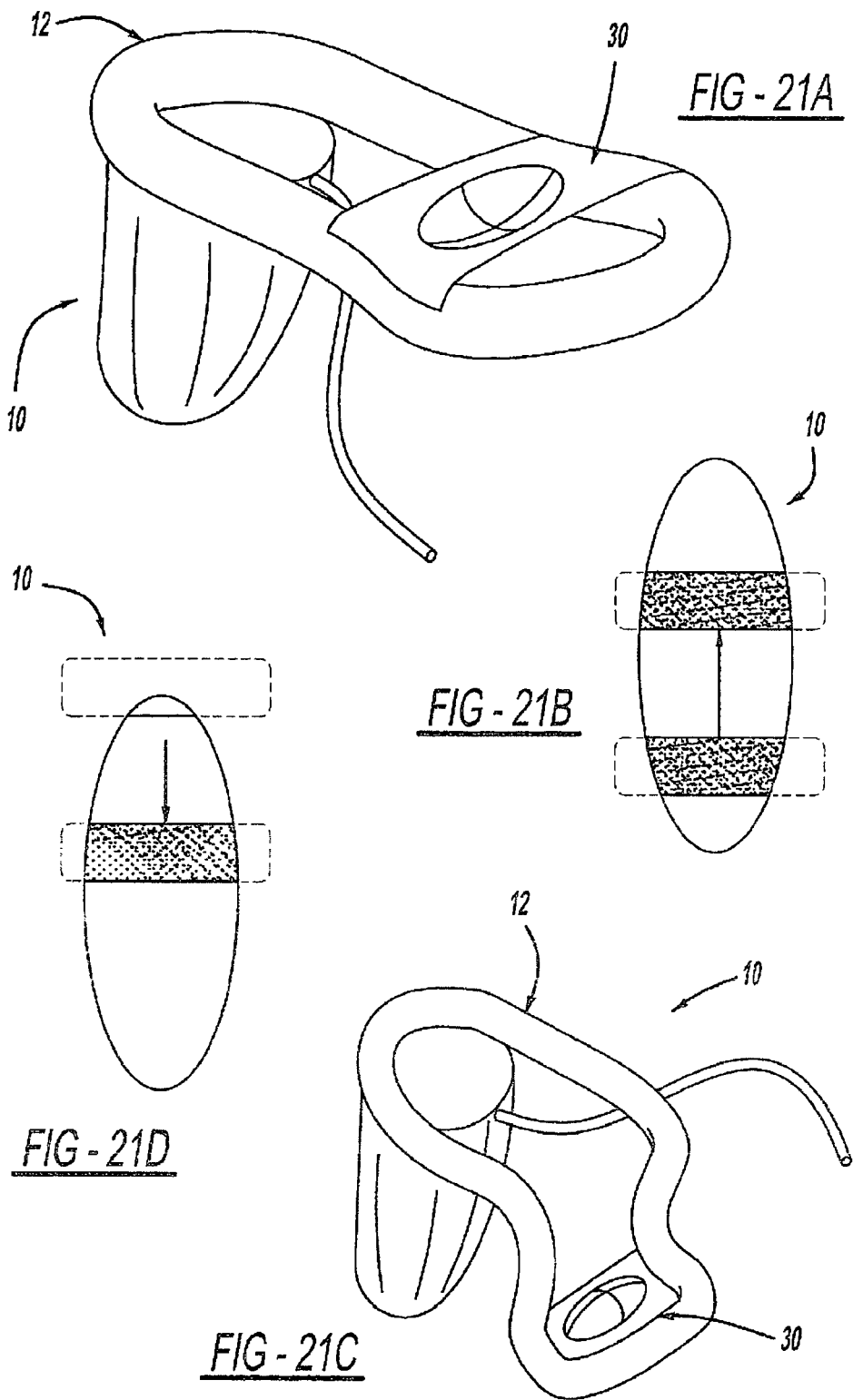

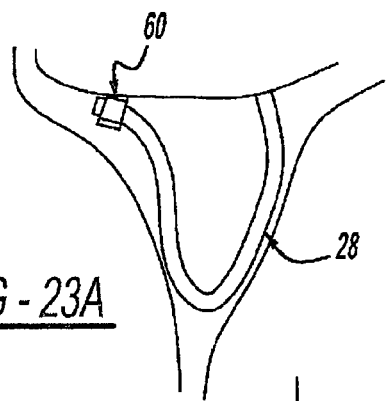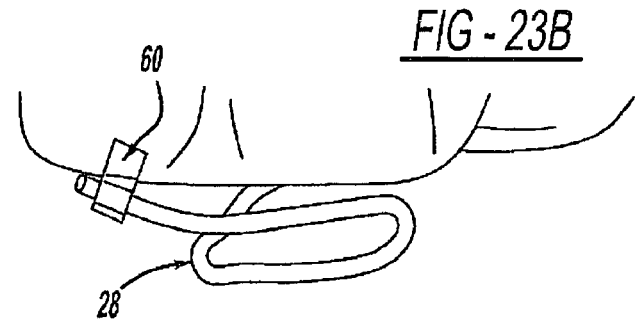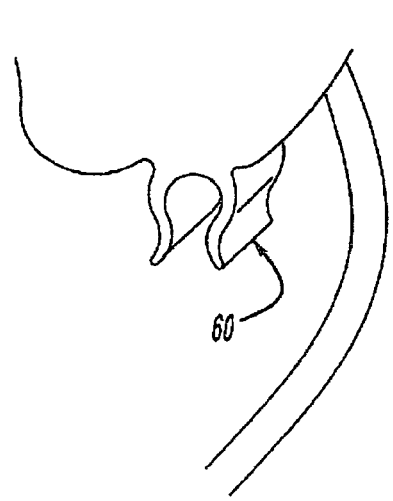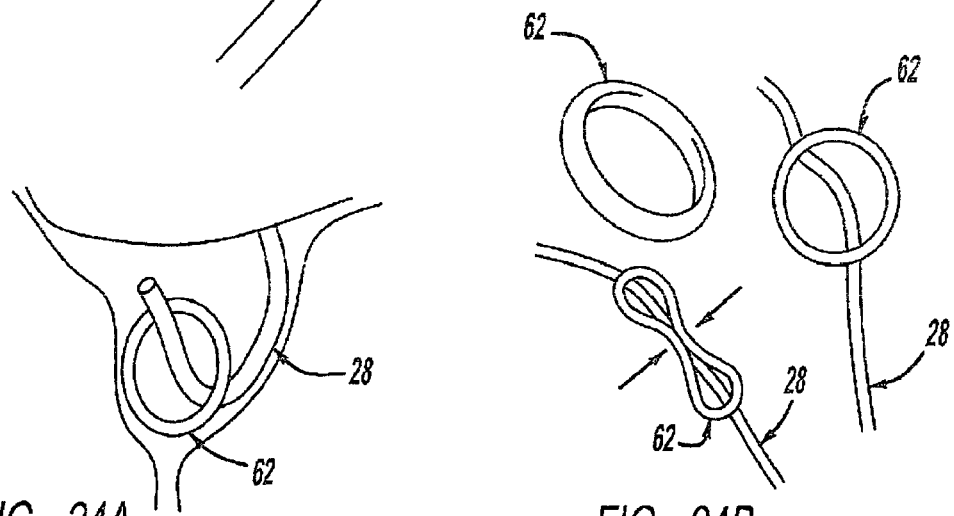
FIG - 23A
FIG - 23B
FIG - 23C
FIG - 24A
FIG - 24B

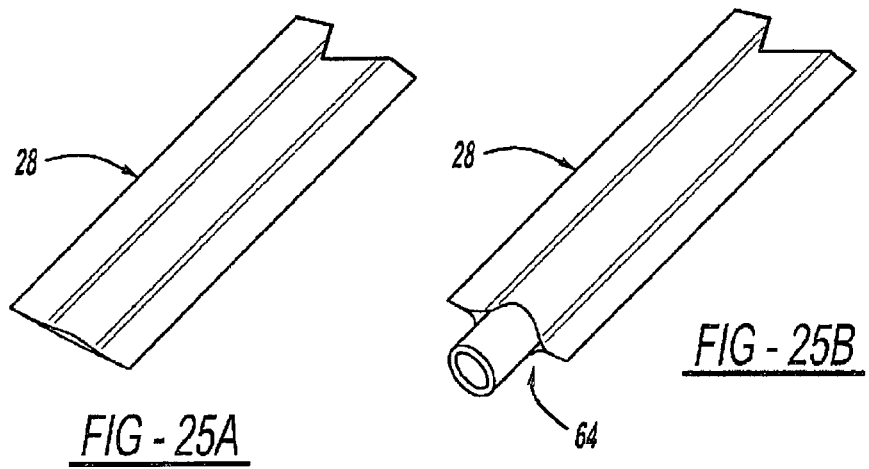
FIG - 25A
FIG - 25B
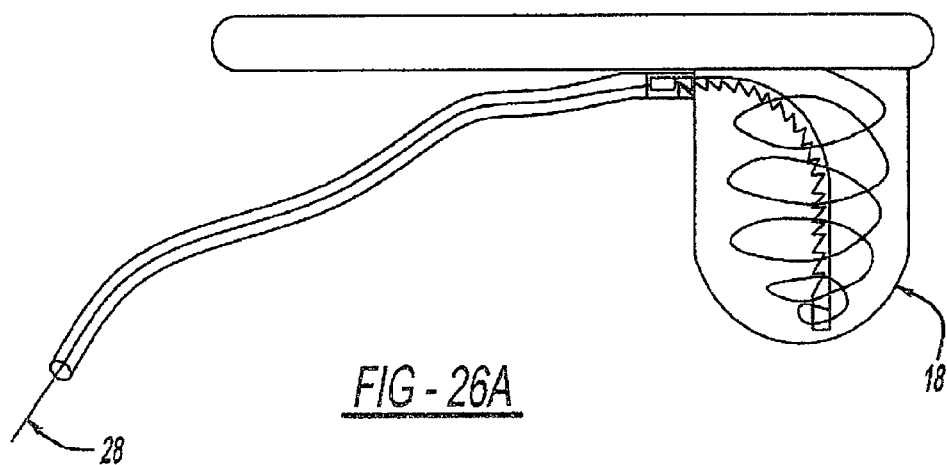
FIG - 26A
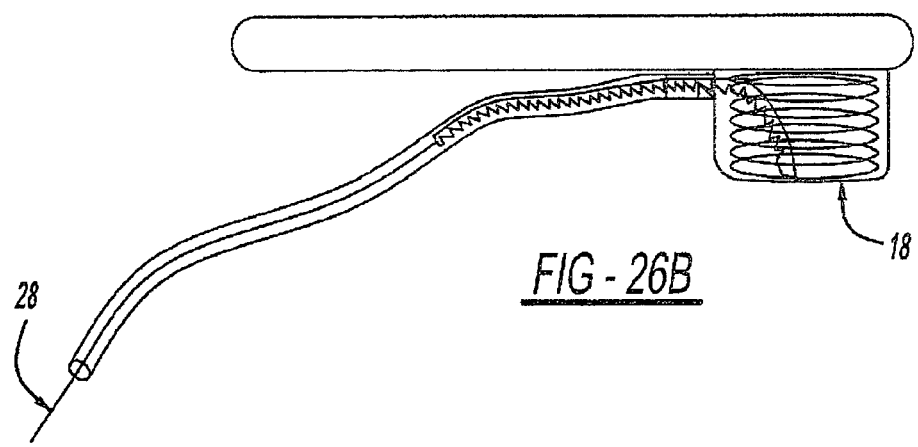
FIG - 26B

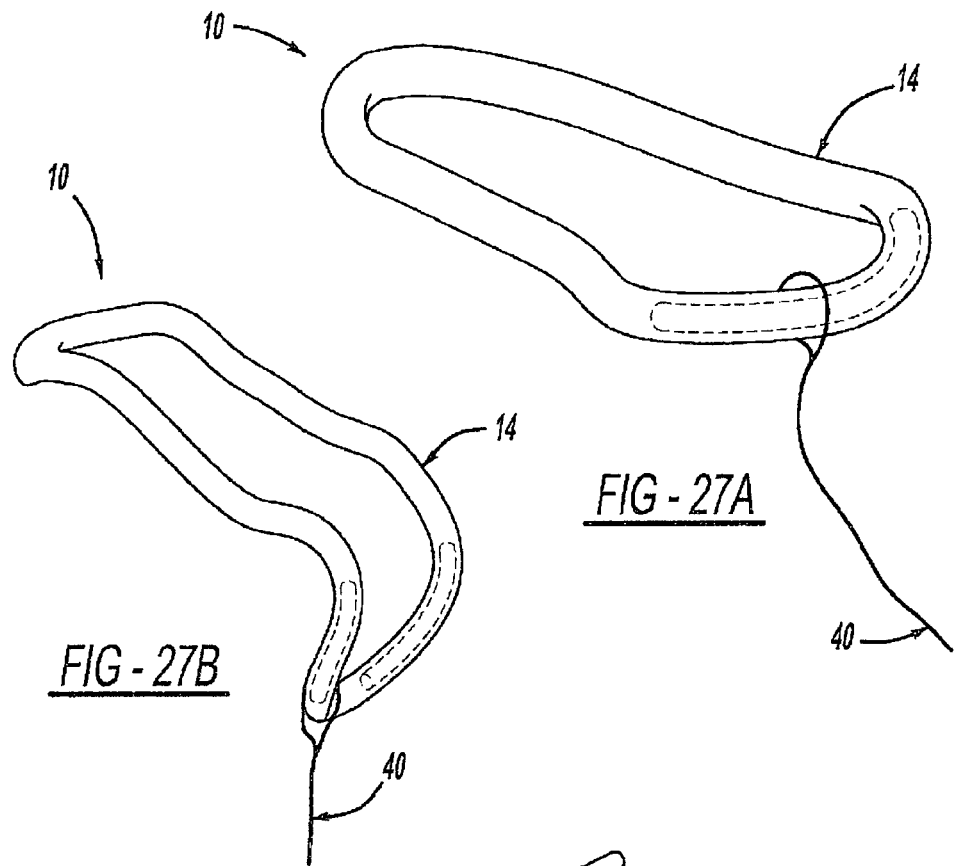
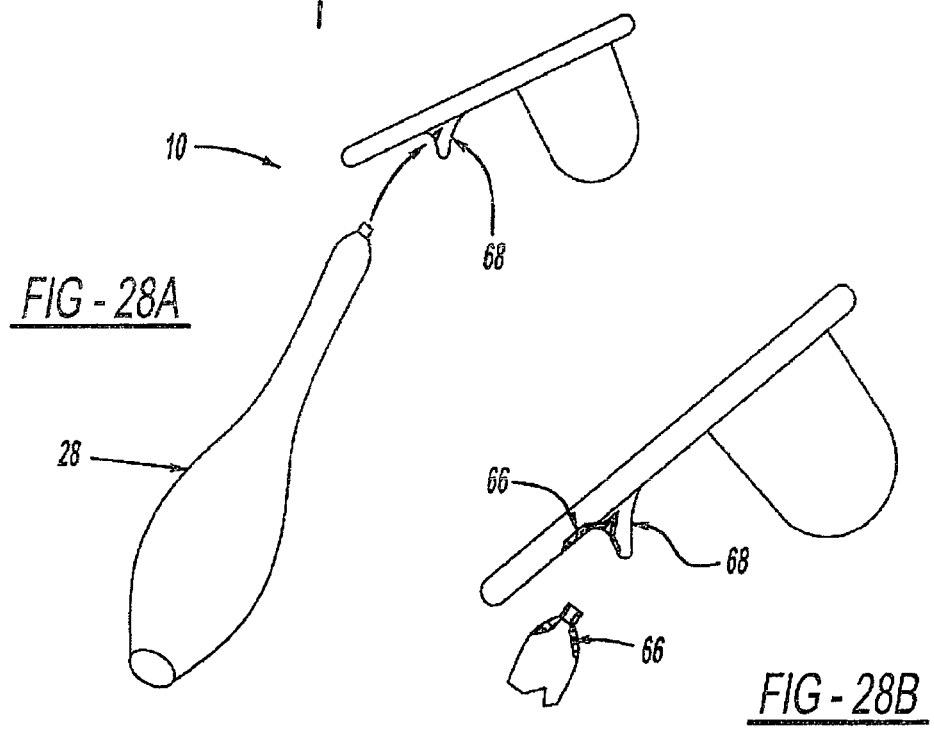

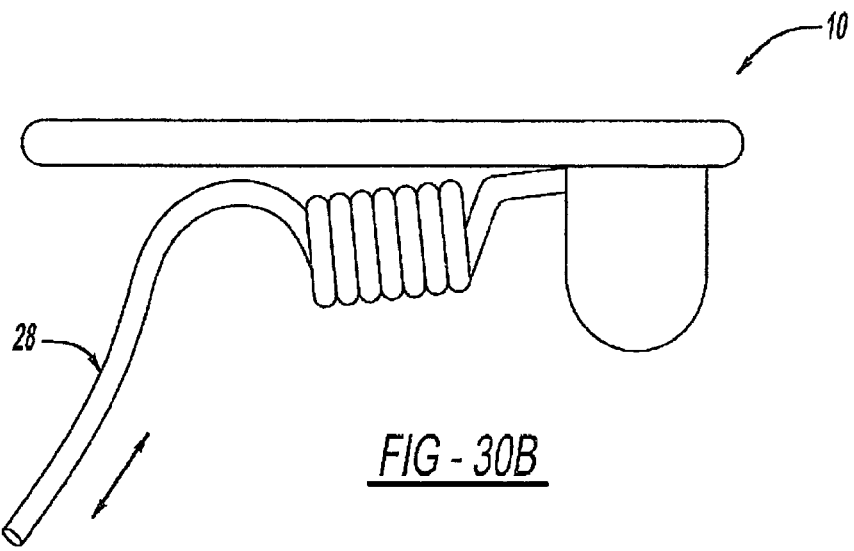
FIG - 30B
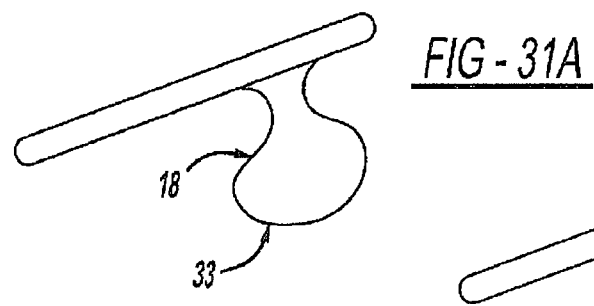
FIG - 31A
FIG - 31B
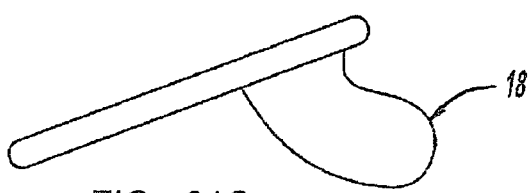
FIG - 31C
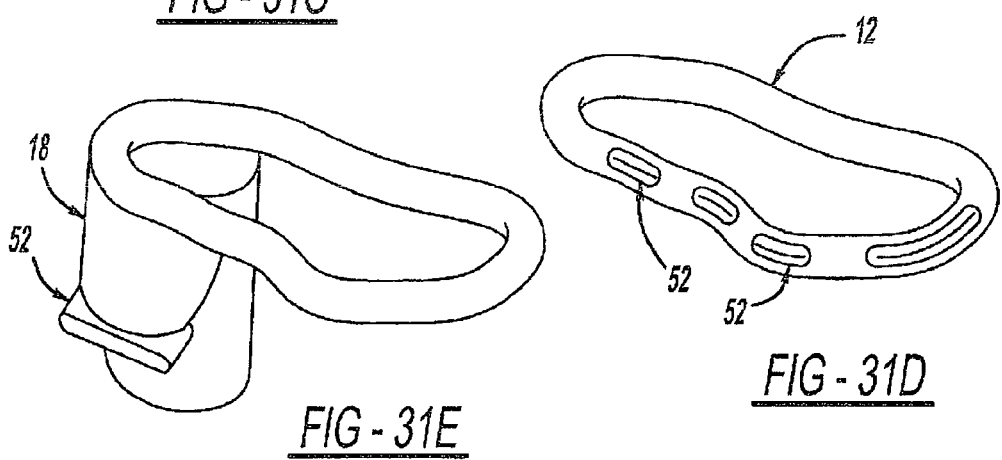
FIG - 31E
FIG - 31D

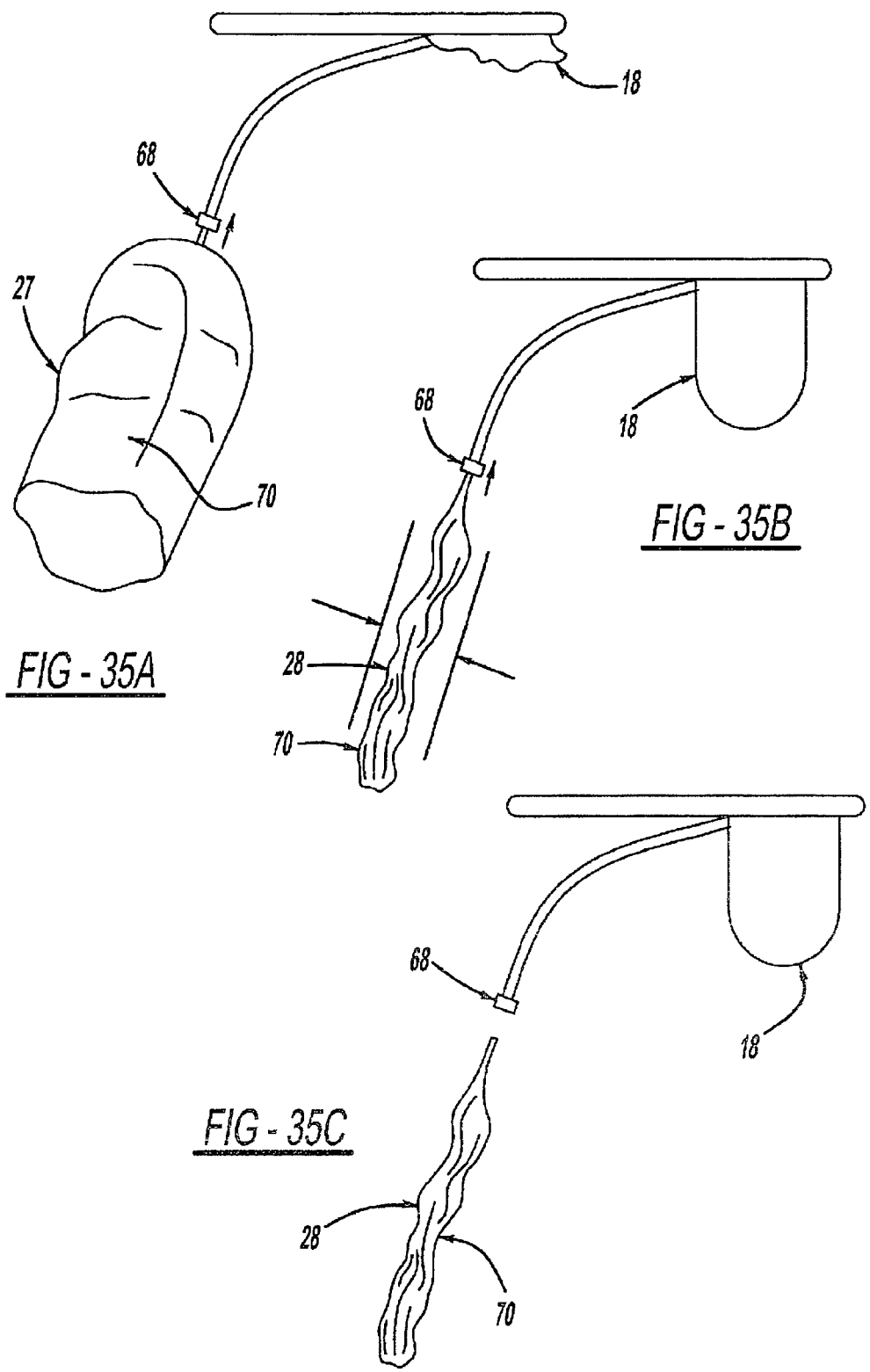

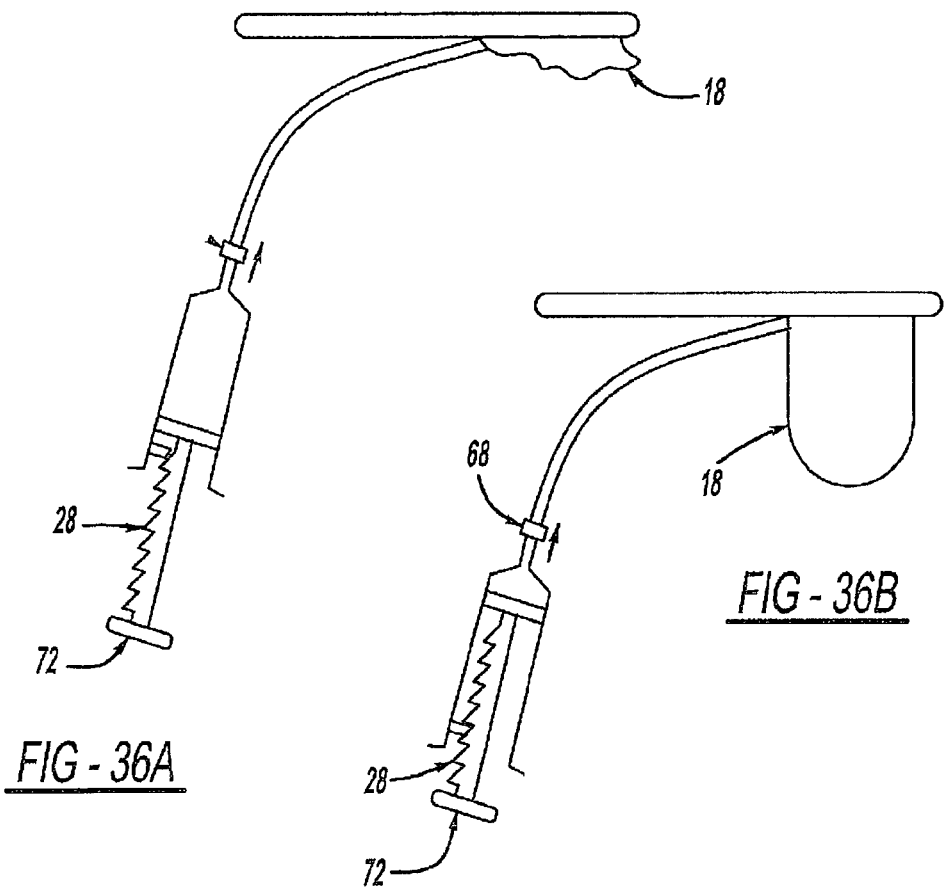
*FIG - 36A*
*FIG - 36B*
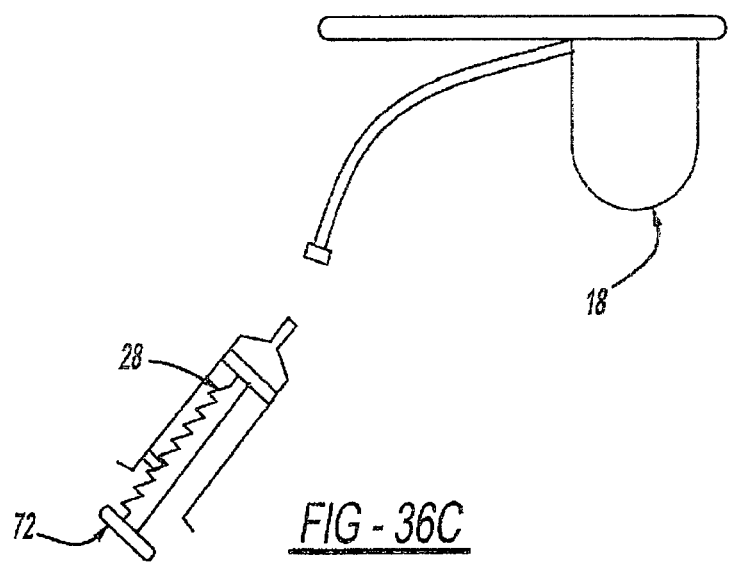
*FIG - 36C*

INTRA-VAGINAL DEVICE FOR FECAL INCONTINENCE

CROSS-REFERENCE TO RELATED APPLICATIONS

This application is the U.S. National Phase of International Application Ser. No. PCT/US2011/028691, filed on Mar. 16, 2011, which claims the benefit of U.S. Provisional Application Ser. No. 61/367,418, filed on Jul. 25, 2010 and U.S. Provisional Application Ser. No. 61/314,335, filed on Mar. 16, 2010.

TECHNICAL FIELD

The present invention relates to intra-vaginal devices. More specifically, the present invention relates to intra-vaginal devices for the control of stool passage.

BACKGROUND OF THE INVENTION

Fecal incontinence (FI), or the inability to control bowel movements, is an immense unmet clinical need, especially among women, who are 9 times more likely to suffer from the disease than men. While stigma surrounding the disease has masked the prevalence of the condition for decades, recent community-based studies estimate that up to 17 million women suffer from FI in the U.S. alone. The disease is psychologically and emotionally devastating, causing those afflicted to avoid going out in public and greatly reducing their quality of life. With no good treatments, most patients are left to cope with the disease wearing diapers.

Prevalence rates are higher in women because of the trauma caused to the pelvic floor during pregnancy and child delivery. Contributing pathophysiologies include damage to the external or internal anal sphincters, the pudendal nerve, the levator ani, and other muscles in the pelvic floor. This damage can immediately result in symptoms, or symptoms can not manifest until later in life. The latter is due to the fact that as this population ages, they experience age-related decreases in general continence mechanisms, such as changes in rectal sensation, compliance, and volume, in addition to further weakening of the sphincters and pelvic floor muscles. The average age of onset of symptoms is surprisingly young—51 years of age.

Many women with FI have multiple defects in their continence mechanisms, making it a very difficult condition to treat. This is one of the reasons why many treatments have previously failed, as they only work to address a single cause (e.g. sphincter tears or nerve damage). Conservative attempts to control fecal incontinence, including dietary changes and physical therapy have been largely unsuccessful.

More invasive approaches have been tried to statically reduce the size or change the angle of the anorectal canal. Such approaches include: injectable bulking agents—a substance that gets injected into the walls of the canal; sphincteroplasties—a surgical method of tightening the sphincter; and rings and slings—devices placed partially or all the way around the rectum. Such treatments have shown poor results, likely because they are fundamentally static devices and cannot achieve a dynamic and controllable function like a healthy sphincter. Devices such as American Medical System's Acticon Neosphincter address this problem by functioning as an artificial sphincter that the patient can control. The neosphincter consists of a cuff placed around the rectum, a patient-controlled pump implanted in the labia, and a reservoir implanted in the abdomen. Such devices have better dynamic range, but their invasive nature has led to infection, erosion, and removal rates. As a result, very few such procedures are performed. Therefore, a great need exists for a dynamic treatment to fecal incontinence that is not invasive.

U.S. Patent Application Publication No. 20060211911 to Jao, et al. discloses a vaginal insert having a cylindrical front projection 11 and a head 20 at the rear end thereof for holding by a person's hand. In use, and as shown in FIG. 6, the person holds the head 20 and then inserts the cylindrical front projection 11 into the vagina 30 to push the rectovaginal septum 50 outward against the rectum 40, thereby guiding accumulated excrement 70 back to the rectum 40. The Jao, et al. device generally aids in the passage of stool, not prevention of stool passage. It demonstrates that rectal contents can be controlled intra-vaginally. However, it discusses nothing that would occlude the rectum to prevent stool. It also does not discuss something that would stay in the vagina in order to control stool passage. Further, it discusses nothing that could fit stably in the vagina in order to control the rectum.

U.S. Pat. No. 6,013,023 to Klingenstein discloses a device for controlling fecal incontinence of a hollow, tubular member 1 defining a longitudinal cavity 2 that terminates in a closed proximal end 3 and an expandable sheath 6. Wings 13 can also assist in holding the device in place.

A major drawback of Klingenstein's device is the means provided for stabilizing the device, which is essential to carry out the desired functionality. Klingenstein describes wings external to the vagina, which would be uncomfortable and cumbersome for patients. He also describes device expansion as a means for securing the device. It was discovered in Applicants' cadaver studies, that an intra-vaginal device where securing relies on expansion is inherently unstable when the device is unexpanded. It was further discovered that when such devices transition from unexpanded to expanded states, their positioning and directionality is variable and unpredictable. This is especially problematic when the goal is to use the vaginal device to apply a directed force to the rectum. For one, if the device is inserted in an unexpanded state, it makes it difficult to reliably expand to apply a force on the right spot. Additionally, throughout the course of use, patients can wish to deflate, but not remove, the device for defecation or other activities when they feel active bowel control is not needed. In these cases, as is the case initially, the instability upon deflation would make it difficult to re-expand in the right position. An improvement to Klingenstein's device would be one that has a stabilization means that is intra-vaginal and does not rely on expansion of the device. This would allow comfortable, repeatable application of force to the same portion of a patient's posterior vagina.

Another drawback to the stability of Klingenstein's device is that it is a tubular device, more specifically defined as generally cylindrical. Applicants' reduction to practice has revealed that this type of shape does not stably rest in the vagina, especially if force is applied towards the recto-vaginal septum, as it tends to rotate. An improvement to the art is a device designed to prevent rotation around the axis formed by the distal and proximal ends of the device, such that it can remain in the appropriate position to exert a repeatable force on the proper part of the recto-vaginal septum.

Another major drawback of Klingenstein's device is that it lacks body means to allow easy force transfer from the vagina to the rectum. Applicants' experimentation has revealed the importance of the availability of redundant vaginal tissue to maintain force on the rectum. If a device is not designed to allow redundancy (or slack) in the vaginal wall in the area where the force is transmitted to the rectum, then the tension in the wall makes it difficult to transfer the force posteriorly.

Klingenstein does not teach any art that would allow for such vaginal slack in the area where his device transmits force to the rectum. An improvement to the art would therefore describe a device that has a design to allow for sufficient slack to remain in the vaginal walls adjacent the force apply portion such that force is easily transmitted to the rectum.

There are a variety of pessaries in the prior art. These devices are usually indicated for the treatment of pelvic organ prolapse, in which they support organs, such as the uterus, from prolapsing into the vaginal canal. There are also other intra-vaginal devices in prior art for the purposes of birth control, urinary incontinence, and other conditions. These devices come in different shapes. Some have the ability to expand, but not in a directionally applied manner. None of these intra-vaginal devices are designed to be able to apply a directed force towards the rectum, let alone the ability to do so stably, repeatedly and with minimal force.

Therefore, there remains a need for a fecal incontinence device that can be inserted in the vagina and stably apply a force to the rectum in order to control the passage of stool. Such a device has not previously been conceived, and as a result there are no such devices in the market place and, more generally, no viable treatment for the millions of women suffering from fecal incontinence. Described below is a device for treating fecal incontinence, which explores the unique combination of stability and directed rectal occlusion.

SUMMARY OF THE INVENTION

The present invention provides for an intra-vaginal device for the control of stool passage, including a body mechanism for securing the device around the area of the pubic notch and in the area of the posterior fornix, the body mechanism including a force applying mechanism for reversibly applying a force to a posterior portion of the vagina to occlude the rectum.

The present invention provides for a method of controlling the passage of stool in a patient, by inserting an intra-vaginal device into the patient's vagina such that an anterior end rests around the pubic notch and a posterior end rests in the posterior fornix, exerting a force towards the posterior side of the vagina, preventing expansion of the patient's rectum with the force, impeding the passage of stool, and removing the force, allowing stool to pass.

The present invention provides for an intra-vaginal device, including a stabilizing body operatively connected to a rectal occluding member and including toggle means for toggling said occluding member between an occlusive and passive state.

The present invention provides for a method of controlling the passage of stool in a patient by inserting an intra-vaginal device into the patient's vagina, toggling an occluding member at the posterior end to an occlusive state, preventing expansion of the patient's rectum with the occluding member, impeding the passage of stool, and toggling the occluding member to a passive state, allowing stool to pass.

The present invention provides for an intra-vaginal device, including a stabilizing body for receiving an occluding member for controlling the passage of stool.

The present invention also provides for an occluding member for controlling the passage of stool, including a body and a securing mechanism for securing the occluding member to a dock on an intra-vaginal device.

The present invention provides for a method of controlling the passage of stool in a patient, by inserting a stabilizing body of an intra-vaginal device into the patient's vagina, inserting an occluding member in the vagina, docking the occluding member on the stabilizing body, preventing expansion of the patient's rectum with the occluding member, and impeding the passage of stool.

The present invention provides for an intra-vaginal device for the control of stool, including a stabilizing body including a force applying portion that produces minimal displacement adjacent to lateral walls of a patient's vaginal wall allowing for occlusion of the rectum by the force applying portion.

The present invention provides for a stabilizing mechanism for repeatably contacting a force applying portion with a same area of an anterior rectum wall, the force applying portion being able to apply force and impede the passage of stool through the rectum.

The present invention provides for an intra-vaginal device including a stabilizing mechanism for stabilizing the device to prevent rotation and translation in the vagina, thereby allowing a portion of the device to reversibly apply force to the same area of the rectovaginal septum to control stool movement through the rectum.

The present invention provides for a method of controlling stool movement through the rectum, by stabilizing an intra-vaginal device and preventing rotation and translation in the vagina, reversibly applying force to the same area of the rectovaginal septum with the device, and controlling stool movement through the rectum.

The present invention provides for an intra-vaginal device, including a stabilizing mechanism for stabilizing the device to prevent rotation and translation in the vagina in a first and second state, wherein when in a first state, force is not applied to the rectovaginal septum (RVS) and, wherein when in a second state, force is applied to the RVS thereby allowing a portion of the device to reversibly apply force to the same area of the rectovaginal septum to control stool movement through the rectum.

The present invention provides for a method of controlling stool movement through the rectum, by stabilizing an intra-vaginal device and preventing rotation and translation in the vagina when the device is in a first and second state, wherein when in a first state, force is not applied to the rectovaginal septum (RVS) and, wherein when in a second state, force is applied to the RVS, reversibly applying force to the same area of the rectovaginal septum with the device, and controlling stool movement through the rectum.

The present invention provides for a device including a stabilizing mechanism for stabilizing the device in a body orifice and a force applying mechanism for applying force to an orifice wall, the stabilizing mechanism imparting minimal tension on the walls of the orifice proximate the force applying mechanism, such that the force applying mechanism can displace the orifice wall.

The present invention further provides for a method of controlling flow of a substance through a body orifice, by stabilizing a device and preventing rotation and translation in the body orifice, reversibly applying force to the same area of the body orifice with the device, and controlling the flow of the substance through the body orifice.

BRIEF DESCRIPTION OF THE DRAWINGS

Other advantages of the present invention are readily appreciated as the same becomes better understood by reference to the following detailed description when considered in connection with the accompanying drawings wherein:

FIGS. 1A-1D are perspective, bottom, side, and front views of the intra-vaginal device;

FIGS. 4A-4E are top views of stabilizing body sizes;

FIGS. 6A-6D show the application of force to the expanding member, and FIGS. 6E-6F show the expanding member with a supportive member;

FIGS. 10A-10B are side views of the device with a spring in the expandable member;

FIGS. 11A-11B are side views of the device with a spring in the expandable member, FIGS. 11C-11D are side views of the device showing one method of operating the inflation mechanism, and FIGS. 11E-11F show views of the expandable member with reinforcements;

FIGS. 14A-14G are side views of a second embodiment of the device; and

FIGS. 15A-15G are views of a third embodiment of the device;

FIGS. 16A-16E are views of the device with grips or suction mechanisms;

FIGS. 18A-18B are perspective views of an adjustable expandable member;

FIGS. 19A-19D are views of the expandable member being adjustable angularly both in and out of the body;

FIGS. 21A-21D are perspective views and top views of the device;

FIGS. 23A-23C are views of latching mechanisms;

FIGS. 24A-24B are views of attaching mechanisms for maintaining the inflation mechanism in the vagina;

FIGS. 25A-25B are views of the inflation mechanism as a tube;

FIGS. 26A-26B are side views of a device with active contraction;

FIGS. 27A-27B are perspective views of the device with irreversible removal;

FIG. 28A is a side view of an external inflation mechanism, and FIGS. 28B-28D are views of the device with a mechanism for directing the inflation mechanism to a valve;

FIGS. 30A-30B are views of the device with a retractable inflatable mechanism;

FIGS. 31A-31C are views of different shaped expandable members, and FIGS. 31D-31G are views of the device with suction mechanisms;

FIGS. 35A-35C are side views of the device with a single use reservoir; and

FIGS. 36A-36C are side views of the device with a single use syringe.

DETAILED DESCRIPTION OF THE FIGURES

Figure 2A:
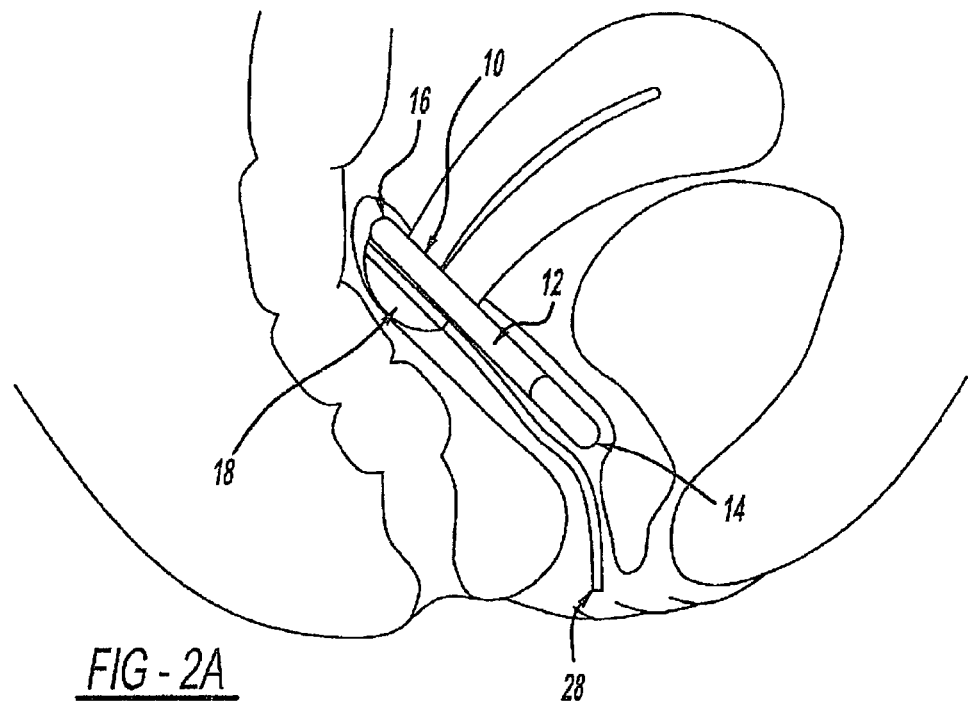
FIGS. 2A-2B are cross-sectional views of the body showing the position of the device.
Figure 2B:
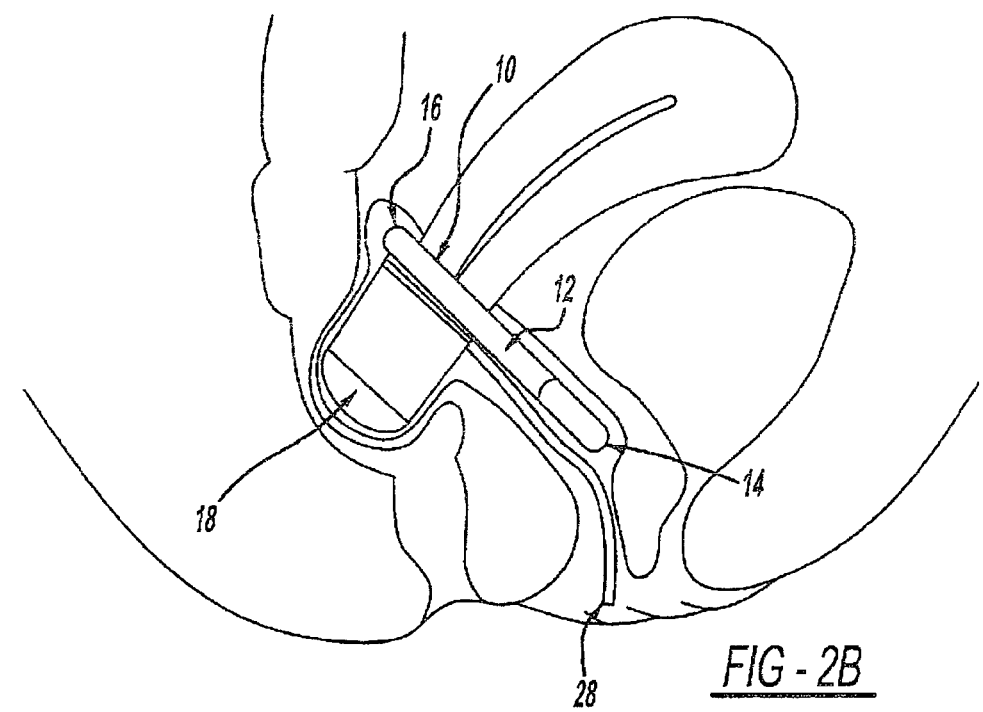

The present invention provides generally for an intra-vaginal device 10 that is used to control stool passage, generally shown in FIGS. 1A-1D. The intra-vaginal device 10 includes a stabilizing body 12 for securing the device around the area of the pubic notch and posterior fornix and for supporting a force-applying portion 18. The force applying portion 18 can reversibly apply a force to the recto-vaginal septum (the tissue separating the vagina from the rectum) which has the effect of inhibiting the passage of stool through the rectum. This force application can be as shown in FIGS. 2A and 2B, wherein the force application is made via a member expanding against the recto-vaginal septum.

Preferably, the device 10 is designed for the anterior region 14 to fit in the area of the pubic notch. The pubic notch is formed in the anterior vagina, resulting from the structure of the surrounding pelvic floor muscles, providing a stable anchoring point for the anterior end 14 of the device. Preferably, the posterior end 16 of the device 10 fits into the area of the posterior fornix. This is the deepest region of the vagina (i.e. the vaginal vault) behind the cervix. In patients without a cervix, e.g. those who have undergone a hysterectomy, the device still rests in the same area, which is the deepest extension of the vagina. A device designed to fit in this region has added security and stability. A more preferable embodiment is designed to fit in both of these areas to provide stability. A device designed for securing in the aforementioned locations will ensure that when placed properly, it rests outside of the region where the vagina is highly innervated, making the device comfortable for the patient. Additionally, the design of the preferred device, by engaging these locations, ensures easy repeatable positioning when the device is inserted, and further ensures positional certainty and stability such that when the device is inserted, it is in the correct position to apply force to the appropriate portion of the recto-vaginal septum, and can do so over multiple inflation/deflation cycles without the need for repositioning.

The force applying portion 18, is preferably an expandable member, and more preferably an inflatable member such as a balloon, though other mechanisms are considered below.

The inhibition of stool resulting from the application of force is due to the force the device applies to the rectum, which disallows the normal expansion of the rectal lumen, which normally occurs to accommodate stool. This action can be described as applying a force to deflect the recto-vaginal septum to compress the rectum, or as generally preventing the expansion of the rectum by applying a force to it. Alternatively, the force applying portion can reversibly apply a force against the vaginal wall opposite of the recto-vaginal septum, which would prevent stool passage by pressing the stabilizing body, or an additional expandable member, against the recto-vaginal septum.

The stabilizing body preferably includes a portion proximate to the force applying portion that has a narrow lateral span, such that when inserted, there is minimal distention of, and tension in, the walls of the vagina proximate to the force applying portion.

The stabilizing body 12, preferably has an anterior end 14 and a posterior end 16 operatively connected by a portion 20 or 12, which has a narrow lateral span and includes the force applying member 18, such that when inserted, the anterior end 14 preferably rests around the pubic notch and the posterior end 16 preferably rests in the posterior fornix of the vagina, thereby stabilizing and maintaining the position of the intra-vaginal device 10 while minimizing pressure or tension to the lateral walls of the vagina, as shown in FIGS. 2A and 2B. This portion of narrow lateral span can be considered as a central portion of the stabilizing body, or can also be considered as a posterior portion of the stabilizing body.

The preferred embodiment described above minimizes the imparting of tension in the lateral vaginal walls by having a narrow lateral span, especially in proximity to the force applying portion. In a more preferred embodiment, the width narrows from the anterior end 14 to the portion including the force applying portion 18 (FIGS. 1A and 1B), and also considered is a device that narrows from the posterior end 14 to the central portion (Insert FIG. 40A). Alternatively, the anterior end, 14 and the posterior end 16 can be connected by a more generally elongate portion, such as a rod (FIG. 8, item 12), thus avoiding pressure application on the lateral walls.

The width of the expandable portion can be 1-6 cm, more preferably 3-4 cm The length of the expandable portion can be 1-6 cm, more preferably 2-5 cm. The main body proximate to the expandable portion can be less than 7 cm and more preferably less than 5 cm in width to reduce tension in the vaginal walls.

Figure 7A:
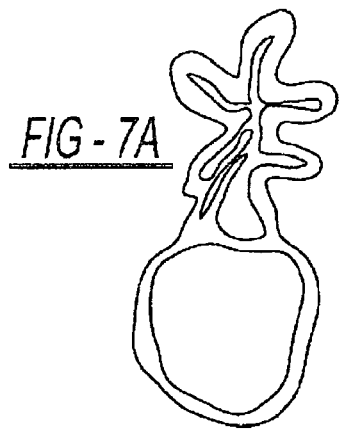
FIGS. 7A-7G show cross-sectional views of the vagina and rectum with the effect of vaginal displacement due to shapes of intra-vaginal devices.
Figure 7B:
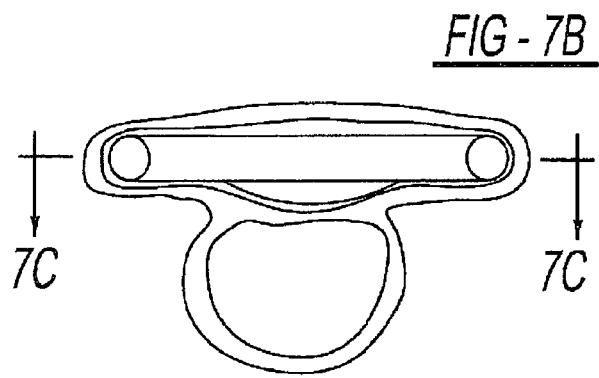
Figure 7C:
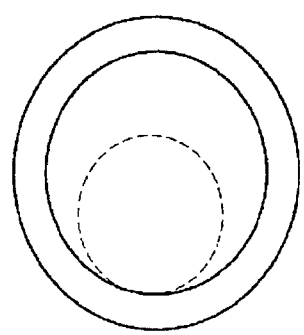
Figure 7D:
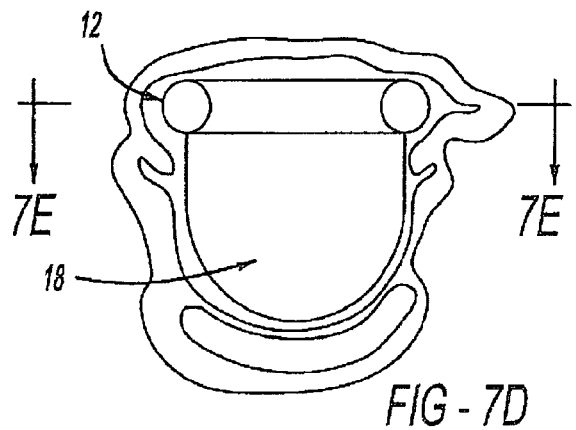
Figure 7F:
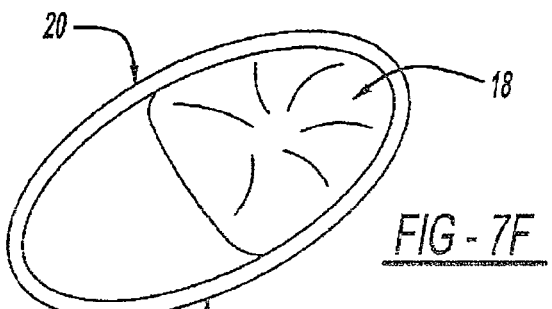
Figure 7E:
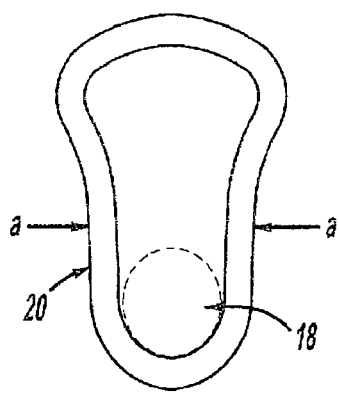

It is important that the intra-vaginal device 10 not utilize lateral distention of the vagina for fixation when applying pressure to the rectum to occlude stool. FIG. 7A shows a cross-section of the vagina and rectum, wherein the vagina has plenty of slack redundant tissue in folds along the wall. FIGS. 7B and 7C show an intra-vaginal device with a wider body that takes out the slack in the vagina walls, making it difficult to utilize the recto-vaginal septum to occlude the rectum. Since the device creates significant lateral distension on the adjacent wall, the wall loses its redundancy and elasticity and is not easily manipulated by the expandable portion. FIGS. 7D-E show the intra-vaginal device 10 of the present invention, wherein the device 10 takes advantage of the vaginal redundancy to push on the rectum. In other words, sufficient slack is still present in the vagina once the device 10 has been inserted, allowing the vaginal walls to be manipulated such that the rectum is occluded. This configuration allows stability and comfort while providing the function of occluding the rectum.

Therefore, the present invention provides for an intra-vaginal device 10 for the control of stool, including a main body 12 having an anterior end 14 and a posterior end 16, wherein the anterior end 14 and posterior end 16 are operatively interconnected by a portion or sides 20, which include a force applying member 18, such that the aforementioned portion or sides produce minimal displacement adjacent to lateral walls of a patient's vaginal wall allowing for occlusion of the rectum by the expandable member 18.

Figure 7G:
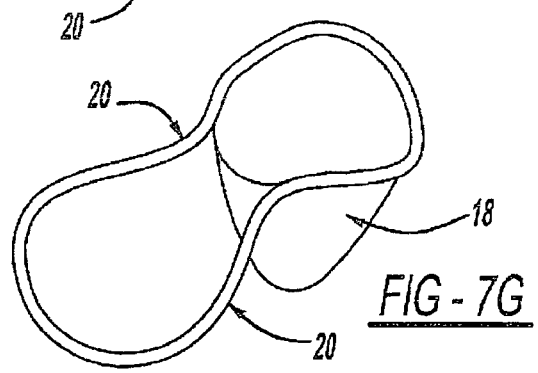

In order to further prevent lateral pressure on the vaginal walls, the sides 20 can laterally narrow when the expandable member is expanded. As shown in FIG. 7E, pressure "a" on the sides 20 when the expandable member expands can cause the sides 20 to narrow laterally. This is also shown in FIGS. 7F and 7G.

The stabilizing body 12 can also include extensions extending perpendicular to an axis formed by a line between the pubic notch and posterior fornix, wherein the extensions prevent rotation around the axis. The extensions can extend in a different direction as the direction of the force applying portion 18. The extensions can be perpendicular to the direction of said force applying portion 18. The stabilizing body 12 and the extensions can be a substantially planar structure.

The terms "occluding" or "occlude" as used herein, refer to restricting or obstructing the passage of stool through the rectum. The occlusion can be a full obstruction of the rectum, or it can be a partial obstruction. It is desired to prevent damage to the tissue separating the rectum from the vagina, herein referred to as the "recto-vaginal septum", so the recto-vaginal septum is not overly stretched, but merely held in place against, or displaced towards, the opposite side of the rectum and prevented from expanding in at least one direction to allow the normal passage of stool.

The term "toggling" or "toggle" as used herein, refer to the ability of an object (i.e. the occluding member 108 further described herein) to alternate between two or more positions. The toggling can be accomplished by mechanical or electronic mechanisms further described below.

Figure 3A:
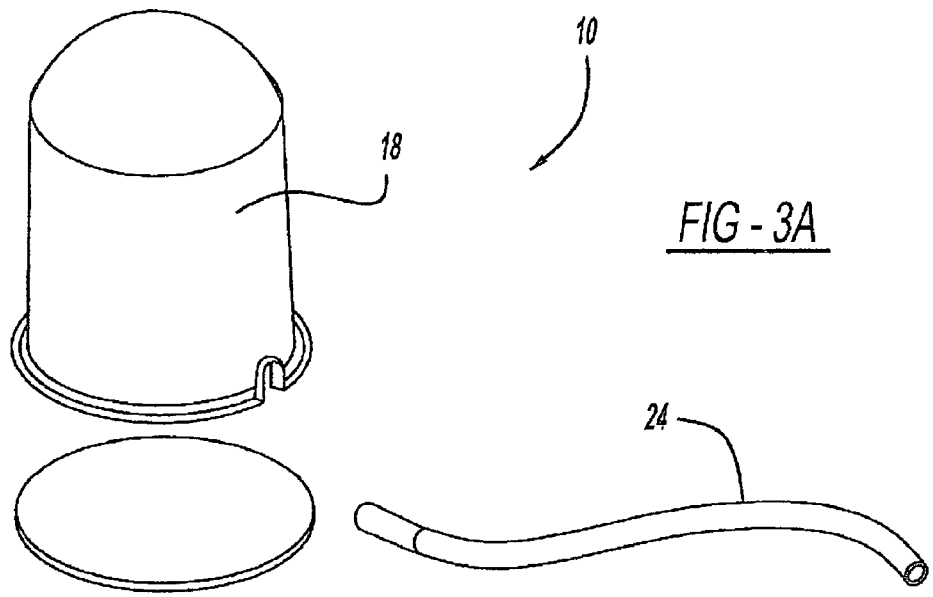
FIG. 3A is an exploded view of the device and FIG. 3B shows a folded device for insertion.
Figure 31F:
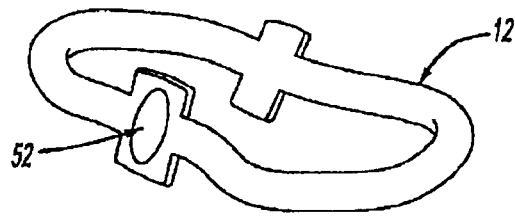
Figure 31G:
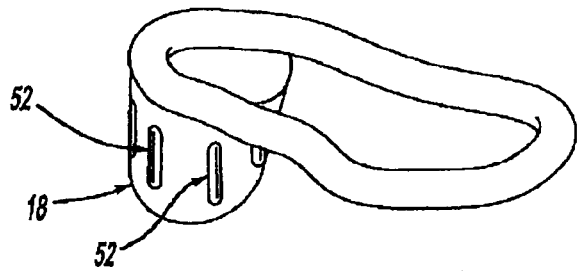

The stabilizing body 12 of the device 10 can be made of wire forms 22 enclosed in tubing 24, as shown in FIG. 3A. The wire forms 22 can be in any suitable configuration, but preferably, there is a wire form 22 for each side of central portion 20. In other words, preferably, the central portion 20 is two sides 20, but a single central portion 20 can be used. Any suitable wire can be used that will provide enough strength to maintain the shape of the device. Alternatively, a polymeric reinforcement can be used in place of, or in conjunction with, the wire forms. The tubing 24 is preferably silicon, but other materials can be used that are biocompatible. The surface of the stabilizing body 12 can include grips 52 on its surface in order to stabilize the device against tissue that it contacts. The grips 52 are small enough and shaped so that the tissue is not damaged or irritated by use. The grips 52 can also be a suction mechanism such as pocks that hold the stabilizing body 12 in place with a vacuum, as shown in FIGS. 31D, 31F. The stabilizing body 12 can also be inflatable, in order to help with insertion and removal.

In a preferred embodiment, the stabilizing body 12 is generally narrow, with the posterior end 16 being approximately of the same width as the force applying portion 18 and in a rounded shape, and the anterior end 14 being slightly wider and in a squared shape in order to fit securely around the pubic notch, and further so as not to unduly take out the slack in the vagina walls. The widened anterior end 14 can be a surface that is curved to approximate the curvature of the pelvic floor muscles interfacing therewith, shown in FIGS. 8K-8M. The roundness of the posterior end 16 also eases insertion and prevents irritation to the vaginal walls. The squareness (i.e. larger flat section before curving into the corners) of the anterior end 14 further helps in preventing the device 10 from rotating within the body. The lateral span of the portion 20 proximate to the force applying portion 18 can be slightly wider than a width of the force applying portion 18.

Figure 3B:
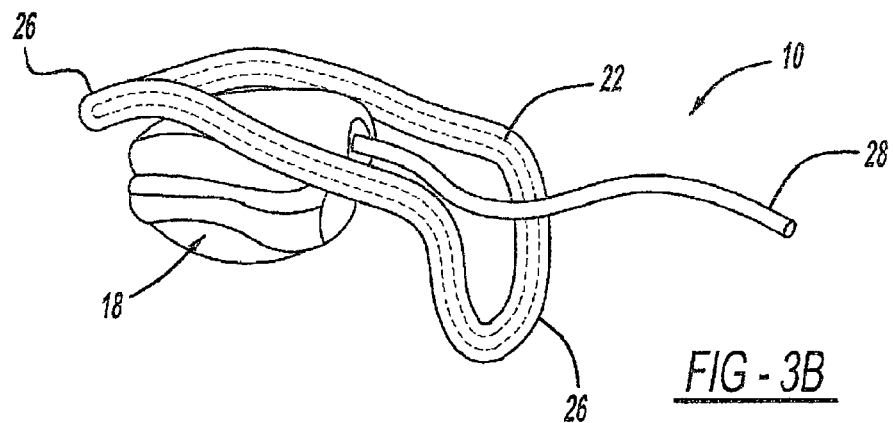

The anterior end 14 and the posterior end 16 preferably include springs 26, or other members that are at least in part flexible, that join the wire forms 22 in the stabilizing body 12 together. The springs 26 and the wire forms 22 can be operatively connected by any mechanism known in the art, including silicone, which can be overmolded over the wireforms. The springs 26 allow the device 10 to be folded along its length for easier insertion and return the device 10 to its open configuration once inside the vagina and in the preferred position around the pubic notch and in the posterior fornix. The springs 26 allow the device 10 to conform more naturally to the contours of the vagina. The springs 26 can also or alternatively be located between the anterior end 14 and posterior end 16 along the stabilizing body 12 such that the ends 14, 16 are decoupled from each other (as shown in FIGS. 20A-20G). The springs 26 further prevent force being imparted on one end 14, 16 from being directly transmitted to the other end 14, 16. For example, body forces due to the abdominal contents above the vagina, or forces due to a force applying portion 18 will have less of an effect on the stability of the anterior end 14 if they are connected by a flexible component. The wire forms 22 provide stiffness in the longitudinal direction. The folded configuration is shown in FIG. 3B. Alternatively, the stabilizing body 12 can also be made out of memory materials, alloys, or a contiguous flexible polymer that can return to an open shape after being folded for insertion.

The device 10 can be manufactured according to methods known in the art. For example, silicon adhesive or heat bonding can be used in assembly, or the device 10 can be injection molded as one single piece. The stabilizing body 12 can be glued together or heat melded, and the force applying portion 18 can be injection molded.

The stabilizing body 12 can also be manufactured in various sizes and shapes as shown in FIGS. 4A-4D. The central portion 20 of the device 10 can easily be shortened or lengthened to provide different sizes. The anatomy of every woman is different, and having various sizes and shapes available of the device 10 can allow for many different women to use the device 10. A suitable device 10 can be determined by a trial and error method of insertion. Alternatively, a CAT scan can be performed or X-rays taken, or other medical imaging technologies (ultrasound, MRI) to measure the dimensions of the vagina and rectum, in order to choose a preexisting device 10 or to custom manufacture the device 10 for a particular body. Additionally, specific tools such as a highly adjustable device or device proxy can be used to determine the correct size and shape for a given patient.

Figure 5A:
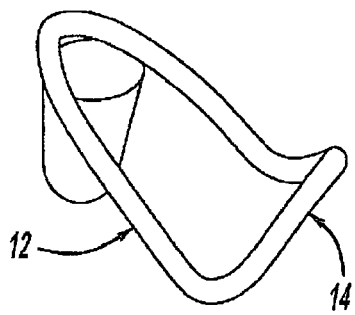
FIGS. 5A-I are views of various stabilizing body profiles.
Figure 5B:
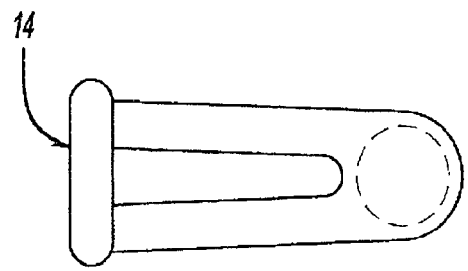
Figure 5C:
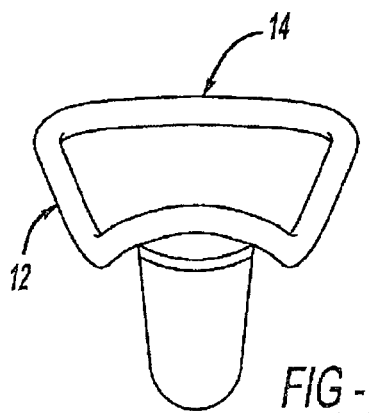
Figure 5D:
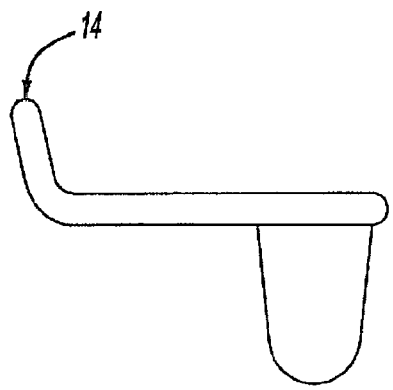
Figure 5F:
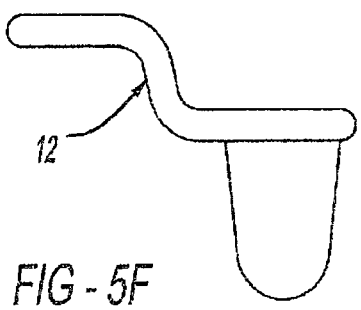
Figure 5G:
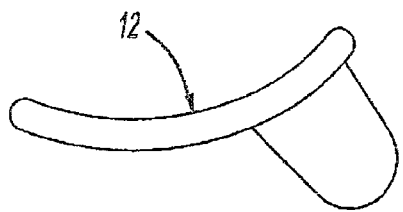
Figure 5I:
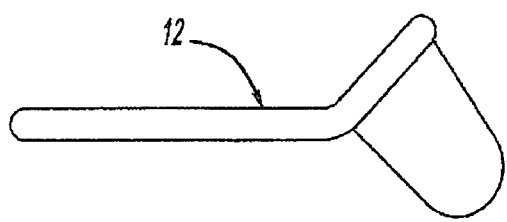
Figure 5E:
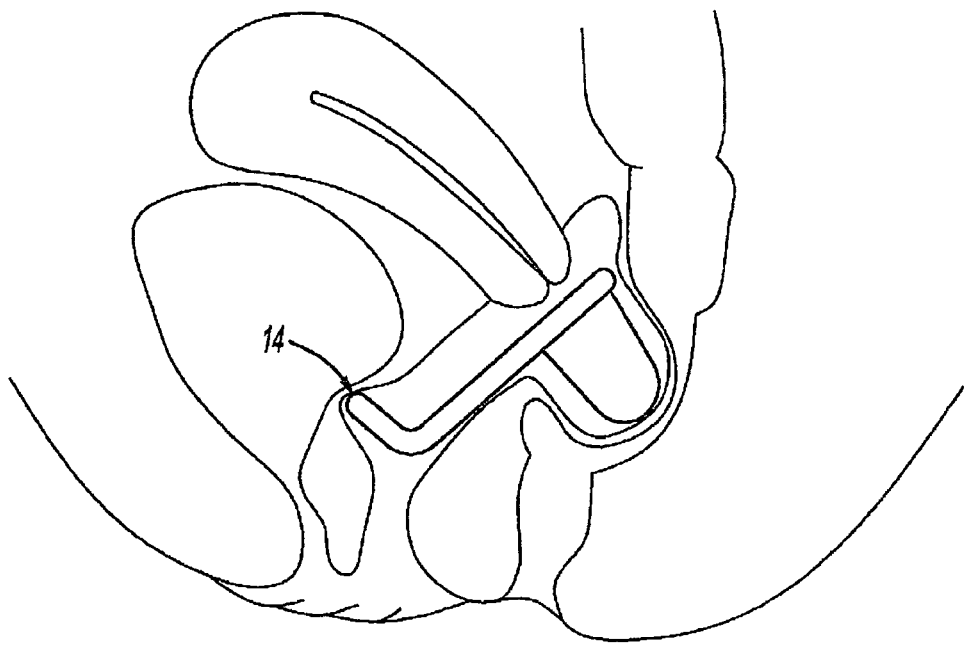
Figure 5H:
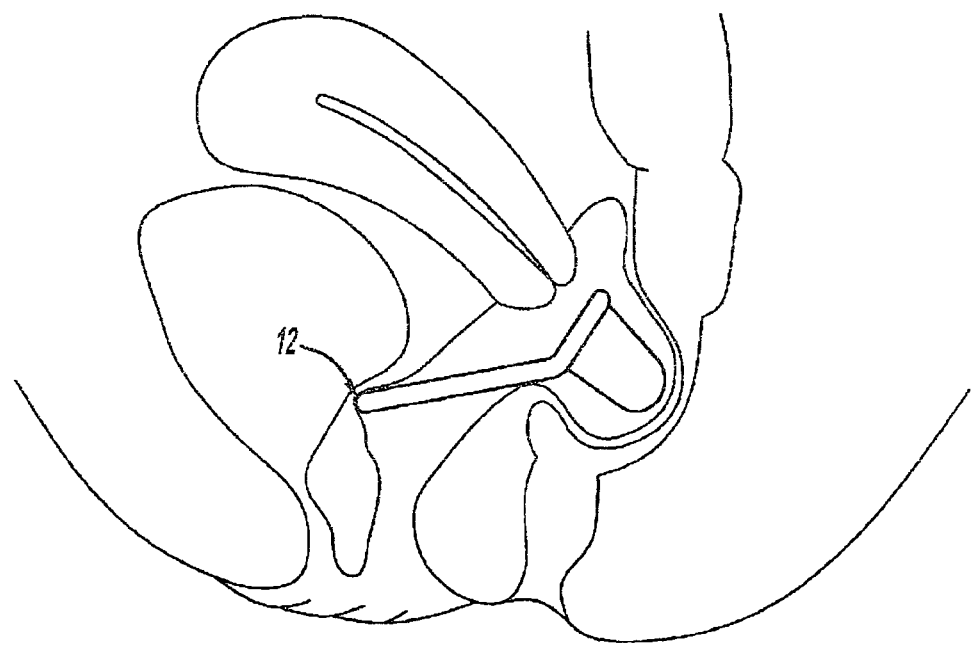
Figure 34A:
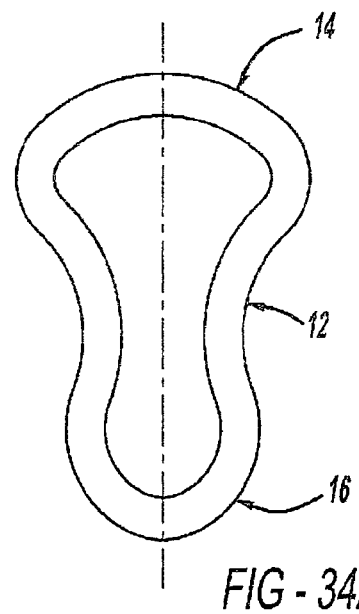
FIGS. 34A-34B show the line formed between the anterior and posterior ends.
Figure 34B:
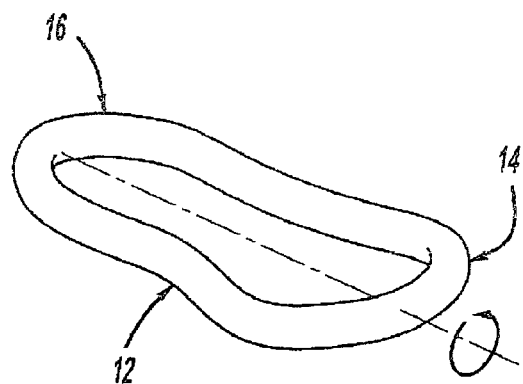

The stabilizing body 12 can also be not completely straight when viewed from a sagittal plane, but include an upward angled or curved anterior end 14 (FIGS. 5A-E), a stepped stabilizing body 12 (FIG. 5F), a bowed stabilizing body 12 (FIG. 5G), or an upward angled central portion of the stabilizing body 12 (FIGS. 5H-I). In other words, the stabilizing body 12 can include a portion that raises above the line formed by the anterior end 14 and the posterior end 16 (this line is shown in FIGS. 34A-34B). These different shapes of the stabilizing body 12 can aid in stability of the device 10 in different anatomies.

The force applying portion 18, preferably in the form of an expandable member 18 and referred to as such herein interchangably, at the posterior end 16 can be actuated between an expanded state and a contracted state in order to either prevent stool from passing through the rectum by pressing against the recto-vaginal septum and preventing the rectum from expanding to allow passage of stool (expanded state) or to allow stool to pass through the rectum (contracted state). The expandable member 18 is also preferably in the contracted state upon insertion, and can fold into the stabilizing body 12 and into itself for ease of insertion. However, the device 10 can also be inserted with the expandable member 18 at least partially expanded, and merely providing means for contracting the expandable member 18 (or allowing it to be compressed) to allow the passage of stool.

The expandable member 18 can be in various shapes and can include a domed portion that contacts the recto-vaginal septum. The expandable member 18 can be wider at a terminal end 33 opposite to where it attaches to the stabilizing body 12 (FIG. 31A), or can be narrow at its terminal end 33 (FIG. 31B). The expandable member 18 can be curved (FIG. 31C).

The expandable member 18 can be in the form of a balloon type portion. The balloon can have a permeability to allow for deflation over a pre-determined range of time. Other forms of the expandable member 18 can also be used. A surface of the expandable member 18 that contacts the vagina wall can include grips 52 for stabilization. The grips 52 are small enough and shaped so that they do not irritate or damage the tissue, and they can also be in the form of suctions as described above.

Figure 18A:
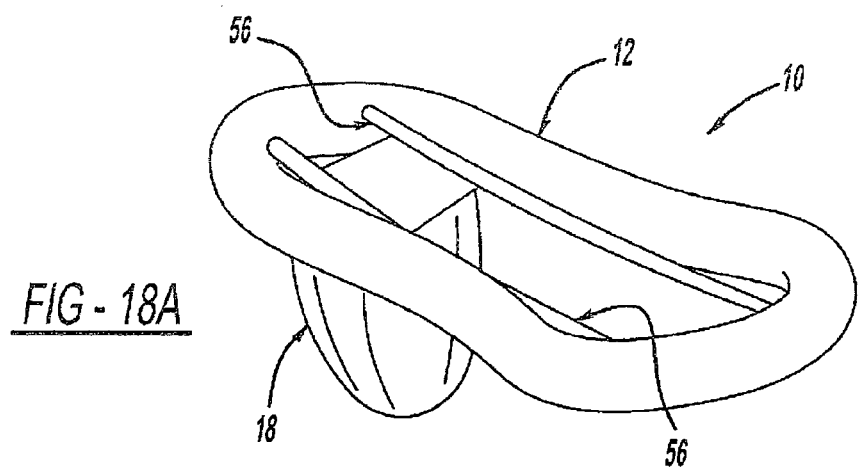
Figure 19B:
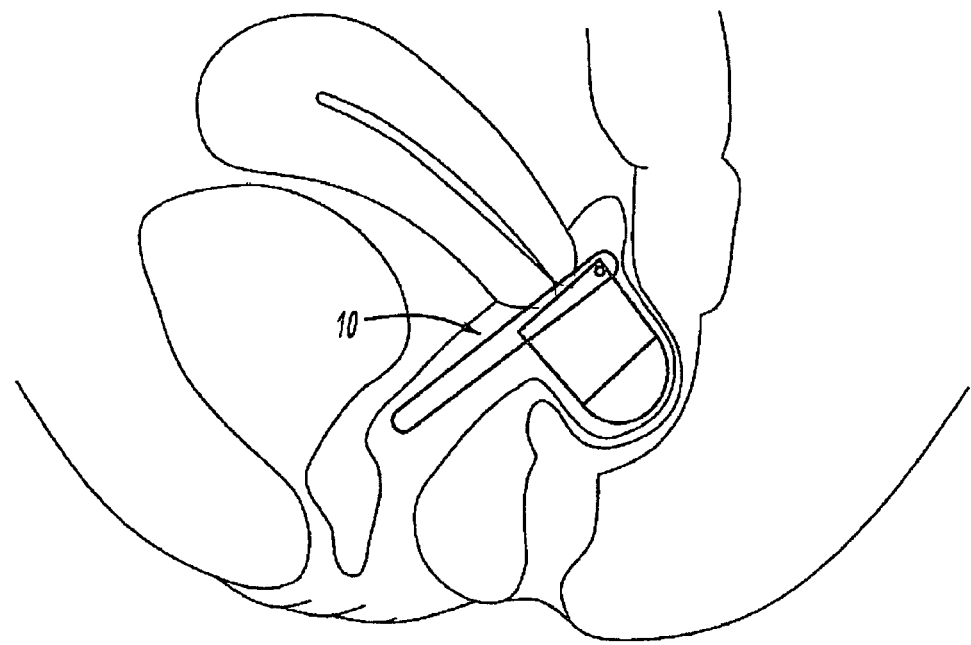
Figure 19D:
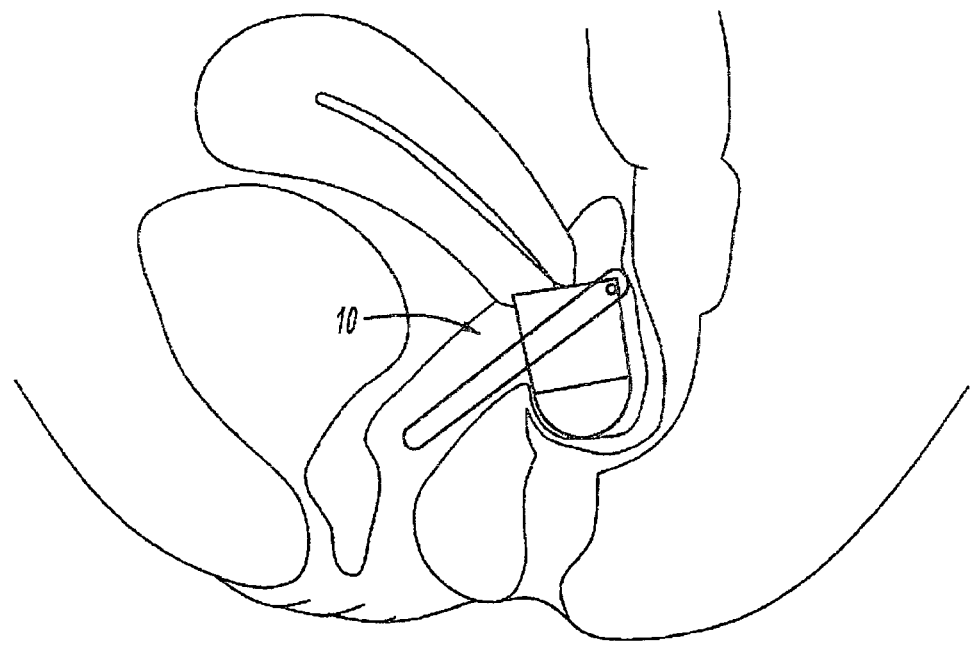
Figure 20A:
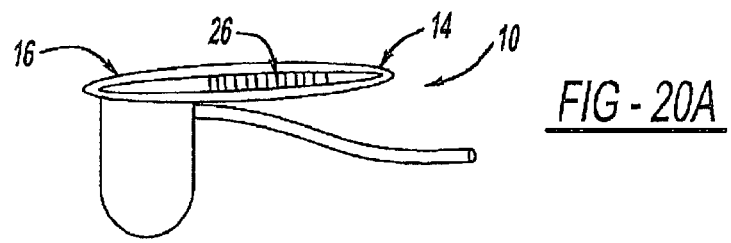
FIGS. 20A-20G are side views of the device wherein the anterior end and posterior end are decoupled.
Figure 20B:
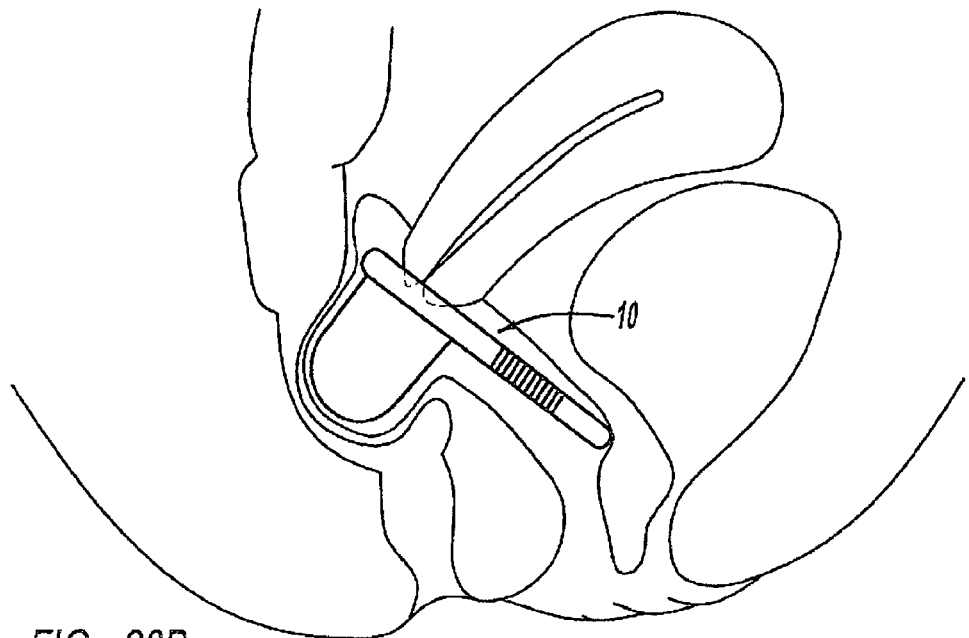
Figure 20C:
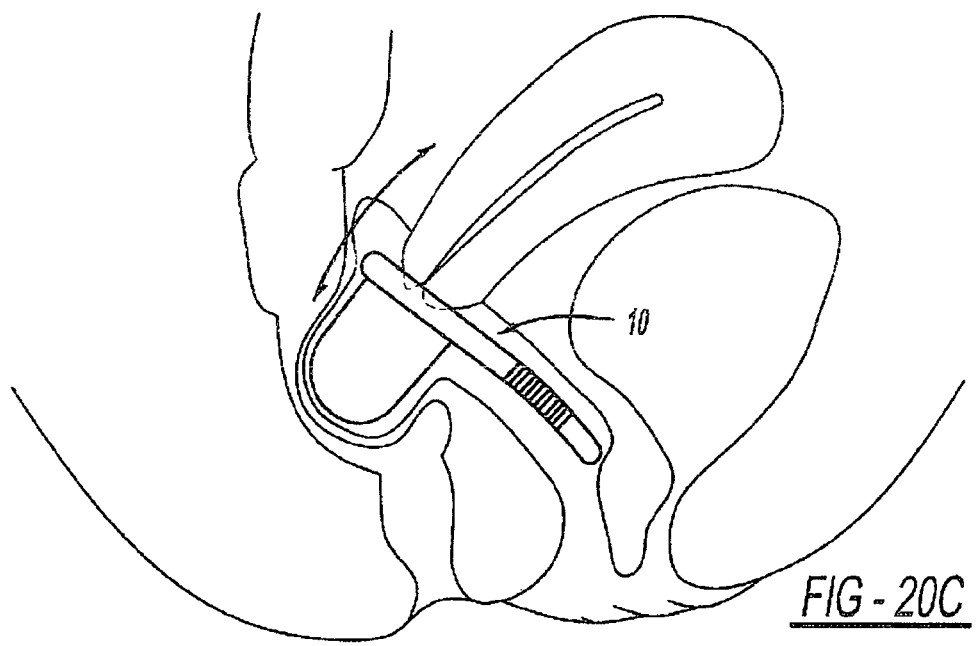
Figure 20D:
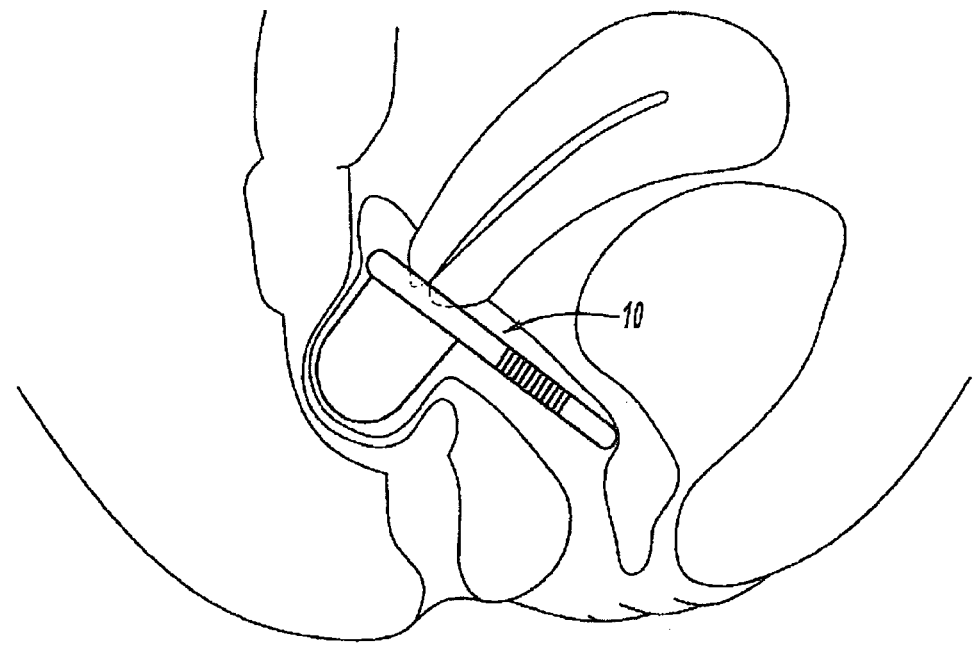
Figure 20E:
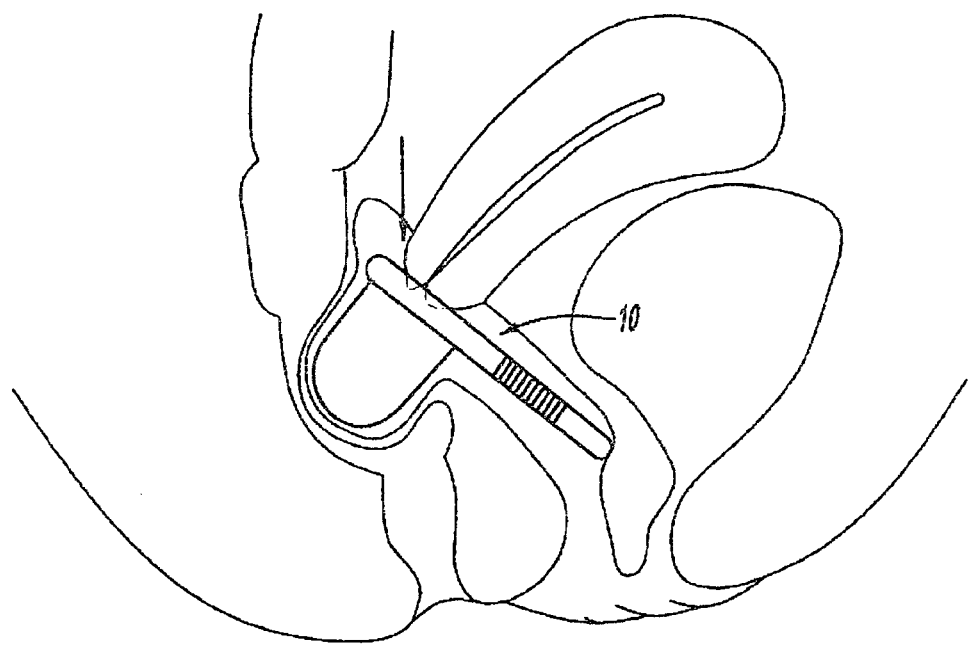
Figure 20F:
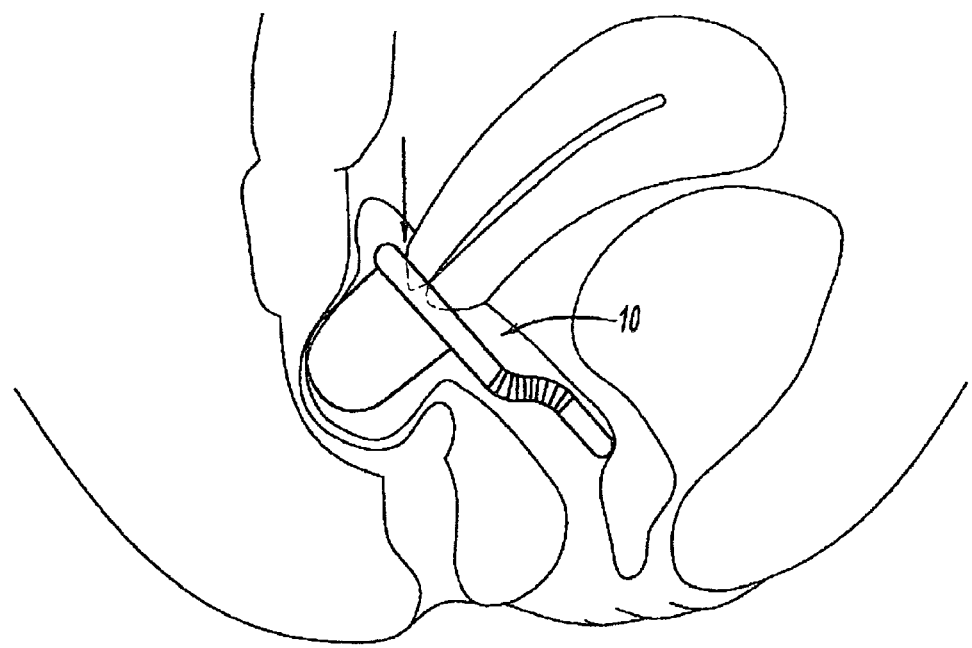
Figure 20G:
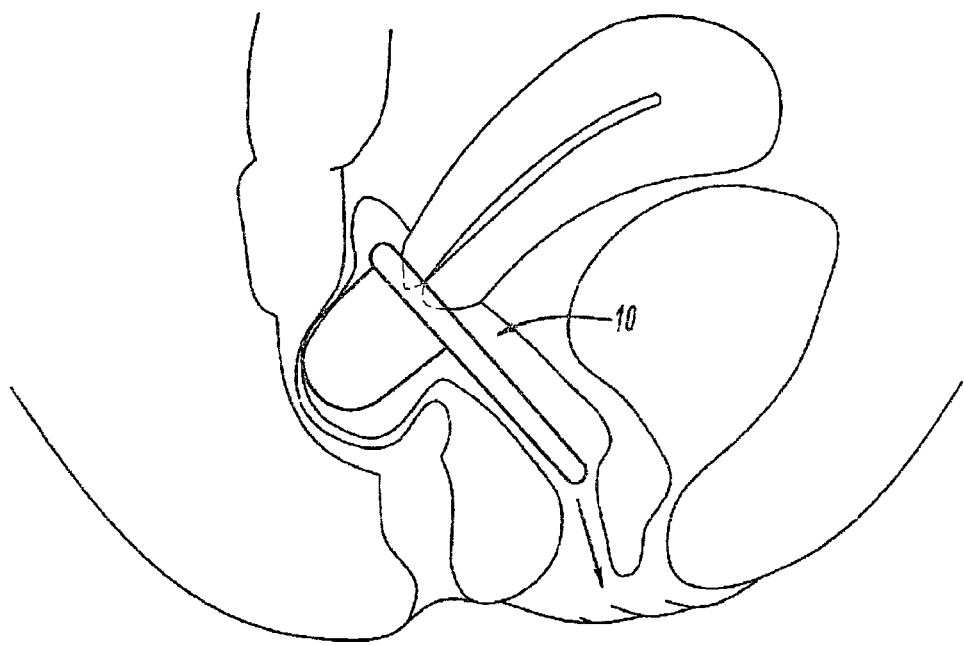
Figure 22A:
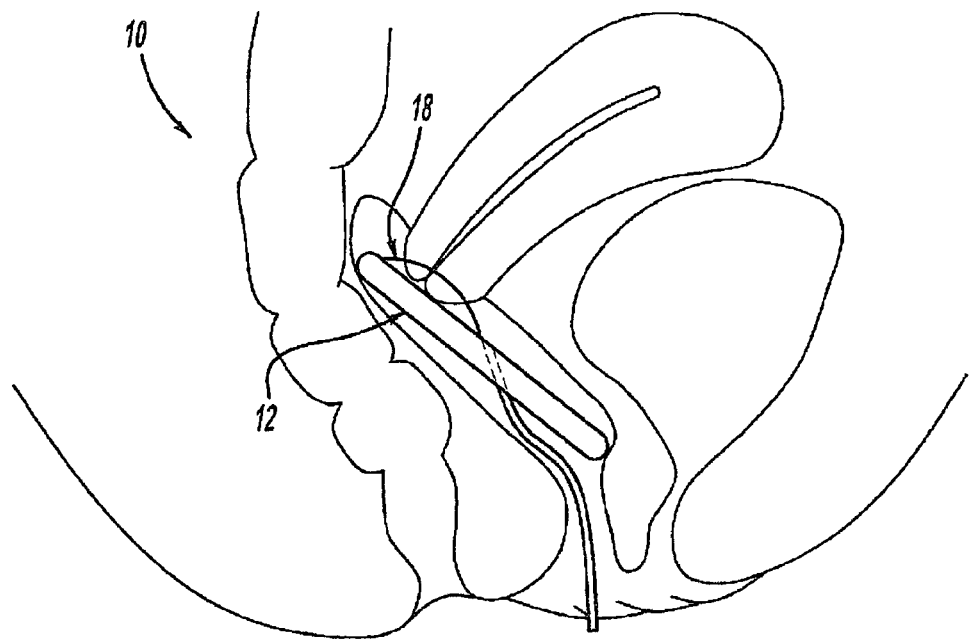
FIGS. 22A-22B are side views of the device wherein the expandable member 18 expands in an opposite direction.
Figure 22B:
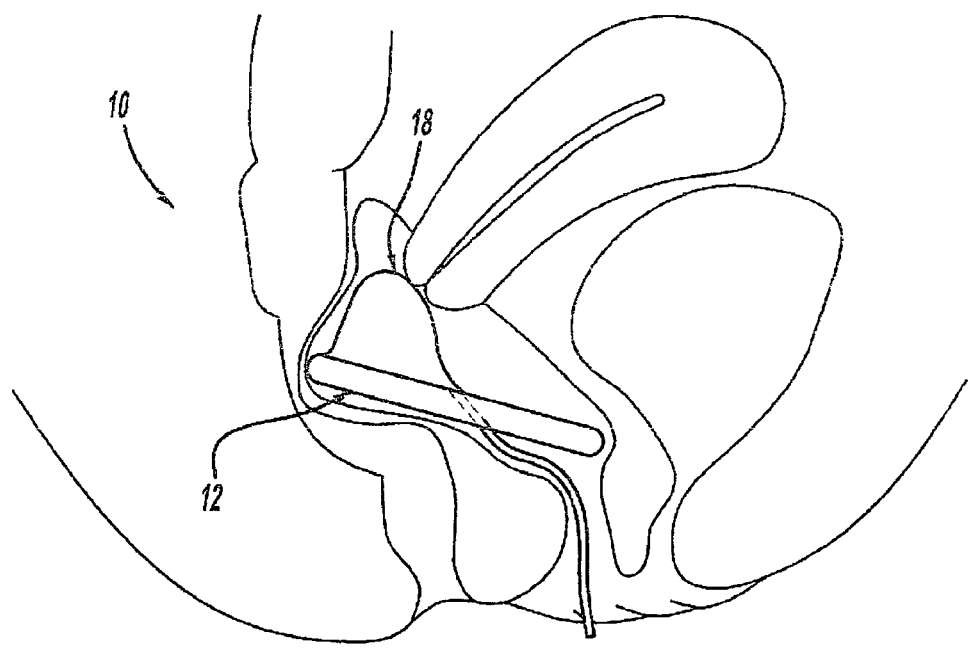

The expandable member 18 can also provide partial, but not total occlusion. It can not require total or complete occlusion to prevent fecal excretion. Upon occlusion, it is preferred that as much function of the rectum is left as possible, but that the most compliant area of the recto-vaginal septum is engaged and only that area by the expandable member 18. That is, the expandable member 18 should contact the rectum as low as possible to permit as much of the rectum to be functional for fecal storage, and yet it should contact the rectum high enough to provide effective contact to result in the occlusion. This location is preferably above the perineal body, which is bulkier and usually less compliant the recto-vaginal septum. Therefore, in order to provide the best positioning of the device 10, the expandable member 18 can be manufactured at different positions along the posterior end 16 or along various portions of the stabilizing body 12 in order to fit different anatomies. The expandable member 18 can also be manually adjustable along the length of the posterior end 16/stabilizing body 12, which the physician can adjust to fit a patient (FIGS. 18A-18B), with an adjusting mechanism 56. Preferably, the expandable member 18 extends from the stabilizing body 12 at a non-zero angle with respect to a line formed by the anterior end 14 and the posterior end 16. More preferably, the expandable member 18 contacts the rectum wall at a 45-135 degree angle. The expandable member 18 can be angularly adjustable with an angular adjustment mechanism 58 in order to ensure that it is targeting the appropriate part of an individual's anatomy, as shown in FIGS. 19A-19D.

An inflation mechanism 28 is included on the expandable member 18 for expansion and contraction (deflation), which can be reversible or irreversible. The inflation mechanism 28 can be permanently attached to the expandable member 18 and remain in the vagina or extend outside of the vagina (further described below) to expand and contract the expandable member 18. The inflation mechanism 28 and can be in the form of a tube (FIG. 25A-25B) that creates a leak when pulled that creates irreversible deflation. The tube can also be used with a tool 64 for widening the tube for emptying or filling the tube. Alternatively, the inflation mechanism 28 can be removably attached and can be attached only when the expandable member 18 needs to be expanded or contracted. The inflation mechanism 28 can include a flange at the end attached to the device 10, and located within the device 10, in order to prevent the inflation mechanism 28 from being pulled out of the device 10. The inflation mechanism 28 can be manually operated, such as by pulling on the inflation mechanism 28 to contract or expand the expandable member 18 (shown in FIGS. 11C and 11D), using a hand pump, reservoir, syringe, or it can be electronically operated by a remote control outside of the body. In this case, the expandable member 18 and device 10 include appropriate electronics. The inflation mechanism 28 can be a single use device that is thrown out after use. For example, the single use device can be an air-filled pouch or reservoir 70 that can only be compressed once to fill the device 10, shown in FIGS. 35A-35C, through a one-way valve 68. After inflation, the reservoir 70 is removed and the one-way valve 68 remains. Alternatively, it can be a locking syringe 72 that only compresses once through the one-way valve 68, shown in FIGS. 36A-36C. After inflation, the syringe 72 is removed and the one-way valve 68 remains.

Figure 29:
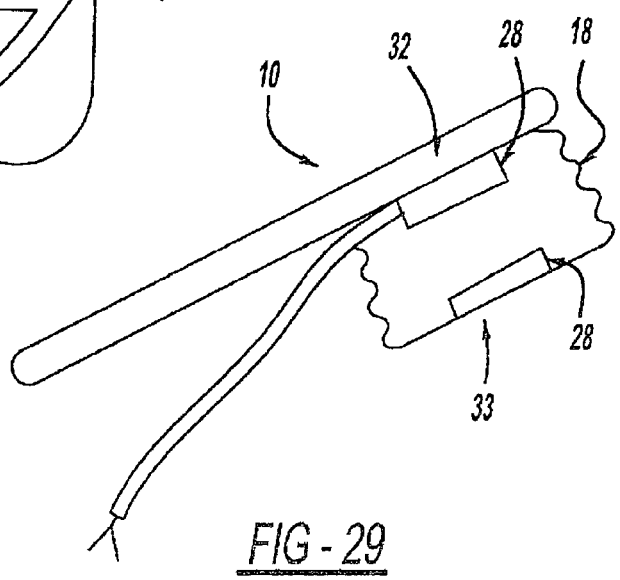
FIG. 29 is a side view of an electromagnetic inflation mechanism.

The inflation mechanism 28 can also be an electromagnetic system, shown in FIG. 29, that can be activated externally by a switch that turns on an electromagnet causing the expandable member 18 to expand or contract. For example, one electromagnet can be on the top side 32 of the expandable member 18 and another electromagnet can be located opposite thereto on a bottom side 33, and they can be toggled between attracting each other (contracted state) and repelling each other (expanded state). Appropriate electronics and leads can be included to operate the magnets. The inflation mechanism 28 can also be water, air, a self-curing polymer, or a material that reacts to moisture or heat found in the vagina.

The expandable member 18 can be naturally in an expanded state and must be actively contracted, or alternatively, the expandable member 18 can be naturally in a contracted state and must be actively expanded. Specific examples of the active contraction mechanisms are springs inside the expandable member 18 (further described below), an elastic mechanism attached to the expandable member 18, or an elastic material. Alternatively, the expandable member 18 can include a mechanism for expanding automatically, such as elastics and a one-way valve for allowing air to enter as the expandable member expands. An example of an irreversibly expandable device 10 with active contraction is shown in FIGS. 26A-26B, wherein the inflation mechanism 28 is a zip-tie-like chord that can be pulled, ratcheting the expandable member 18 down.

Figure 9A:
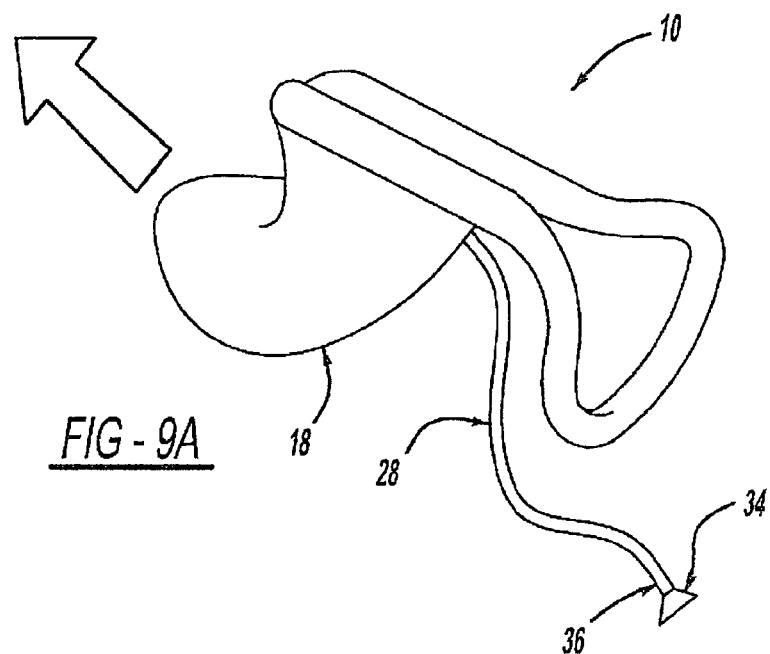
FIGS. 9A-9C show the device including a cap with the inflation mechanism.
Figure 9B:
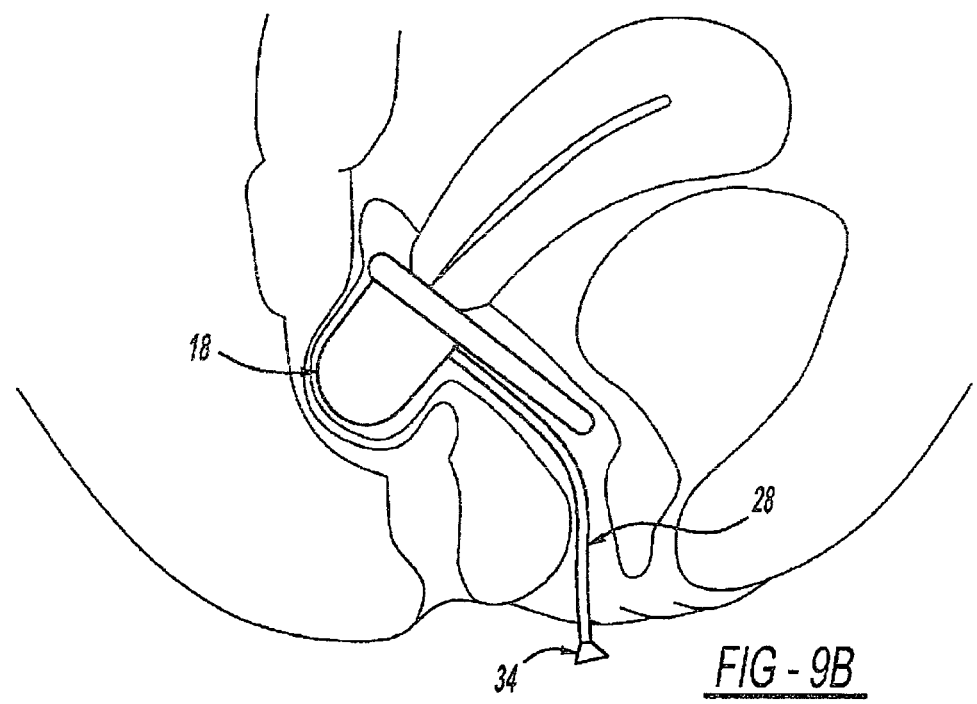
Figure 9C:
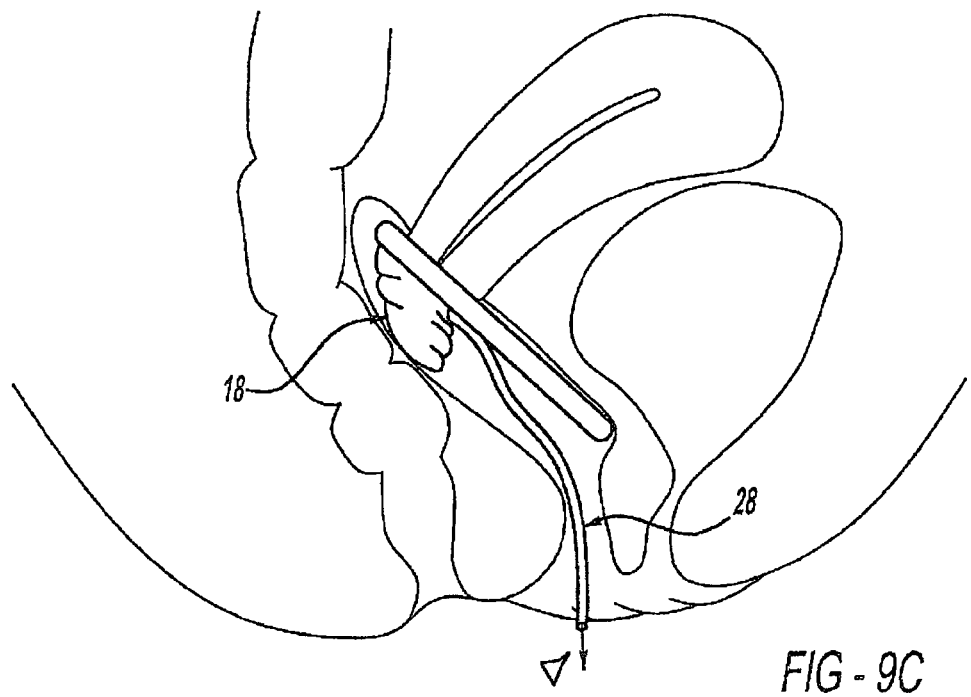
Figure 10A:
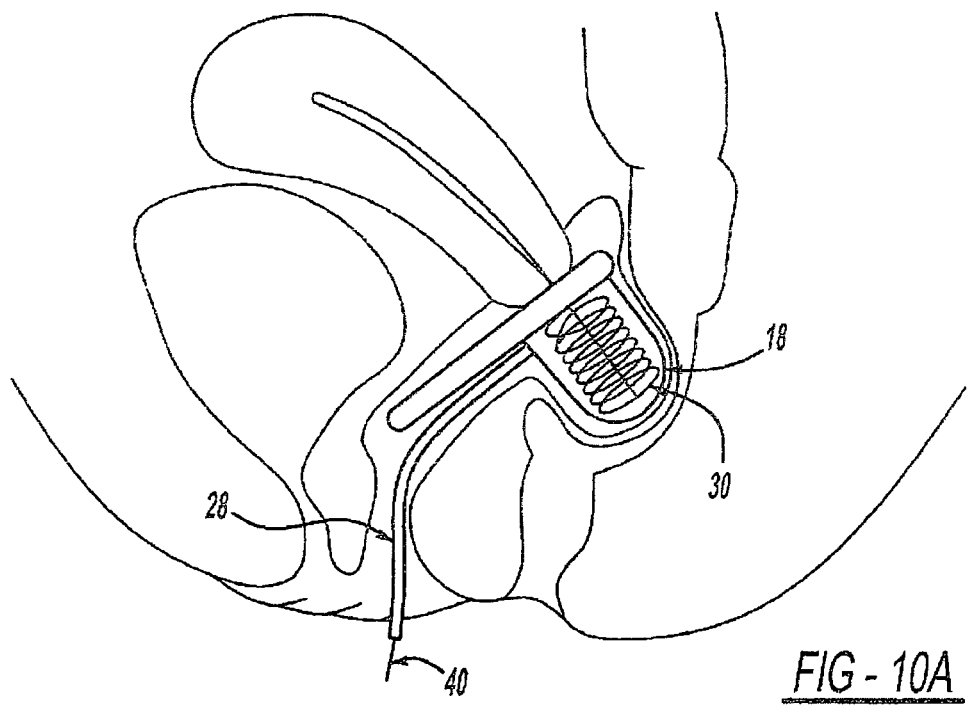

The inflation mechanism 28 can further include a cap or a valve 34 on a distal end 36 that is accessible outside of the body, as shown in FIGS. 9A-9C. By use of the cap 34, the expandable member 18 can be inflated fully or partially prior to insertion of the device 10 in the body. The cap 34 can be removed or actuated to deflate the expandable member 18 and allow stool to pass through the rectum. To enhance deflation, the fluid in the expandable member 18 can be actively expelled by means of a pump. The expandable member 18 can then be expanded again, either by a mechanism as described above, or the expandable member 18 can expand on its own due to the stiffness of the material it is made from.

The expandable member 18 can include a spring 38 that self-expands the expandable member 18, as shown in FIGS. 10A and 10B, and 11A and 11B. In other words, the expandable member 18 can be self expandable by various means, requiring active deflation or contraction to allow fecal passage. In this embodiment, the user would not have to actively inflate or expand the device during use. Rather, the user would actively deflate or contract the device to allow for fecal elimination.

The inflation mechanism 28 can include a string 40 accessible to the user outside of the body that can be pulled to collapse the spring 38 and allow stool to pass. After the string 40 is released, the spring 38 pushes the expandable member 18 back into an expanded state naturally. In other words, this expandable member 18 is generally in an expanded state and must be actively contracted. The spring 38 can also work with the cap 34 described above instead of the string 40. A tube or a wire can also be used in place of the string 40. The spring 38 can also be controlled by a component separate from the device 10, such as a rod, a threaded member, or a keyed member, that is insertable into the vagina for engagement with the spring 38. Preferably, these mechanisms that extend outside of the vagina are of minimal size so as not to cause discomfort of the user. This can include tubes that are collapsible to a generally flat profile and can be opened with the insertion of an additional component to aid in inflation/deflation (shown in FIGS. 25A-25B).

Figure 30A:
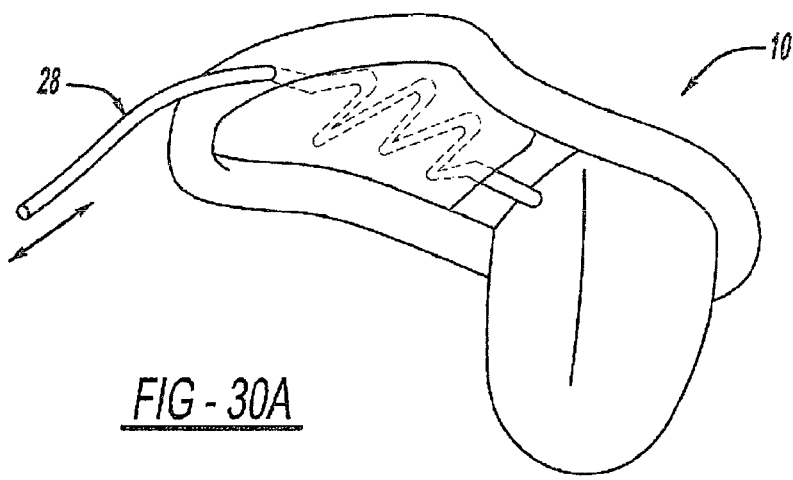

The inflation mechanism 28 can further include a latching mechanism 60 for holding the inflation mechanism 28 (preferably in the form of a tube) in a retracted position inside the vagina, shown in FIGS. 23A-23C. Users can prefer the comfort of this option as opposed to allowing an inflation mechanism 28 to extend outside the vagina. The latching mechanism 60 can include a first component towards a distal end of the inflation mechanism and a second component on the stabilizing body 12, the expandable member 18, or the inflation mechanism 28 proximate to the stabilizing body 12. The latching mechanism 60 can be a mechanical latch (such as a clip, FIG. 23C), a magnetic latch (FIG. 23B), or a hook and loop latch. The inflation mechanism 28 can be retractable into the stabilizing body 12 or the expandable member 18 when not in use (FIGS. 30A-30B). The latching mechanisms 60 can also be features attached to the inflation mechanism 28 that, based on their size and shape, are retained above the introitus. These features can also facilitate the retrieval of the inflation mechanism 28 when inflation/deflation is required.

The inflation mechanism 28 can further include an attachment mechanism 62 towards a distal end of the inflation mechanism 28 for pulling it or the device 10 downward, or for tucking and maintaining the inflation mechanism 28 inside the vagina. The attachment mechanism 62 can be a flexible or non-flexible ring or loop, as shown in FIGS. 24A-24B.

Figure 28C:
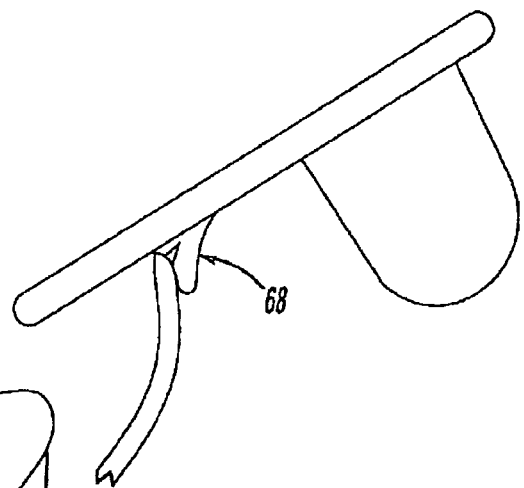
Figure 28D:
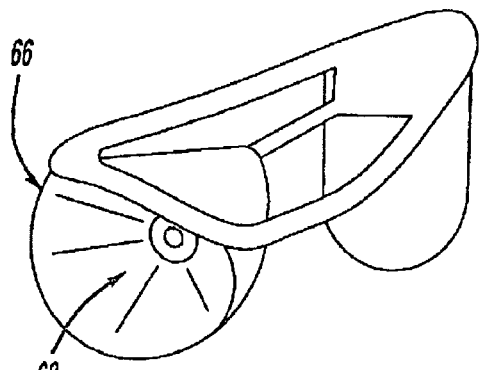

The inflation mechanism 28 can be external to the vagina and engage the intra-vaginal device 10 to permit the exchange of fluid with the expandable member 18 (FIG. 28A). In this case, the inflation mechanism is preferably a syringe, or pump that interfaces with the intra-vaginal device 10. The inflation mechanism 28 can interface with a valve 68 or system of valves on the stabilizing body 12 or the expandable member 18. The stabilizing body 12 or the expandable member 18 can include a mechanism 66 for directing the inflation mechanism 28 to the valve 68 or system of valves, such as a funnel structure (FIGS. 28C-28D), or a magnetic attraction (FIG. 28B).

The expandable member 18 can further include a supportive member 30, such as a cut silicon sheet or a molded silicon member, in order to prevent the expandable member 18 from tilting due to force from the presence of stool in the rectum. FIGS. 6A-6D show what can happen to the expandable member 18 with force applied thereto, i.e. the expandable member 18 can begin to tilt upwards into the stabilizing body 12, and not completely block the passage of stool. Therefore, a supportive member 30 can be attached between the expandable member 18 and the stabilizing body 12 so that tilting is prevented. The supportive member 30 can cover the entire surface of a top side 32 of the expandable member 18, as in FIG. 6E, or the supportive member 30 can be only a strip covering a portion of the top side 32, as in FIG. 6F. The supportive member 30 can also be integrated directly in the top side 32 of the expandable member 18. The supportive member 30 can also cover a portion or an entire inner space of the stabilizing body 12 (as shown in FIGS. 21A-21D). The supportive member 30 can be made of any suitable material that can withstand the force of the stool on the expandable member 18 and maintain the expandable member 18 in position.

The expandable member 18 can further include reinforcements 42 circumferentially around the surface, such as string, stiffer material than the expandable member 18 itself, or a thicker portion of the same material, as shown in FIGS. 11E-11F. The reinforcements 42 can aid in stretching the expandable member 18 in a preferential direction, i.e. at the 45-135 degree angle to the rectum wall. The supportive member 30 can also include reinforcements 42 for preventing deflection such as embedded fibers, plastic, or metal.

The expandable member 18 can also support anatomical features external to the vaginal cavity to prevent their prolapse into the vaginal cavity.

Figure 12A:
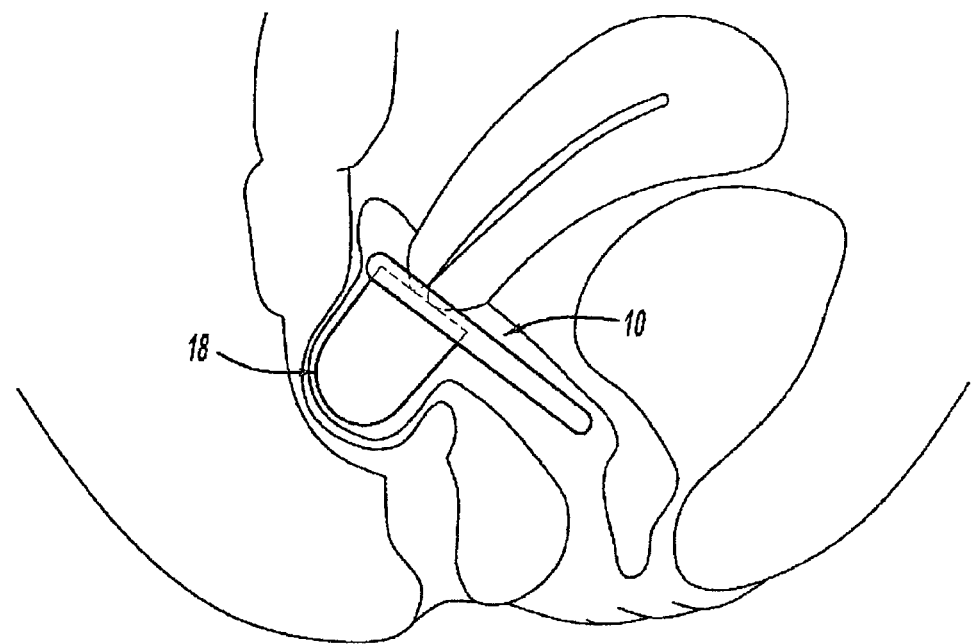
FIGS. 12A-12C show views of the device to accommodate a larger cervix.
Figure 12B:
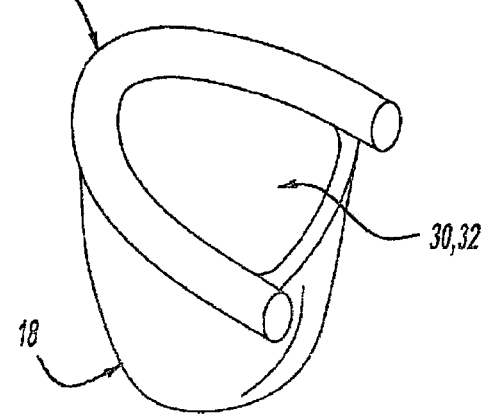
Figure 12C:
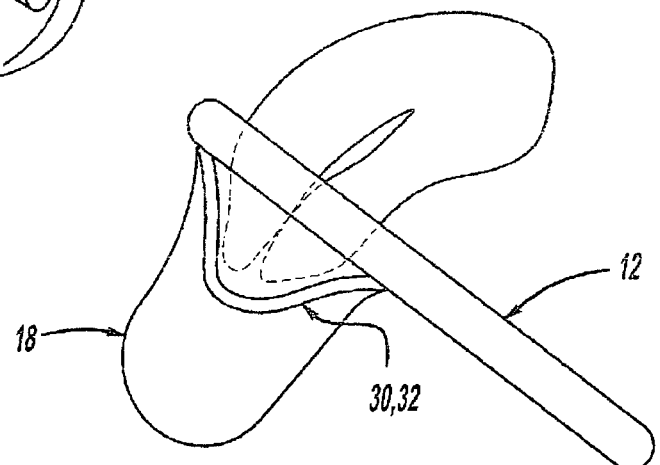

In order to ensure a comfortable fit for users who have a more prominent cervix (FIG. 12A), the top side 32 of the expandable member 18 and/or supportive member 30 can be bowed into the expandable member 18, accomplished by an indentation or a hole, as shown in FIGS. 12B-12C. Any suitable amount of bowing can be used and this aspect can be designed for a particular user by trial and error fitting, or medical imaging analysis of the vagina.

Figure 17A:
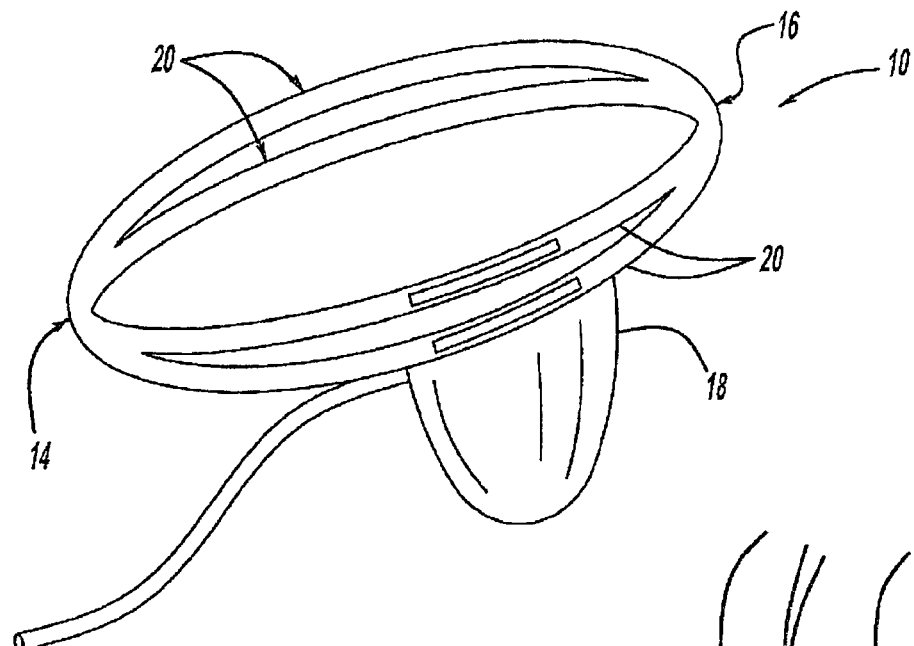
FIGS. 17A-17B are views of the device fitting with the cervix.
Figure 17B:
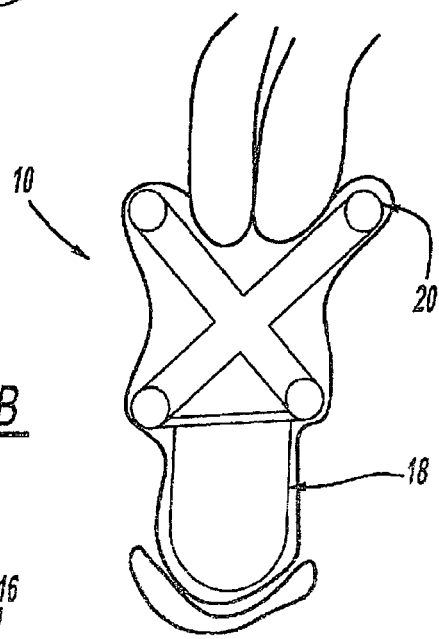
Figure 17C:
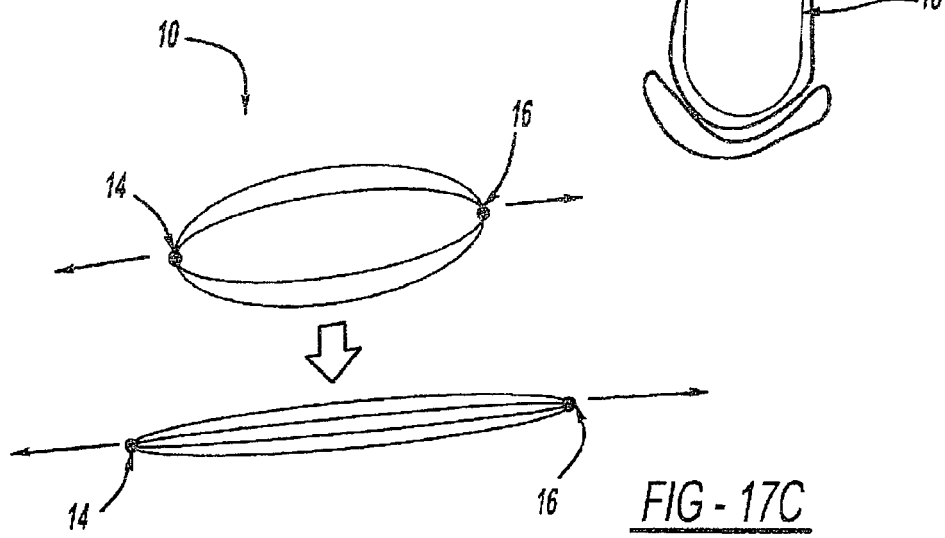
FIGS. 17C-17E are side views of the device collapsing and expanding.
Figure 17D:
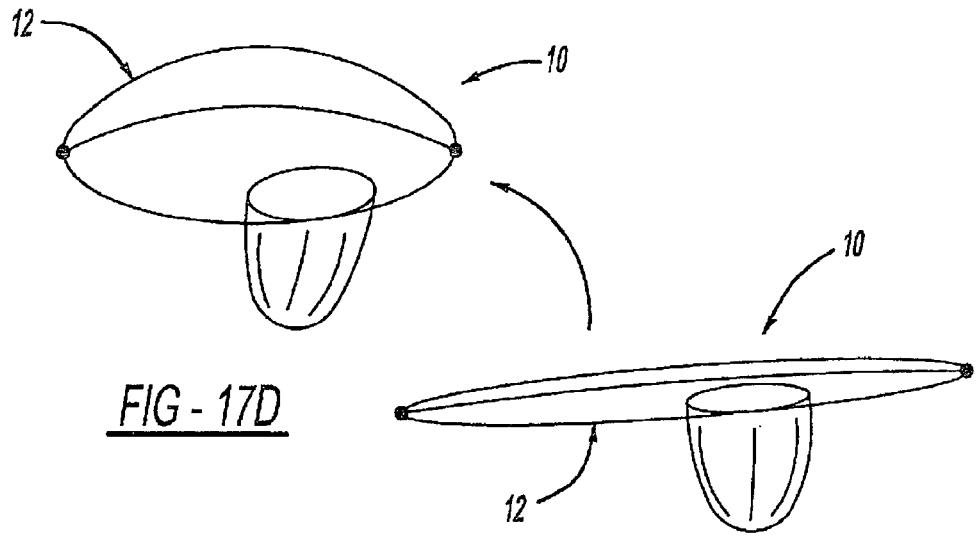
Figure 17E:
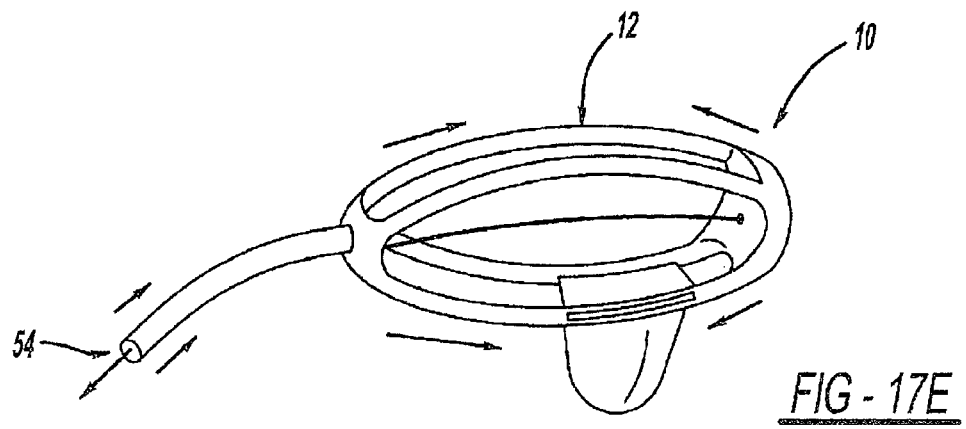

FIGS. 17A and 17B also show the device 10 with multiple sides 20 or rails of the stabilizing body 12 extending from the anterior end 14 to the posterior end 16 that anchor the cervix and also prevent rotation along the length of the device 10. FIG. 17C shows that in this form, the stabilizing body 12 can be collapsed to a smaller profile for insertion, such as by pulling on the ends 14, 16 of the device 10. The spring forces in the sides 20 can also cause the device 10 to spring back to the larger profile (FIG. 17D). The device 10 can also be forced into the larger profile, such as by a member 54 that can be pulled, pulling the ends 14, 16 of the device 10 together (FIG. 17E).

Various aspects of the device 10 can also serve to support other organs around the vagina to help alleviate symptoms of prolapse.

Figure 8A:
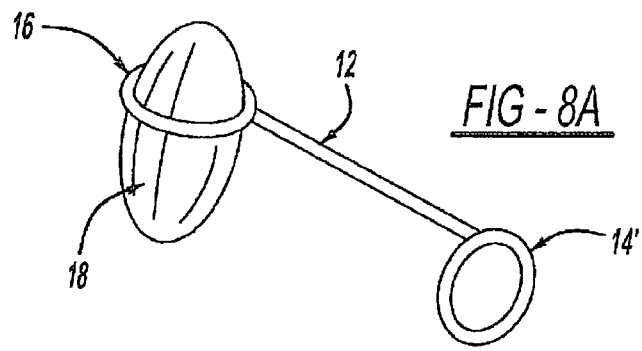
FIGS. 8A-8M show alternative stabilizing body and anterior end shapes.
Figure 8B:
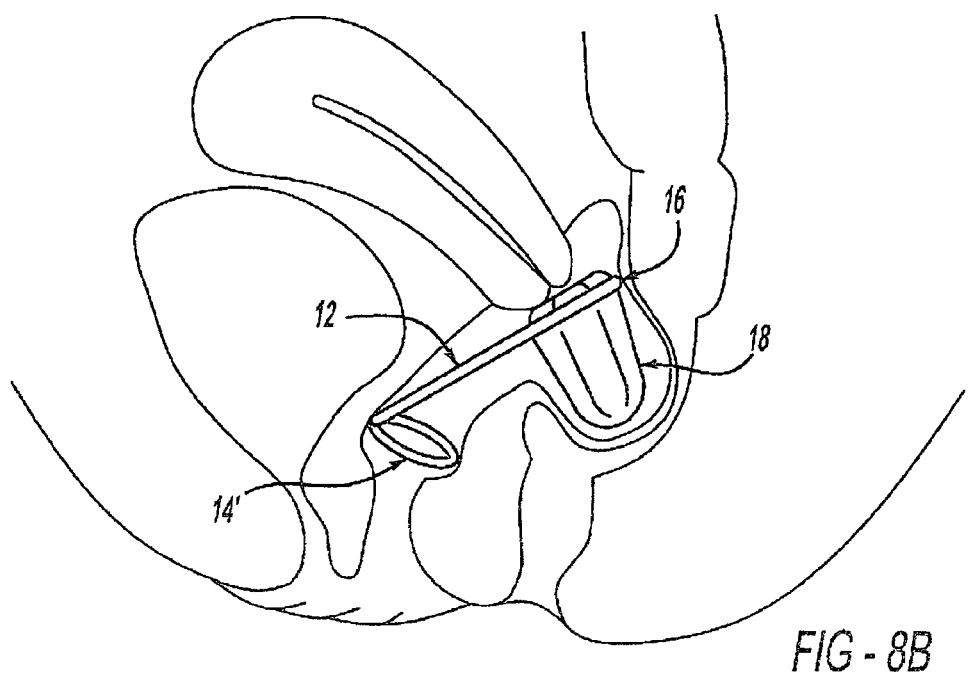
Figure 8C:
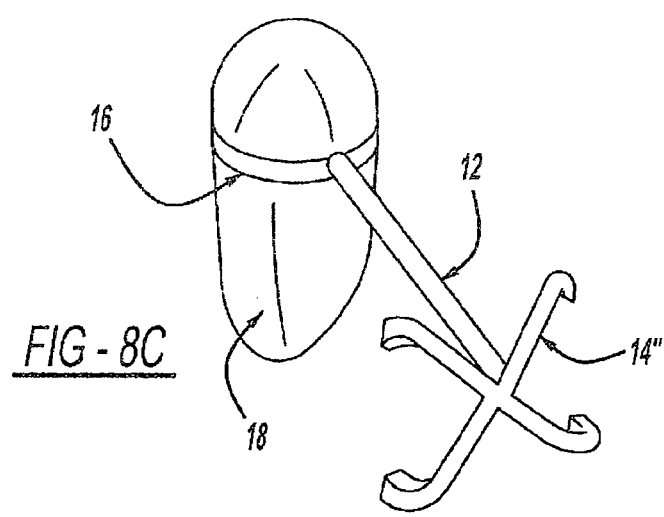
Figure 8D:
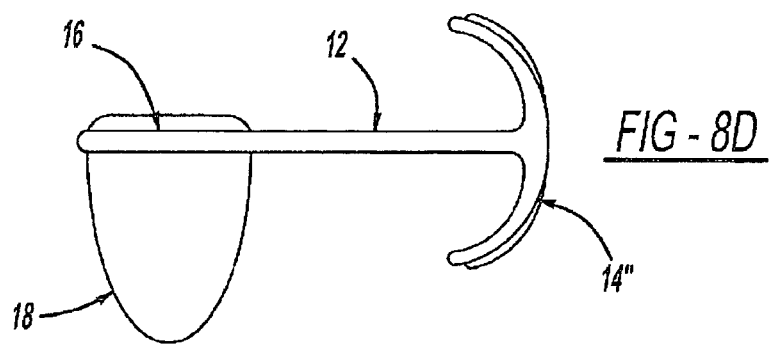
Figure 8E:
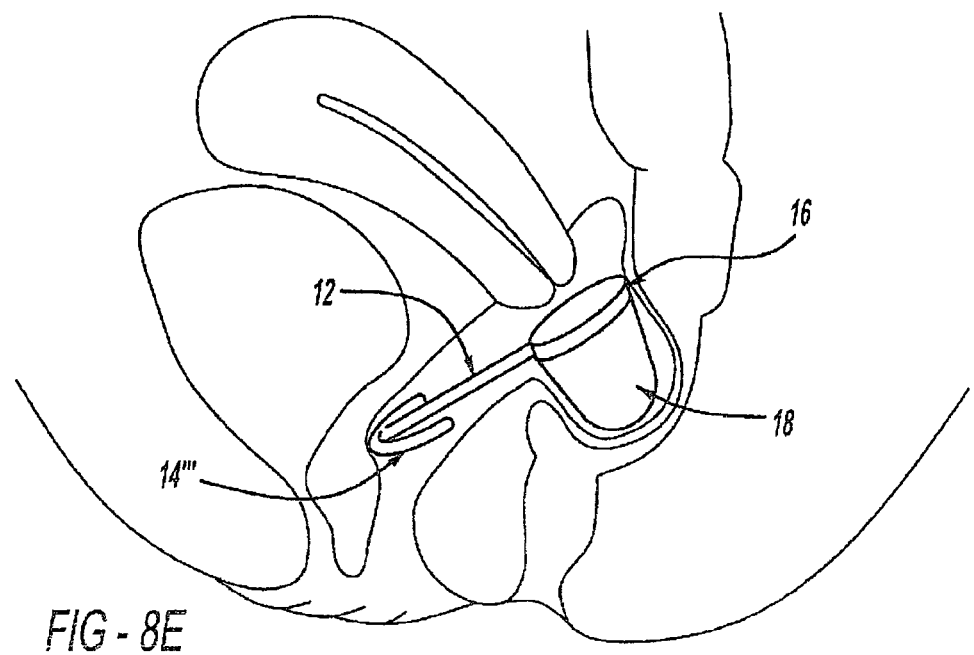
Figure 8F:
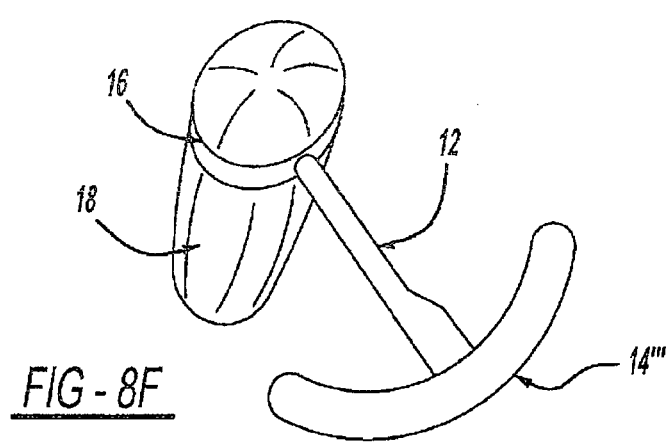
Figure 8G:
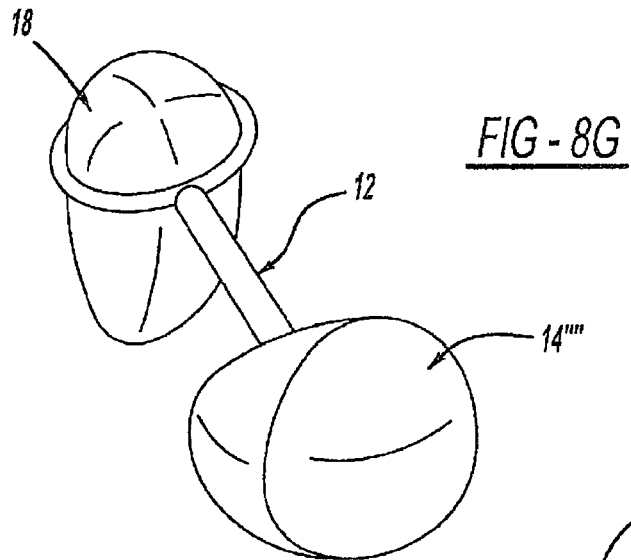
Figure 8H:
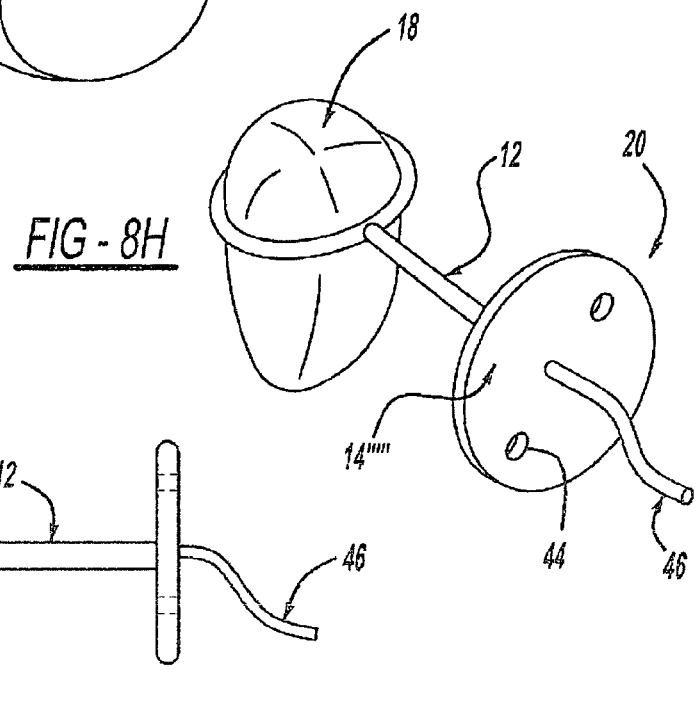
Figure 8I:
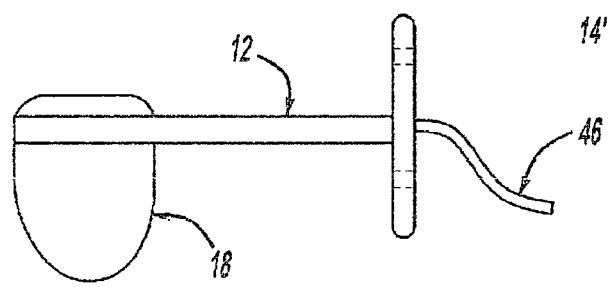

The stabilizing body 12 can include an anterior end 14 with other shapes, projections, or space-occupying features in order to keep the device 10 stable in the vagina, but not cause lateral displacement of the vagina walls. For example, the stabilizing body 12 can include a ring-shaped anterior end 14', shown in FIGS. 8A-8B. The stabilizing body 12 does not have two sides of a central portion 20 in this case but rather a single central portion 20 connects the anterior end 14' and the posterior end 16. The anterior end 14" can also be a cross-shape, or anchor shape as shown in FIGS. 8C-8D. The anterior end 14''' can also be a multi-pronged anchor shape, as shown in FIGS. 8E-8F. The anterior end 14'''' can be a soft or spongy portion, e.g. tampon-like material, that prevents the device 10 from sliding out in FIG. 8G and also expands as it absorbs body fluids such as water. The anterior end 14''''' can be a disc or diaphragm that is a generally perpendicular planar body to act as a plug to keep the device 10 inside the introitus as shown in FIG. 8H-8I. The disc 14'41 " can be a soft material such as a compliant cushion so that it can deform during insertion, and can also provide suction. Drainage holes 44 can be included as well as a removal mechanism 46, such as a string or soft silicon, which can extend outside of the vagina to facilitate removal 15. The disc 14''''' can include an embedded member which can be pulled to reversibly or irreversibly disrupt the mechanical integrity of the disc 14''''' such that the device 10 is easily removed. The removal mechanism 46 can be included on any embodiment as well, and can be a ring, string, wire, flap, rod, or tube.

Figure 8J:
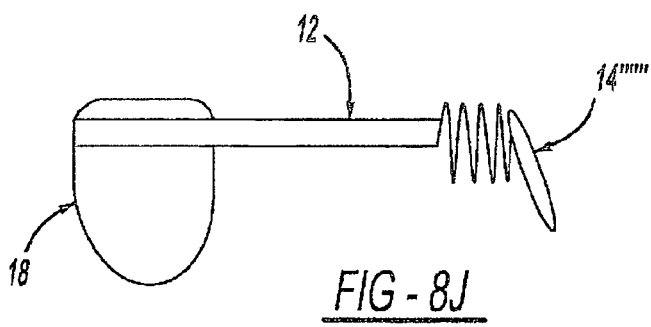
Figure 8K:
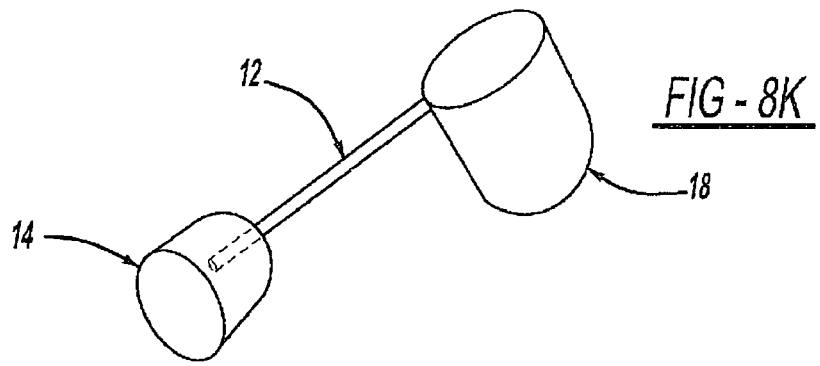
Figure 8L:
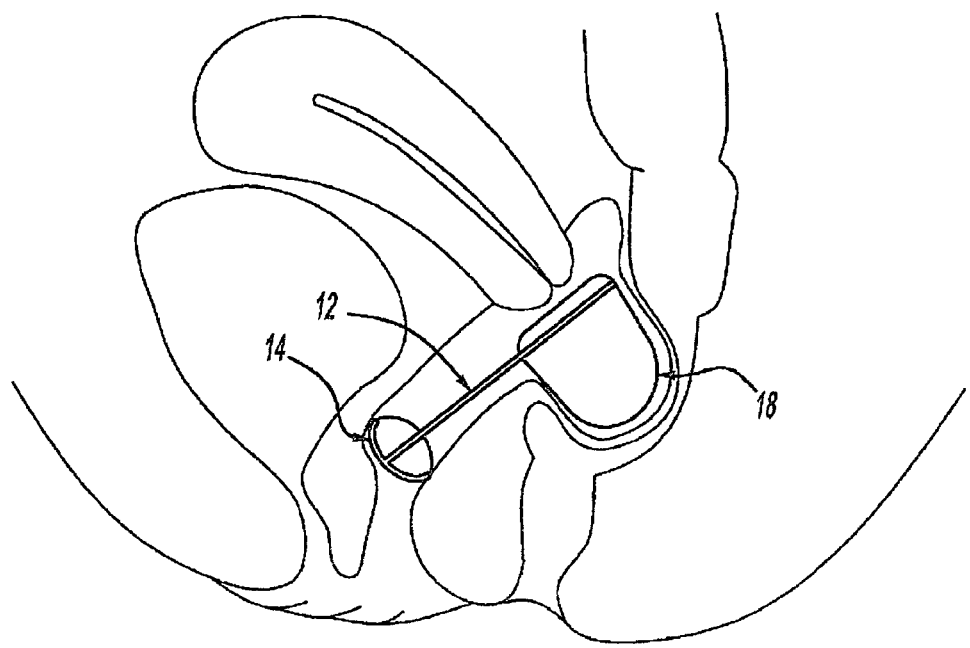
Figure 8M:
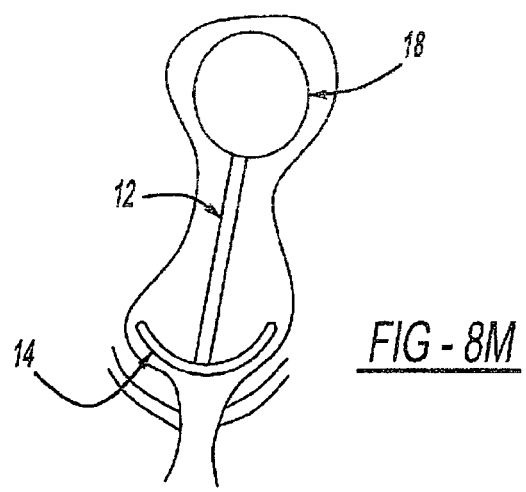

The anterior end 14'''''' can be mechanisms to secure the device 10 in the vagina as well as allow for easy removal, such as a spring and tab as shown in FIG. 8J. The tab can be depressed and cause the spring to be contracted, allowing for removal of the device 10. Additionally, the anterior end 14 can be shaped to approximate the curvature of the pelvic floor muscles it interacts with.

Another important aspect of the device 10 is that it has positional stability and rotational stability within the vagina. The positional stability is provided by points of contact of the device 10 with the vagina, most notably the anterior end 14 with the pubic notch and the posterior end 16 with the posterior fornix. The expandable member 18 can further provide stability with contact with the wall of the vagina. It is this positional stability that allows the stabilizing body 12 to be designed in different shapes as long as these points of contact remain. Rotational stability is provided as well by the contact of the anterior end 14 with the pubic symphysis and the posterior end 16 with the posterior fornix. This rotational stability limits the rotation of device 10 when the expandable member 18 is expanded. Additionally, rotation around the device's anterior-posterior axis is prevented by extensions off of this axis as described above, and more specifically by a generally planar structure. Even more specifically, this rotation is prevented by the additional width of the stabilizing body 12 at either end of the device 10. The expandable member 18 contacts the same part of the vagina wall to occlude the rectum every time that the device 10 is used.

Therefore, the present invention provides for a stabilizing mechanism for repeatably contacting the force applying portion 18 with a same area of an anterior rectum wall, the force applying portion 18 being able to inhibit the ability of the rectum to expand to allow stool to pass through. These aspects of the invention are critical for assuring maximum comfort and reliability of results for the user.

The stabilizing mechanism can be longitudinal members (i.e. sides 20 and the anterior end 14 and posterior end 16) that form a three-dimensional structure that can change from a smaller profile for insertion to a larger profile for stability. This ability to change the form is described above with the springs 26. The longitudinal members can exert a spring force biasing them towards the larger profile. A mechanical mechanism can be used to secure the longitudinal members in the larger profile, such as a compression mechanism for drawing ends of the longitudinal members close together, i.e. a string, wire, tube, chain, flexible rod, or threaded member.

An additional embodiment utilizes suction forces on a body for stabilization means to allow repeatable positioning and repeatable contact to the recto-vaginal septum (FIGS. 16A-16E. These bodies can be different shapes other than the preferred shape described herein, such as, but not limited to, a cube, wedge, or pyramid, provided they meet the described criteria for stabilization and force application.

In an additional embodiment, the stabilizing mechanism can be secured to a body through surgical attachments to one or more walls of the vagina as described above. The stabilizing mechanism can also include adhesive to secure in the body.

More generally, the device 10 can substantially maintain a single shape that applies force to the rectum. This force can be modulated by changing the position of the device 10 inside the vagina, or by removal and insertion of the device 10.

The present invention also provides for an intra-vaginal device 10 including a stabilizing mechanism as described above for stabilizing the device 10 to prevent rotation and translation in the vagina, thereby allowing a portion of the device 10 to reversibly apply force to the same area of the rectovaginal septum to control stool movement through the rectum. The importance of applying pressure on the same area of the rectum has been described above.

The present invention provides for a method of controlling stool movement through the rectum, by stabilizing the intra-vaginal device 10 described above and preventing rotation and translation in the vagina, reversibly applying force to the same area of the rectovaginal septum with the device 10, and controlling stool movement through the rectum. The force can be applied with the force applying portion 18 as described above.

The present invention also provides for an intra-vaginal device 10, including a stabilizing mechanism for stabilizing the device 10 to prevent rotation and translation in the vagina in a first and second state, wherein when in a first state, force is not applied to the rectovaginal septum (RVS) and, wherein when in a second state, force is applied to the RVS thereby allowing a portion of the device to reversibly apply force to the same area of the rectovaginal septum to control stool movement through the rectum.

The present invention provides for a method of controlling stool movement through the rectum, including the steps of stabilizing the intra-vaginal device 10 described above and preventing rotation and translation in the vagina when the device 10 is in a first and second state, wherein when in a first state, force is not applied to the rectovaginal septum (RVS) and, wherein when in a second state, force is applied to the RVS, reversibly applying force to the same area of the rectovaginal septum with the device, and controlling stool movement through the rectum.

Figure 13A:
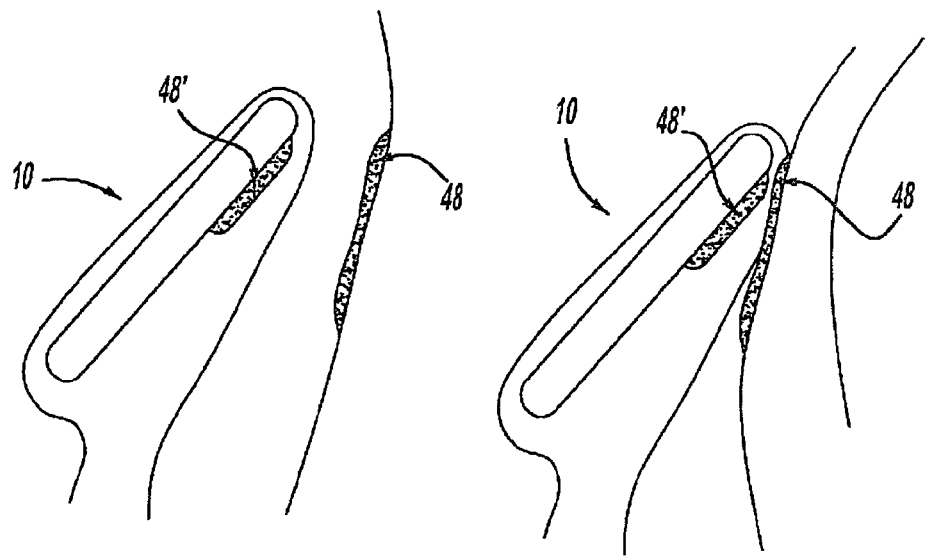
FIGS. 13A and 13B are side views of the device with additional occlusion mechanisms.
Figure 13B:
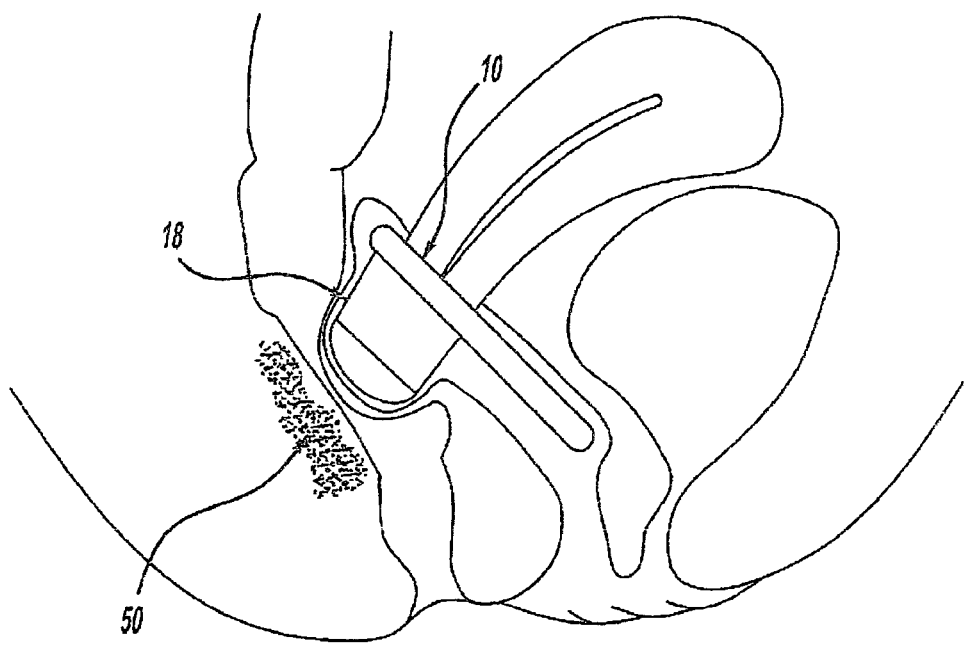

There can be other mechanisms used along with the device 10 in order to achieve rectal occlusion. For example, a magnet 48 can be surgically implanted in the posterior rectal wall in order to interact with a corresponding magnet 48' on the device 10, such as at the bottom of the expanding member 18 as shown in FIG. 13A. The magnets 48, 48' can be electromagnets and can be externally controlled, allowing them to interact with each other to occlude the rectum or to let stool pass. Alternatively, magnet 48' can be simply implanted in the vagina wall opposite the posterior rectum wall without the device 10 to achieve the same results. Also, a mass-occupying agent 50 can be injected into the posterior rectal wall, as shown in FIG. 13B, so that when combined with the device 10, better occlusion of the rectum occurs. Preferably, the mass-occupying agent 50 is directly opposite to the expanding member 18 and interacts therewith. The device 10 can be used with an implanted sling that pulls the rectum anteriorly.

The present invention provides for a method of controlling the passage of stool in a patient, including the steps of inserting the intra-vaginal device 10 into the patient's vagina such that the anterior end 14 rests around the pubic notch and the posterior end 16 rests in the posterior fornix, exerting a force towards the posterior side of the vagina, preventing expansion of the patient's rectum with the force, impeding the passage of stool, and removing the force, allowing stool to pass. By performing this method, the patient can use the device 10 to prevent stool from passing or allow stool to pass through the rectum. When inserting the device 10, the sides 20 can narrow by the operation of the springs 26 at the anterior end 14 and posterior end 16 for easier insertion. Then the sides 20 return to their normal open position once the device 10 is positioned around the pubic notch and in the posterior fornix. Preferably, the force applying portion 18 exerts the force and moves the anterior wall of the rectum. As described above, the force applying portion 18 can be expanded manually or electronically. As the force applying portion 18 expands, because there is slack in the vagina walls, the force of expansion is directed against the rectum, and passage of stool is inhibited. The force can be exerted substantially above the perineal body. The prevention can be an occlusion of the rectum. When it is desired that stool pass through the rectum, the expandable member 18 is contracted (there can be recovery of the expandable member through various mechanisms described above) and the walls of the rectum are allowed to accommodate stool normally.

In an alternative embodiment, device 100 includes a stabilizing body 102 having an anterior end 104 and a posterior end 106, the posterior end 106 operatively connected to an occluding member 108 and including a toggle mechanism 110 for toggling the occluding member 108 between an occlusive and passive state. Essentially, the occluding member 108 can change orientation between a rectally occlusive state, shown in FIG. 14A, to a passive state to allow stool to pass through the rectum, shown in FIG. 14B. The device 100 is generally the same as device 10 described above, except that instead of expanding, the occluding member 108 toggles positions. The device 100 preferably is situated in the vagina such that the anterior end 104 rests around the pubic notch and the posterior end 106 rests in the posterior fornix.

Figure 33A:
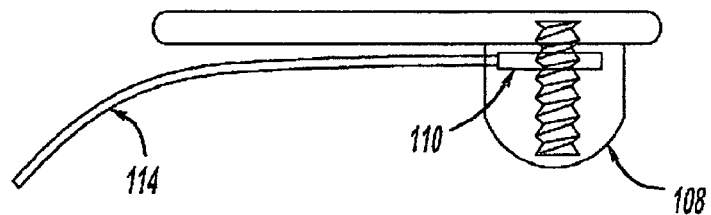
FIGS. 33A-33B are side views of a threaded toggle mechanism.
Figure 33B:
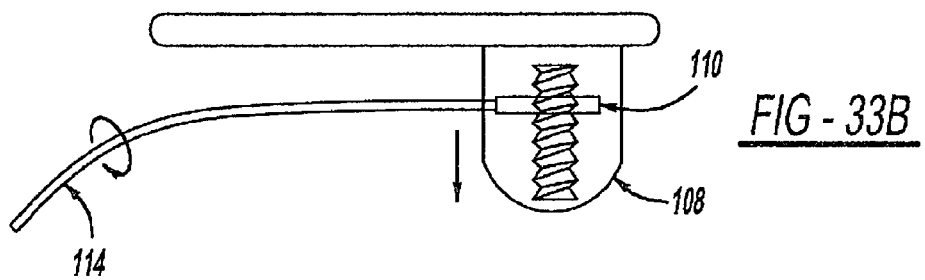
Figure 33C:
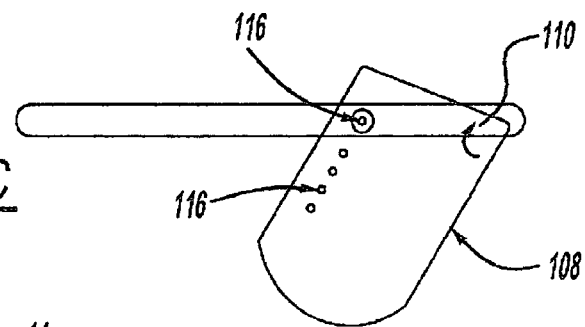
FIG. 33C is a side view of a snap-fit locking mechanism.

The toggle mechanism 110 can be any mechanism known in the art to toggle positions of the occluding member 108. For example, the toggle mechanism 110 can be a hinge or a flexible joint that joins the occluding member 108 to the stabilizing body 102. The toggle mechanism 110 can be a translatable occlusive member such as a slidable occlusive member, or an occlusive member with multiple locked positions such as snap-fit locking mechanisms. (FIG. 33C). The toggle mechanism 110 can also be a threaded member that can be extended or retracted by engaging one or more threads, shown in FIGS. 33A-33B. Preferably, the toggle mechanism 110 includes a method of locking the occluding member 108 when occlusion is desired and so that movement of the occluding member 108 does not occur. A latch mechanism 112 can be used to lock the occluding member 108 in the occluding position as shown in FIGS. 14C-14D anywhere on the occluding member 108 and stabilizing body 102, such as on a side opposite to the toggle mechanism 110. The toggle mechanism 110 can include a control string 114, as shown in FIGS. 14E-14F, or any other control component that extends outside of the vagina such as a wire, tube, lever, or threaded component. The control string 114 can be attached anywhere appropriate on the occluding member 108. Under tension of the control string 114, the occlusive member 108 cannot move and is locked in place in an occluding position. When tension in the control string 114 is released, the occlusive member 108 is free to rotate and moves to a passive position to let stool through the rectum. The occluding member 108 can have an altered or more tapered shape on a side opposite to the toggle mechanism 110 in order to have a more comfortable fit when in the passive position, as shown in FIG. 14G.

In an alternate embodiment, the intra-vaginal device can be toggle between and occluding and non-occluding state by removing the device in its entirety from the vagina.

Therefore, the present invention provides for a method of controlling the passage of stool in a patient, including the steps of inserting the intra-vaginal device 100 into the patient's vagina such that the anterior end 104 rests around the pubic notch and the posterior end 106 rests in the posterior fornix, toggling the occluding member 108 at the posterior end 106 to an occlusive state, preventing expansion of the patient's rectum with the occluding member 108, impeding the passage of stool, and toggling the occluding member 108 to a passive state, allowing stool to pass. This method is generally performed as the method described above, except that instead of expanding the expandable member 18, the occluding member 108 is toggled between an occlusive state to occlude the passage of stool in the rectum and a passive state to allow the passage of stool. The toggling step can further include shifting the occluding member 110 to different snap-fit positions, (FIG. 33C) sliding the occluding member 110 to different position, or engaging threaded components on the occluding member 110 for moving the occluding member 110. The toggling step can be performed by actuating the control string 114 above, or a wire, tube, lever, or threaded component. These components for actuation can be outside of the vagina. The toggling step can also include locking the occluding member 108 with the latch mechanism 112 described above. The preventing step can also include occluding the rectum.

Figure 15D:
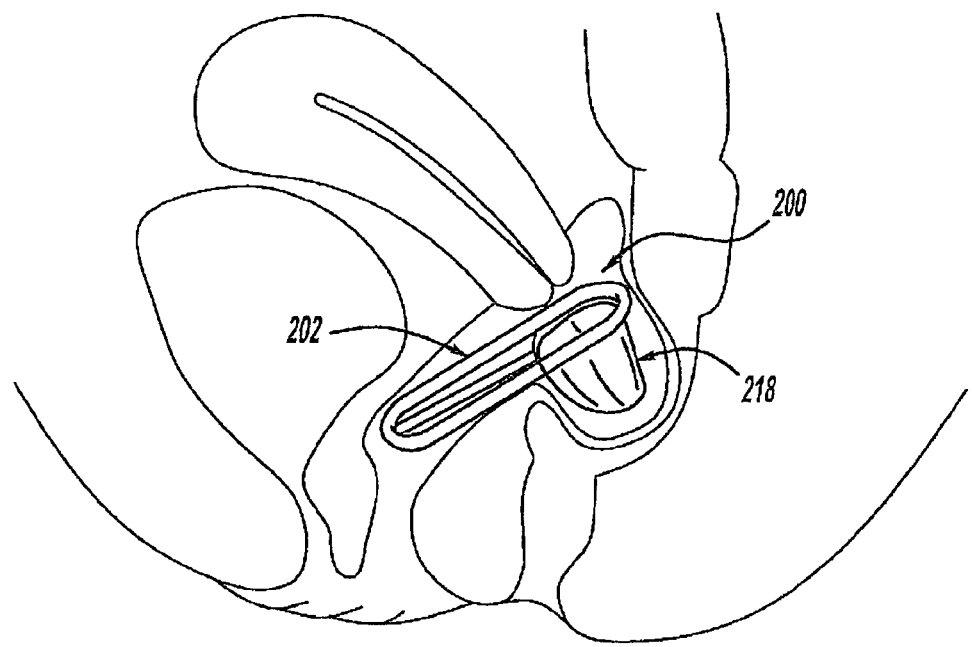
Figure 15E:
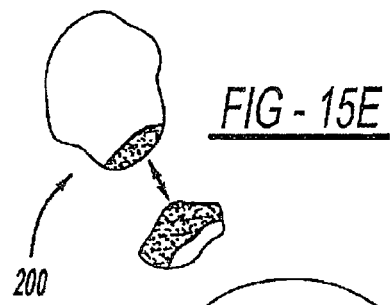
Figure 15F:
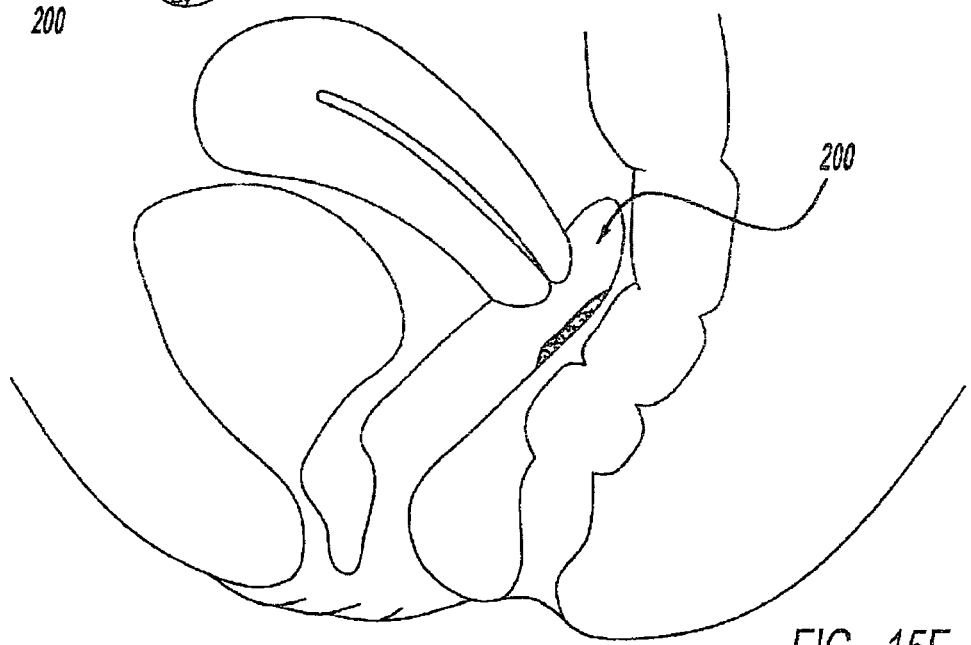
Figure 15G:
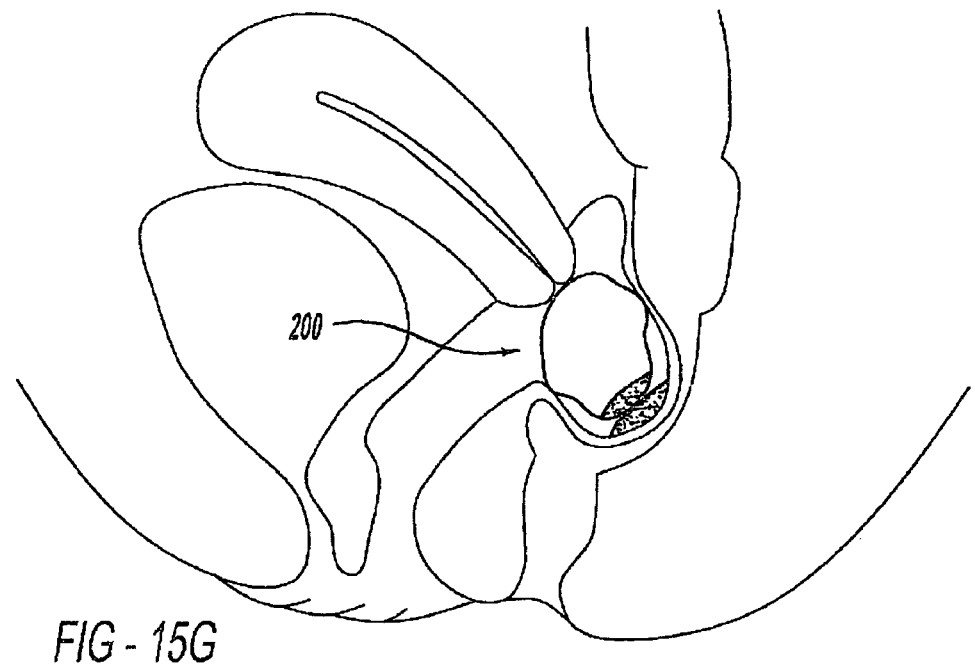
Figure 16A:
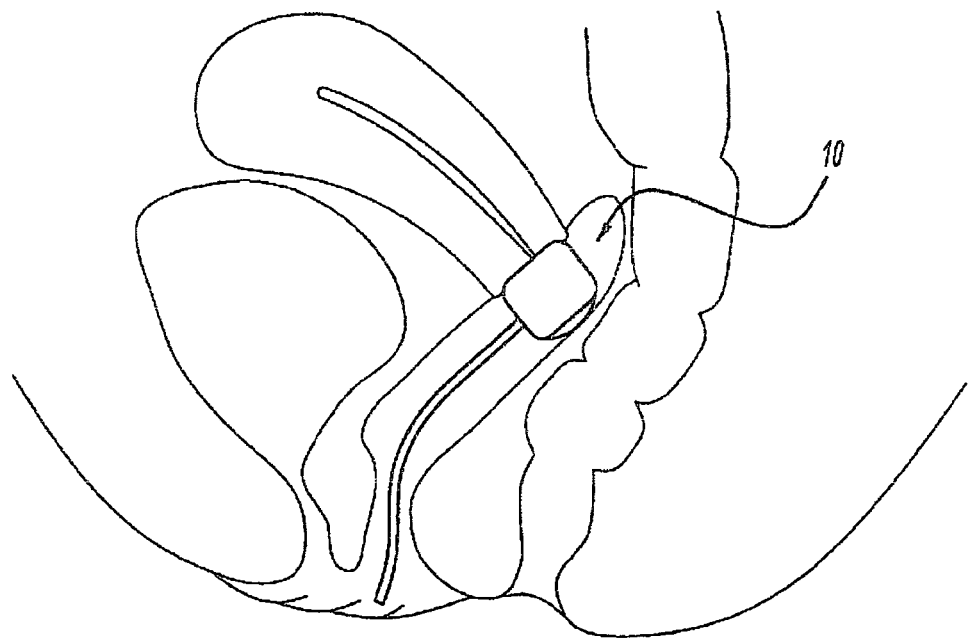

In another embodiment, shown in FIGS. 15A-15G, device 200 includes a stabilizing body 202 having an anterior end 204 and posterior end 206, the posterior end 206 including magnets 210 that act as a docking mechanism for receiving an occluding member 208 having magnets 210'. In this device 200, the stabilizing body 202 and occluding member 208 are separate pieces. Preferably, the stabilizing body 202 is generally as described above and the same shape, with the addition of magnets 210 in the posterior end 206 for receiving the occluding member 208. The device 200 preferably is situated in the vagina such that the anterior end 204 rests around the pubic notch and the posterior end 206 rests in the posterior fornix. The occluding member 208 has corresponding magnets 210' in areas that line up with the magnets 210 of the posterior end 206. The occluding member 208 can be a rigid material, or it can be semi-rigid and expandable, or compliant as described above. The occluding member 208 can include an insertion mechanism 212 that can be used for ease of insertion into the vagina and can aid in stabilizing the occluding member 208 within the stabilizing body 202. When in place, the insertion mechanism 212 can reach from the occluding member 208 to the anterior end 204, as shown in FIG. 15D. The stabilizing body 202 can alternatively, or in addition to the magnets 210, include a mechanical lock 214. In this case, the occluding member 208 also includes a matching mechanical lock 214' to secure the occluding member 208 in the stabilizing body 202. The docking mechanism can also be shape fit, i.e. the shape of the device 200 itself that allows for docking. When it is desired to prevent the passage of stool, the occluding member 208 can be inserted (and optionally expanded) and held in place by the magnets 210, 210' and/or the mechanical lock 214, 214'. The occluding member 208 can be adjustably docked along the length of the stabilizing body 202. The occluding member 208 can also cause the stabilizing body 202 to apply force. When it is desired to let stool pass, the occluding member 208 is removed (and optionally contracted). The occluding member 208 can further include mechanisms for removal, as described above, such as string, a tube, wire, a ring, a tab, a chain, or a flexible rod. In this embodiment, the stabilizing body 202 can be surgically implanted in the vagina and remain inside, whereas the occluding member 210 can be inserted or removed as desired, shown in FIG. 15E. In this case, the occluding member 210 can be disposable whereas the stabilizing body 202 is more of a permanent device. The present invention also provides for the occluding member 210 itself for controlling the passage of stool, wherein the occluding member 210 is a body and includes a securing mechanism for securing the occluding member 210 to a dock on the device 200.

Therefore, present invention further provides for a method of controlling the passage of stool in a patient, including the steps of inserting the stabilizing body 202 of the intra-vaginal device 200 into the patient's vagina, inserting the occluding member 208 in the vagina, docking the occluding member 208 on the stabilizing body 202, preventing expansion of the patient's rectum with the occluding member 208, and impeding the passage of stool. Preferably, the anterior end 204 rests around the pubic notch and the posterior end 206 rests in the posterior fornix. The docking of the occluding member 208 can occur by the interaction of the magnet Therefore, present invention further provides for a method of controlling the passage of stool in a patient, including the steps of inserting the stabilizing body 202 of the intra-vaginal device 200 into the patient's vagina, inserting the occluding member 208 in the vagina, docking the occluding member 208 on the stabilizing body 202, preventing expansion of the patient's rectum with the occluding member 208, and impeding the passage of stool. Preferably, the anterior end 204 rests around the pubic notch and the posterior end 206 rests in the posterior fornix. The docking of the occluding member 208 can occur by the interaction of the magnets 210, 210' and/or the mechanical locks 214, 214' as described above. The docking step can include placing the occluding member 208 such that it is compressed between the stabilizing body 202 and vaginal wall. The preventing step can include occluding the rectum. The method can further include the step of undocking and removing the occluding member 208 from the vagina, allowing stool to pass. Stool can be allowed to pass also by changing the position of the occluding member 208 instead of removal.

Figure 32A:
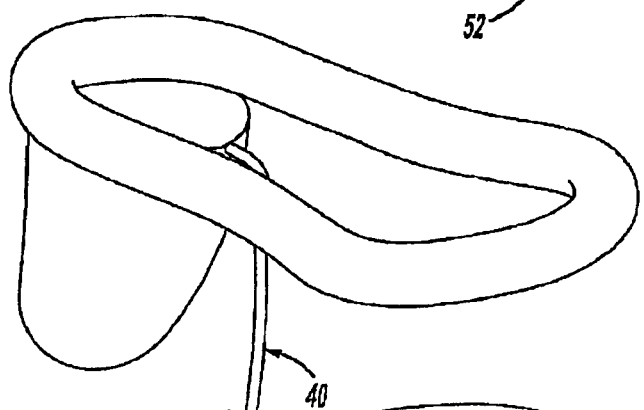
FIGS. 32A-32B are views of the device with a bleed mechanism.
Figure 32B:
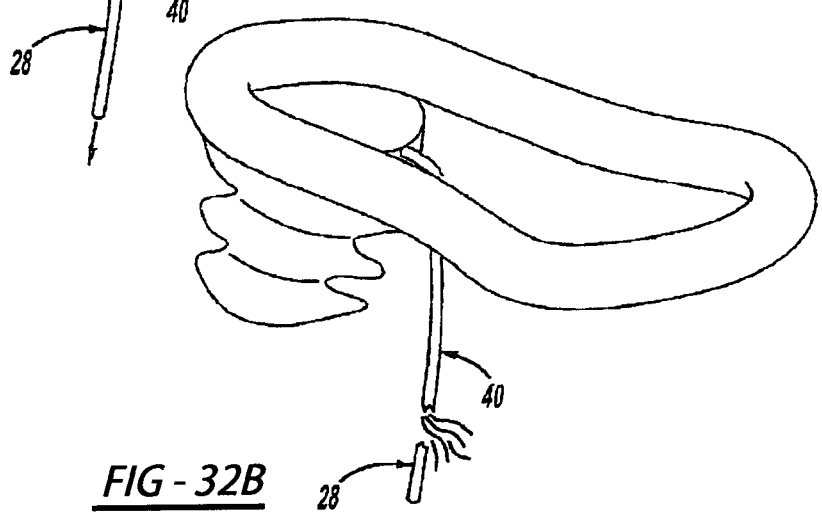

Any part of the devices 10, 100, 200 can be disposable and made of a material that allows for flushing down the toilet after a single use. For example, the expandable member 18/occlusive member 108, 208 can be irreversibly deflated upon activation of a feature. For example, a bleed in the form of a tube/string 40 can be pulled which trips a valve or detaches the tube 40 from the expandable member 18 or generally causes leakage of fluid, causing it to deflate, as shown in FIGS. 32A-32B. This allows the patient to pass stool and the device 10 is removed and disposed of. Any of the mechanical parts of the expandable member 18, such as the spring 38 can be actuated to irreversible collapse. Another example is the removal of the device 10 causes the stabilizing body 12 to irreversibly collapse or lose structural integrity, shown in FIGS. 27A-27B. The device 10, 100, 200 can be encased in an applicator, which is inserted in the vagina and upon actuation, the device expands into proper shape and rectal occlusion. A disposable pump (e.g. a bag filled with an amount of air) can be included with the device 10, 100, 200, which can be squeezed after insertion and then can be torn off and disposed of. The removal of the device 10 can also cause an irreversible mechanical compromising of the device 10 that prevents future use.

The present invention also provides more generally for a device including a stabilizing body for stabilizing the device in a body orifice and a force applying portion for applying force to an orifice wall, the stabilizing body imparting minimal tension on the walls of the orifice proximate to the force applying portion, such that the force applying portion can displace the orifice wall. In other words, the device 10 of the present invention is not limited to use in the vagina for rectal occlusion, but can be made in different sizes for different applications throughout the body. The stabilizing body can narrow proximate to the force applying portion to minimize tension on the orifice wall. A region proximate to the force applying portion can be narrower than one or both ends of the device. The force applying portion can reversibly apply force. The applied force can be imparted on a neighboring structure.

Therefore, the present invention also provides for a method of controlling flow of a substance through a body orifice, by stabilizing a device 10 and preventing rotation and translation in the body orifice, reversibly applying force to the same area of the body orifice with the device 10, and controlling the flow of the substance through the body orifice. This method can be performed as described above but it can be used in any part of the body, not just in the vagina for rectal occlusion.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Cadaver 1 Summary:

It was demonstrated herein the potential for an expanding intra-vaginal device by applying a force to the rectum to inhibit the passage of stool. However, it was demonstrated that existing devices were not capable of doing this and that there are certain key features necessary to achieve stool inhibition. For example, Inflatoball is an intra-vaginal pessary that expands non-directionally as a large rounded shape inside the vagina. Even at large volumes and pressures, the Inflatoball did not occlude the rectum because it did not direct the expansion. Similarly, other pessaries and intra-vaginal devices also were not able to occlude the rectum. The LiveSure V1, which consists of a tubular, cylindrical body with an attached inflatable portion that can expand to occlude the rectum, was used. However, it was unable to occlude the rectum because it had no means for stabilization. Upon inflation of the expandable portion, the main body would rotate or translate so that the expansion was no longer directed towards the rectum. The procedure was then repeated, with the LiveSure V1 held manually in place so that it would not rotate or translate. Upon doing so, the device was able to direct a force towards the rectum, but it required a very large force and placed a lot of strain on the rectovaginal septum in order to occlude the rectum, and even then, it could only partially occlude the rectum. The reason for this was that the design did not allow for enough slack in the tissue of the vaginal wall in order to deflect it posteriorly. Therefore, a large force needed to be used in order to stretch the tissue of the septum back towards the rectum—something that would likely be painful and physiologically damaging in a live patient. Both such problems of stability and high pressure requirements are also expected to occur with the embodiment described by Klingenstein. This highlighted the need for a design that was stable and could occlude the rectum without undo stress on the surrounding tissue. Results are shown in TABLE 1.

TABLE 1

| Device | Digital Rectal Exam |
| --- | --- |
| Inflatoball | Not Occluded |
| Other pessaries | Not Occluded |
| *LiveSure V1 | Not Occluded |
| *LiveSure V1 (Held in place and under high pressure and force) | Partial Occlusion |

*LiveSure V1 consists of a tubular, cylindrical body with an attached inflatable portion that can expand to occlude the rectum.

Cadaver 2 Summary:

This experiment sought to demonstrate a design that would allow for a stable positioning of the device. LiveSure V3 was tested. This device consisted of a planar, ring-shaped base. It was also designed to fit so that the posterior end fit into the region of the posterior fornix and the anterior end fit into the pubic notch. From this position there was an attached inflatable member that expanded from the planar body at approximately a 90 degree angle. This design was stable and did not rotate or translate when the expandable member was repeatedly inflated and deflated. However, upon inflation, the device was not able to occlude the rectum. This lack of occlusion resulted from the fact that the width of the stabilizing base stretched the vaginal tissue taught adjacent to the expandable portion, thereby eliminating the slack in the tissue necessary to deflect the tissue posteriorly. This study demonstrated the importance of stabilization feature and a shape that fits in the regions of the posterior fornix and notch of the pelvic floor. However, it also demonstrated that these features were not sufficient to allow for rectal occlusion. The results suggested that a device design with a base that is narrower in the region where expansion would occur would allow the RVS to remain slack such that an expandable member in the vagina could occlude the rectum.

Cadaver 3 Summary:

This study confirmed the results of Cadaver 2, wherein the LiveSure V3 fit stably but was not able to occlude the rectum. The LiveSure V5 was tested. This device shared the features of planarity and anchoring points in the posterior fornix and pubic notch with the LiveSure V3, however it narrowed in the base in the region proximate the expandable portion. In this manner, it was able to occlude the rectum with minimal force. In fact, there was almost a 1:1 transfer of force applied in the vagina and force felt in the rectum. This demonstrates that very little force was being placed on the rectovaginal septum—preventing stress and strain on the tissue while still being able to occlude the rectum. This was achieved because in its unexpanded state, the narrower profile allowed for extra slack in the vaginal walls that could then be taken up when the device expanded posteriorly.

Cadaver 4 Summary:

This confirmed the findings from Cadaver 3.

Discussion:

Cadaver 1 demonstrated the possibility of occluding the rectum with a vaginal device, but it lacked stability and directional expansion, and required high pressure and stretch to the tissue. Cadaver 2 demonstrated stability and directionality but tautness of the tissue prevented rectal occlusion. Cadaver 3 was successful in all three criteria. Cadaver 4 reaffirmed the results in Cadaver 3.

The LiveSure design in cadaver 4 demonstrated the functionality that we desire for treating fecal incontinence. It was able to occlude the rectum without stretching the RVS or generating excessive pressure in the LiveSure. It also maintained a stable and repeatable orientation, and expansion of the members was always directed towards the RVS. This design was based on the iterative feedback from our other cadaver experiments, discussions with physicians (urogynecologists, gynecologists, and colorectal surgeons), and literature. It required the development of unique, and key-enabling features not present in the prior art. Such features are described in detail in the specification and claims below.

EXAMPLE 2

The following are manufacturing instructions for assembling the device.

Apply Silicone Adhesive to Springs.
Insert Wire forms into Springs and cure adhesive.
Insert assembly into outer tubing.
Bond free ends of tubing together and cure adhesive.

Bond inflation tube and balloon bottom to balloon, cure assembly.

Bond balloon assembly to base assembly and cure.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. An intravaginal device for the control of stool passage of a female user, the device comprising:
    a reversibly extendable force applying portion having an extended state and a nonextended state; and
    an intravaginal stabilizing body supporting the force applying portion, the stabilizing body extending in a longitudinal direction and in a lateral direction that is substantially perpendicular to the longitudinal direction, the stabilizing body having a laterally narrower portion and a laterally wider portion, and the greatest lateral extent of the force applying portion being narrower than the greatest lateral extent of the stabilizing body,
    wherein the stabilizing body is sized and configured to fit entirely within a vaginal cavity of the user with the longitudinal extent of the stabilizing body extending substantially along a length of the vaginal cavity to hold the force applying portion in contact with the user's recto-vaginal septum to control the passage of stool through a rectum of the user.

2. The device of claim 1, wherein the device comprises a first engagement surface adapted to engage the vagina in the area of the pubic notch and a second engagement surface adapted to engage the vagina in the area of the posterior fornix.

3. The intravaginal device of claim 2 wherein the device is adapted to securely engage the pubic symphysis and the posterior fornix.

4. The device of claim 2, wherein the force applying portion is adapted to contact the recto-vaginal septum above the perineal body when the first engagement surface engages the vagina in the area of the pubic notch and the second engagement surface engages the vagina in the area of the posterior fornix.

5. The device of claim 2 wherein the stabilizing body comprises a ring, the first engagement surface being disposed on a first end of the ring and the second engagement surface being disposed on a second end of the ring opposite the first side.

6. The device of claim 1 wherein the force applying portion has a width of 1-6 cm and a length of 1-6 cm.

7. The device of claim 6 wherein the force applying portion has a width of 3-4 cm and a length of 2-5 cm.

8. The device of claim 1 wherein the device is adapted to prevent rotation about an axis extending from an anterior end to a posterior end of the device during the extended and non-extended states.

9. The device of claim 1 wherein the stabilizing body has a lateral span that is narrower in proximity to the force applying portion than in a region not in proximity to the force applying portion.

10. The device of claim 1 wherein the force applying portion is disposed in a proximal portion of the stabilizing body.

11. The device of claim 1 wherein the stabilizing body is generally planar, the force applying portion extending out of the plane of the stabilizing body.

12. The device of claim 1 wherein the force applying portion comprises a supportive member adapted to prevent deflection of the force applying portion.

13. The device of claim 1 wherein the device is configured to support the force applying portion against the recto-vaginal septum above the perineal body in the extended and non-extended states.

14. The device of claim 1, wherein the force applying portion is foldable into the stabilizing body.

15. The device of claim 1, wherein the force applying portion includes a spring adapted to expand the force applying portion.

16. The device of claim 1, wherein the device comprises a portion adapted to accommodate a cervix.

17. The device of claim 1, wherein the device includes suction features adapted to stabilize the device within the vagina.

18. The device of claim 1, wherein the force applying portion includes an electromagnetic system.

19. The device of claim 1, wherein the force applying portion is positioned along the laterally narrower portion of the stabilizing body.

20. The device of claim 19, wherein the laterally narrower portion of the stabilizing body comprises a proximal portion of the stabilizing body that is configured to be positioned in a superior portion of the vaginal cavity.

21. The device of claim 19, wherein the greatest lateral extent of the force applying portion is supported by the laterally narrower portion of the stabilizing body.

22. The device of claim 19, wherein substantially the entire force applying portion is positioned along the laterally narrower portion of the stabilizing body.

23. The device of claim 1, wherein the device is sized and configured such that tension in the vaginal wall in a superior portion of the vagina is less than tension in the vaginal wall in an inferior portion of the vaginal cavity when the device is disposed in the vaginal cavity and the force applying portion is in the nonextended state.

24. The device of claim 1, wherein the force applying portion is positioned along a proximal portion of the stabilizing body that is configured to be positioned in a superior portion of the vaginal cavity.

25. The device of claim 24, wherein the stabilizing body is substantially planar.

26. The device of claim 1, wherein the stabilizing body is in the form of one or more wire forms enclosed in tubing.

27. The device of claim 26, wherein the stabilizing body further comprises one or more springs.

28. The device of claim 1, wherein the stabilizing body includes a first wire form that extends along a first side of the stabilizing body, a second wire form that extends along a second side of the stabilizing body, and a spring that connects an end of the first wire form to an end of the second wire form.

29. The device of claim 28, wherein the spring is configured to allow the stabilizing body to be folded along a length of the device.

30. The device of claim 1, wherein the force applying portion comprises a balloon.

31. The device of claim 1, wherein the device is sized and configured to fit entirely within the vaginal cavity of the user.

32. A method of selectively occluding a rectum to inhibit stool passage in a female user, the method comprising:
inserting an intra-vaginal device into the user's vagina;
stably supporting a force applying portion of the device against a recto-vaginal septum of the user while the force applying portion is in a nonextended state and slack is maintained in a region of a vaginal wall of the user adjacent the nonextended force applying portion;
extending the force applying portion to an extended state to apply a force with the force applying portion against the recto-vaginal septum while stably supporting the force applying portion against the recto-vaginal septum to impede passage of stool through the rectum of the user; and
after extending the force applying portion to the extended state to apply the force with the force applying portion against the recto-vaginal septum, reducing the force sufficiently to permit stool to pass through the rectum.

33. The method of claim 32 wherein the device further comprises a stabilizing body, and stably supporting the force applying portion of the device against the recto-vaginal septum comprises engaging the stabilizing body with the vagina in the area of the pubic notch and in the area of the posterior fornix.

34. The method of claim 32 further comprising, after reducing the force sufficiently to permit stool to pass through the rectum, maintaining the force applying portion against the recto-vaginal septum above the perineal body.

35. The method of claim 32, wherein the device comprises an intravaginal stabilizing body having a laterally narrower portion and a laterally wider portion, and the force applying portion is positioned along the laterally narrower portion of the stabilizing body.

36. The method of claim 35, wherein the laterally narrower portion of the stabilizing body comprises a proximal portion of the stabilizing body that is configured to be positioned in a superior portion of the vaginal cavity.

37. The method of claim 35, wherein the greatest lateral extent of the force applying portion is supported by the laterally narrower portion of the stabilizing body.

38. The method of claim 35, wherein substantially the entire force applying portion is positioned along the laterally narrower portion of the stabilizing body.

39. The method of claim 32, wherein the stabilizing body is substantially planar.

40. An intravaginal device for the control of stool passage of a female user, the device comprising:
a reversibly extendable force applying portion having an extended state and a nonextended state; and
an intravaginal stabilizing body supporting the force applying portion, the stabilizing body having a laterally narrower portion and a laterally wider portion, and the greatest lateral extent of the force applying portion being narrower than the greatest lateral extent of the stabilizing body,
wherein the stabilizing body has a lateral span that is narrower in proximity to the force applying portion than in a region not in proximity to the force applying portion, and the stabilizing body is sized and configured to fit entirely within a vaginal cavity of the user to hold the force applying portion in contact with the user's recto-vaginal septum to control the passage of stool through a rectum of the user.

41. An intravaginal device for the control of stool passage of a female user, the device comprising:
a reversibly extendable force applying portion having an extended state and a nonextended state; and
an intravaginal stabilizing body supporting the force applying portion, the stabilizing body having a laterally narrower portion and a laterally wider portion, and the greatest lateral extent of the force applying portion being narrower than the greatest lateral extent of the stabilizing body,
wherein the stabilizing body is sized and configured to fit entirely within a vaginal cavity of the user to hold the force applying portion in contact with the user's recto-vaginal septum to control the passage of stool through a rectum of the user, and the device is sized and configured such that tension in the vaginal wall in a superior portion of the vagina is less than tension in the vaginal wall in an inferior portion of the vaginal cavity when the device is disposed in the vaginal cavity and the force applying portion is in the nonextended state.

* * * * *

UNITED STATES PATENT AND TRADEMARK OFFICE
CERTIFICATE OF CORRECTION

PATENT NO. : 9,072,578 B2  
APPLICATION NO. : 13/635598  
DATED : July 7, 2015  
INVENTOR(S) : Steven Lawrence Herbowy, Miles Harris Rosen and Jacob Samuel Brenner It is certified that error appears in the above-identified patent and that said Letters Patent is hereby corrected as shown below:

In the specification

Column 1, line 7, delete "Phasc" and insert -- Phase --.

Signed and Sealed this  
Twenty-fourth Day of November, 2015

Michelle K. Lee  
*Director of the United States Patent and Trademark Office*